(12) United States Patent
Lucas et al.

(10) Patent No.: US 10,000,572 B2
(45) Date of Patent: Jun. 19, 2018

(54) METHOD FOR INHIBITING THE IMMUNE SUPPRESSIVE FUNCTION OF HUMAN T REGULATORY CELLS BY ADMINISTERING AN ANTI-GARP MONOCLONAL ANTIBODY

(71) Applicants: LUDWIG INSTITUTE FOR CANCER RESEARCH LTD, Zurich (CH); UNIVERSITÉ CATHOLIQUE DE LOUVAIN, Louvain la Neuve (BE)

(72) Inventors: Sophie Lucas, Tervuren (BE); Pierre Coulie, Kraainem (BE); Julia Cuende Villasur, Louvain (BE); Laure Dumoutier, Orbais (BE); Jean-Christophe Renauld, Kraainem (BE)

(73) Assignees: UNIVERSITÉ CATHOLIQUE DE LOUVAIN, Louvain-la-Neuve (BE); LUDWIG INSTITUTE FOR CANCER RESEARCH LTD, Zurich (CH)

( * ) Notice: Subject to any disclaimer, the term of this patent is extended or adjusted under 35 U.S.C. 154(b) by 0 days. days.

(21) Appl. No.: 14/908,368

(22) PCT Filed: Aug. 1, 2014

(86) PCT No.: PCT/EP2014/066650
§ 371 (c)(1),
(2) Date: Jan. 28, 2016

(87) PCT Pub. No.: WO2015/015003
PCT Pub. Date: Feb. 5, 2015

(65) Prior Publication Data
US 2016/0272717 A1 Sep. 22, 2016

Related U.S. Application Data

(60) Provisional application No. 61/861,008, filed on Aug. 1, 2013.

(30) Foreign Application Priority Data

Aug. 1, 2013 (EP) ..................................... 13178958
May 7, 2014 (EP) ..................................... 14167425

(51) Int. Cl.
*C07K 16/28* (2006.01)
*A61K 39/395* (2006.01)
*C07K 16/30* (2006.01)
*A61K 39/00* (2006.01)

(52) U.S. Cl.
CPC .......... *C07K 16/2875* (2013.01); *C07K 16/28* (2013.01); *C07K 16/30* (2013.01); *A61K 2039/505* (2013.01); *C07K 2317/22* (2013.01); *C07K 2317/24* (2013.01); *C07K 2317/31* (2013.01); *C07K 2317/32* (2013.01); *C07K 2317/41* (2013.01); *C07K 2317/54* (2013.01);
*C07K 2317/55* (2013.01); *C07K 2317/565* (2013.01); *C07K 2317/569* (2013.01); *C07K 2317/622* (2013.01); *C07K 2317/624* (2013.01); *C07K 2317/626* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,816,567 | A | 3/1989 | Cabilly et al. |
| 5,591,828 | A | 1/1997 | Bosslet et al. |
| 5,892,019 | A | 4/1999 | Schlom et al. |
| 6,162,963 | A | 12/2000 | Kucherlapati et al. |
| 9,399,676 | B2 * | 7/2016 | Schurpf ............... C07K 14/495 |
| 9,573,995 | B2 | 2/2017 | Schurpf et al. |
| 2008/0279834 | A1 | 11/2008 | Garaczi et al. |
| 2011/0300119 | A1 | 12/2011 | Tran et al. |

FOREIGN PATENT DOCUMENTS

| EP | 0 404 097 A2 | 12/1990 |
| EP | 0 799 836 A1 | 10/1997 |
| EP | 2 832 747 A1 | 2/2015 |
| WO | 1993/011161 A1 | 6/1993 |
| WO | 2005/102387 A2 | 11/2005 |
| WO | 2006/085938 A2 | 8/2006 |
| WO | 2007/113301 A1 | 10/2007 |
| WO | 2009/073163 A1 | 6/2009 |
| WO | 2010/001251 A2 | 1/2010 |
| WO | 2014/182676 A2 | 11/2014 |
| WO | 2014182676 A2 | 11/2014 |
| WO | 2015/015003 A1 | 2/2015 |

OTHER PUBLICATIONS

Klimka et al. Human anti-CD30 recombinant antibodies by guided phage antibody selection using cell panning, British Journal of Cancer 83, 252-260, 2000.*
Padlan et al., Structure of an antibody-antigen complex: crystal structure of the HyHEL-10 Fab-lysozyme complex, Pnas, 86, 5938-594, 1989.*
LRRC32 antibody Plato-1, accessed Sep. 14, 2017.*
Merchant et al. (1998) "An efficient route to human bispecific IgG," Nat. Biotechnol. 167(7):677-681.
Miyara et al. (2009) "Functional delineation and differentiation dynamics of human CD4+ T cells expressing the FoxP3 transcription factor," Immunity. 30:899-911.

(Continued)

*Primary Examiner* — Elly-Gerald Stoica
(74) *Attorney, Agent, or Firm* — Lathrop Gage LLP

(57) ABSTRACT

The present invention relates to an antibody binding to the transmembrane protein 'glycoprotein A repetitions predominant' (GARP) in the presence of TGF-β and uses thereof.

8 Claims, 23 Drawing Sheets

(56) References Cited

OTHER PUBLICATIONS

Morea (2000) et al. "Antibody modeling: implications for engineering and design," Methods. 20(3):267-279.
Morrison et al. (1984) "Chimeric human antibody molecules: mouse antigen-binding domains with human constant-region domains," Proc. Natl. Acad. Sci. USA. 81(21):6851-6855.
Natsume et al. (2009) "Improving effector functions of antibodies for cancer treatment: Enhancing ADCC and CDC," Drug Design Development and Therapy. 3:7-16.
Ono et al. (1999) "The humanized anti-HM1.24 antibody effectively kills multiple myeloma cells by human effector cell-mediated cytotoxicity," Mol. Immunol. 36:387-395.
Pluckthun (1994) "Antibodies from *Escherichia coli*," In; The Pharmacology of Monoclonal Antibodies. Rosenberg et al.: Eds. Springer-Verlag. vol. 113. pp. 269-315.
Presta et al. (1992) "Antibody engineering," Curr. Opin. Struct. Biol. 3:394-398.
Presta et al. (1993) "Humanization of an antibody directed against IgE," J. Immunol. 151(5):2623-2632.
Qu et al. (1999) "Humanization of Immu31, an alpha-fetoprotein-specific antibody," Clin. Cancer Res. 5:3095s-3100s.
Ridgway et al. (1996) "Knobs-into-holes' engineering of antibody CH3 domains for heavy chain heterodimerization," Protein Eng. 9(7):617-621.
Riechmann et al. (1988) "Reshaping human antibodies for therapy," Nat. 332(6162):323-327.
Roux et al. (1998) "Comparisons of the ability of human IgG3 hinge mutants, IgM, IgE, and IgA2, to form small immune complexes: a role for flexibility and geometry," J. Immunol. 161:4083-4090.
Rudikoff et al. (1982) "Single amino acid substitution altering antigen-binding specificity," Proc. Natl. Acad. Sci. USA. 79(6):1979-1983.
Scatchard et al. (1949) "The attractions of proteins for small molecules and ions," Ann. NY Acad. Sci. 51:660-672.
Shopes (1992) "A genetically engineered human IgG mutant with enhanced cytolytic activity," J. Immunol. 148:2918-2922.
Shultz et al. (Oct. 12, 2012) "Humanized mice for immune system investigation: progress, promise and challenges," Nat. Rev. Immunol. 12:786-798.
Sims et al. (1993) "A humanized CD18 antibody can block function without cell destruction," J. Immunol. 151 (4):2296-2308.
Stevenson et al. (1989) "A chimeric antibody with dual Fc regions (bisFabFc) prepared by manipulations at the IgG hinge," Anti-Cancer Drug Design. 3:219-230.
Stockis et al. (2009) "Comparison of stable human Treg and Th clones by transcriptional profiling," Eur. J. Immunol. 39:869-882.
Stockis et al. (2009) "Membrane protein GARP is a receptor for latent TGF-beta on the surface of activated human Treg," Eur. J. Immunol. 39(12):3315-3322.
Tomlinson et al. (1995) "The structural repertoire of the human V kappa domain," EMBO J. 14:4628-4638.
Tramontano et al. (1989) "Structural determinants of the conformations of medium-sized loops in proteins," Proteins. 6:382-394.
Tramontano et al. (1990) "Framework residue 71 is a major determinant of the position and conformation of the second hypervariable region in the VH domains of immunoglobulins," J. Mol. Biol. 215:175-182.
Tran et al. (2009) "GARP (LRRC32) is essential for the surface expression of latent TGF-beta on platelets and activated FOXP3+ regulatory T cells," Proc. Natl. Acd. Sci. USA. 106(32):13445-13450.
Urlaub et al. (1980) "Isolation of Chinese hamster cell mutants deficient in dihydrofolate reductase activity," Proc. Natl. Acad. Sci. USA. 77(7):4216-4220.
Verhoeyen et al. (1988) "Reshaping human antibodies: grafting an antilysozyme activity," Science. 239 (4847):1534-1536.
Wang et al. (Mar. 1, 2012) "GARP regulates the bioavailability and activation of TGFβ," Mol. Biol. Cell. 1129-1139.
Williams et al. (1996) "Sequence and evolution of the human germline V lambda repertoire," J. Mol. Biol. 264:220-232.

Yamane-Ohnuki et al. (2009) "Production of therapeutic antibodies with controlled fucosylation," mAbs. 1 (3):230-236.
Zhou et al. (Apr. 10, 2013) "GARP-TGF-β complexes negatively regulate regulatory T cell development and maintenance of peripheral CD4+ T cells in vivo," J. Immunol. 190(10):5057-5064.
International Search Report with Written Opinion corresponding to International Patent Application No. PCT/EP2014/066650, dated Oct. 30, 2014.
Engelman et al. (Feb. 2008) "Acquired resistance to tyrosine kinase inhibitors during cancer therapy," Current Opinion in Genetics & Development. 18(1):73-9.
Kovacs et al. (2015) "Cardiac Safety of TGF-beta Receptor I Kinase Inhibitor LY2157299 Monohydrate in Cancer Patients in a First-in Human Dose Study," Cardiovasc Toxicol. 15(4):309-323.
Lacouture et al. (2015) "Cutaneous keratoacanthomas/squamous cell carcinomas associated with neutralization of transforming growth factor beta by the monoclonal antibody fresolimumab (GC1008)," Cancer Immunol Immunother. 54(4):437-446.
Li et al. (2006) "Transforming growth factor-beta regulation of immune responses," Annu Rev Immunol. 24:99-146.
Lucas et al. (2012) "Demethylation of the FOXP3 gene in human melanoma cells precludes the use of this epigenetic mark for quantification of Tregs in unseparated melanoma samples," Int J Cancer. 130(8)1960-1966.
Shull et al. (1992) "Targeted disruption of the mouse transforming growth factor-beta 1 gene results in multifocal inflammatory disease," Nature. 359(6397):693-699.
Silence et al. (2014) "ARGX-110, a highly potent antibody targeting CD70, eliminates tumors via both enhanced ADCC and immune checkpoint blockade," MAbs. 6(2):523-532.
Tan et al. (2013) "Cellular re- and de-programming by microenvironmental memory: why short TGF-beta1 pulses can have long effects," Fibrogenesis Tissue Repair. 6(1):12.
Zheng et al. (May 2007) "Foxp3 in control of the regulatory T cell lineage," Nat Immunol. 8(5):457-462.
Zheng et al. (Feb. 2007) "Genome-wide analysis of Foxp3 target genes in developing and mature regulatory T cells," Nature. 445(7130):936-940.
Third Party Observation corresponding to European Patent Application No. 14748185.7, dated Jan. 13, 2017.
U.S. Appl. No. 61/819,840, corresponding to European Publication No. WO 2014/182676, dated May 6, 2013.
Akhurst et al. (Sep. 24, 2012) "Targeting the TGFβ signalling pathway in disease," Nat. Rev. Drug. Discovery. 11(10):790-811.
Altschul et al. (1990) "Basic local alignment search tool," J. Mol. Biol. 215:403-410.
Armour et al. (1999) "Recombinant human IgG molecules lacking Fcgamma receptor I binding and monocyte triggering activities," Eur. J. Immunol. 29:2613-2624.
Basilico et al. (May 27, 2014) "Four individually druggable MET hotspots mediate HGF-driven tumor progression," J. Clin. Invest. 124:3172-3186.
Boon et al. (2006) "Human T cell responses against melanoma," Annu. Rev. Immunol. 24:175-208.
Cai et al. (Mar. 13, 2011) "An immunotoxin targeting the gH glycoprotein of KSHV for selective killing of cells in the lytic phase of infection," Antiviral Research. 90(3):143-150.
Carillo et al. (1988) "The Multiple Sequence Alignment Problem in Biology," SIAM J. Applied Math. 48:1073-1082.
Caron et al. (1992) "Engineered humanized dimeric forms of IgG are more effective antibodies," J. Exp. Med. 176:1191-1195.
Carter et al. (1992) "Humanization of an anti-p185HER2 antibody for human cancer therapy," Proc. Natl. Acad. Sci. USA. 89:4285-4289.
Chan et al. (2010) "Therapeutic antibodies for autoimmunity and inflammation," Nat. Rev. Immunol. 10:301-316.
Chomczynski et al. (1987) "Single-step method of RNA isolation by acid guanidinium thiocyanate-phenol-chloroform extraction," Anal. Biochem. 162:156-159.
Chothia et al. (1987) "Canonical structures for the hypervariable regions of immunoglobulins," J. Mol. Biol. 196:901-917.59.
Chothia et al. (1992) "Structural repertoire of the human VH segments," J. Mol. Biol. 227:799-817.

(56) References Cited

OTHER PUBLICATIONS

Clackson et al. (1991) "Making antibody fragments using phage display libraries," Nat. 352:624-628.
Colombo et al. (2007) "Regulatory-T-cell inhibition versus depletion: the right choice in cancer immunotherapy," Nat. Rev. Cancer. 7:880-887.
Cuende (Apr. 22, 2015) "Monoclonal antibodies against GARP/TGF-b1 complexes inhibit the immunosuppressive activity of human regulatory T cells in vivo," Human Immunology. 7(284):284ra56. pp. 1-12.
Daley et al. (2005) "Application of monoclonal antibodies in functional and comparative investigations of heavy-chain immunoglobulins in new world camelids," Clin. Diagn. Lab. Immunol. 12(3):380-386.
De Haard (1999) "A large non-immunized human Fab fragment phage library that permits rapid isolation and kinetic analysis of high affinity antibodies," J. Biol. Chem. 274(26):18218-18230.
De Haard (2005) "Llama antibodies against a lactococcal protein located at the tip of the phage tail prevent phage infection," J. Bacteriol. 187:4531-4541.
De Vries et al. (Dec. 21, 2010) "Frequency of circulating Tregs with demethylated FOXP3 intron 1 in melanoma patients receiving tumor vaccines and potentially Treg-depleting agents," Clin. Cancer Res. 17:841-848.
Delgado et al. (1996) "Enhanced tumour specificity of an anti-carcinoembrionic antigen Fab' fragment by poly(ethylene glycol) (PEG) modification," Br. J. Cancer. 73(2):175-182.
Devereux et al. (1984) "A comprehensive set of sequence analysis programs for VAX," Nucl. Acids Res. 12(1 Pt 1):387-395.
Edwards et al. (May 3, 2013) "Regulation of the expression of GARP/latent TGF-β1 complexes on mouse T cells and their role in regulatory T cell and Th17 differentiation," J. Immunol. 190(11):5506-5515.
Gauthy et al. (Sep. 30, 2013) "GARP is regulated by miRNAs and controls latent TGF-β1 production by human regulatory T cells," PloS One. 8(9):e76186. pp. 1-13.
Genbank Database [Online] (2003) "Immunoglobulin heavy chain variable region, partial [Mus musculus]," Accession No. AAO19657.1. National Center for Biotechnology Information. Accessible on the Internet at URL: http://www.ncbi.nih.gov/protein/27752388. [Last Accessed Mar. 24, 2016].
Genbank Database [Online] (Apr. 30, 2011) "Mus musculus clone YC15 anti-KSHV gH immunoglobulin light chain variable region mRNA, partial cds," Accession No. JF330319.1. National Center for Biotechnology Information. Accessible on the Internet at URL: http://www.ncbi.nlm.nih.gov/nuccore/JF330319.1. [Last Accessed Mar. 24, 2016].
Genbank Database [Online] (Oct. 17, 2015) "*Homo sapiens* transforming growth factor, beta 1 (TGFB1), mRNA," Accession No. NM_000660. National Center for Biotechnology Information. Accessible on the Internet at URL: http://www.ncbi.nlm.nih.gov/nuccore/NM_000660. [Last Accessed Mar. 24, 2016].
Genbank Database [Online] (Mar. 15, 2015) "*Homo sapiens* leucine rich repeat containing 32 (LRRC32), transcript variant 2, mRNA," Accession No. NM_001128922. National Center for Biotechnology Information. Accessible on the Internet at URL: http://www.ncbi.nlm.nih.gov/nuccore/NM_001128922. [Last Accessed Mar. 24, 2016].
Genbank Database [Online] (Nov. 7, 2015) "*Homo sapiens* transforming growth factor beta 2 (TGFB2), transcript variant 1, mRNA," Accession No. NM_001135599. National Center for Biotechnology Information. Accessible on the Internet at URL: http://www.ncbi.nlm.nih.gov/nuccore/NM_001135599. [Last Accessed Mar. 24, 2016].
Genbank Database [Online] (Nov. 7, 2015) "*Homo sapiens* transforming growth factor beta 2 (TGFB2), transcript variant 2, mRNA," Accession No. NM_003238. National Center for Biotechnology Information. Accessible on the Internet at URL: http://www.ncbi.nlm.nih.gov/nuccore/NM_003238. [Last Accessed Mar. 24, 2016].
Genbank Database [Online] (Mar. 12, 2015) "Predicted: *Homo sapiens* transforming growth factor, beta 3 (TGFB3), transcript variant X1, mRNA," Accession No. XM_005268028. National Center for Biotechnology Information. Accessible on the Internet at URL: http://www.ncbi.nlm.nih.gov/nuccore/XM_005268028. [Last Accessed Mar. 24, 2016].
Genbank Database [Online] (Jan. 25, 2016) "Predicted: Macaca fascicularis leucine rich repeat containing 32 (LRRC32), transcript variant X1, mRNA," Accession No. XM_005579140. National Center for Biotechnology Information. Accessible on the Internet at URL: http://www.ncbi.nlm.nih.gov/nuccore/XM_005579140. [Last Accessed Mar. 24, 2016].
Genbank Database [Online] (Jan. 25, 2016) "Predicted: Macaca fascicularis transforming growth factor beta 1 (TGFB1), transcript variant X1, mRNA," Accession No. XM_005589338. National Center for Biotechnology Information. Accessible on the Internet at URL: http://www.ncbi.nlm.nih.gov/nuccore/XM_005589338. [Last Accessed Mar. 24, 2016].
Graham et al. (1977) "Characteristics of a human cell line transformed by DNA from human adenovirus type 5," J. Gen. Virol. 36:59-72.
Hannon et al. (Jun. 17, 2013) "Infusion of clinical-grade enriched regulatory T cells delays experimental xenogeneic graft-versus-host disease," Transfusion. 54(2):353-363.
Holliger et al. (1993) "'Diabodies': small bivalent and bispecific antibody fragments," Proc. Natl. Acad. Sci. USA. 90:6444-6448.
Jakobovitz et al. (1993) "Germ-line transmission and expression of a human-derived yeast artificial chromosome," Nat. 362:255-258.
Jones et al. (1986) "Replacing the complementarity-determining regions in a human antibody with those from a mouse," Nat. 321:522-525.
Kabat et al. (1977) "Unusual distributions of amino acids in complementarity-determining (hypervariable) segments of heavy and light chains of immunoglobulins and their possible roles in specificity of antibody-combining sites," J. Biol. Chem. 252:6609-6616.
Kohler et al. (1975) "Continuous cultures of fused cells secreting antibody of predefined specificity," Nat. 256:495-497.
Kretchmer et al. (2002) "Strong antigenic selection shaping the immunoglobulin heavy chain repertoire of B-1a lymphocytes in lambda 2(315) transgenic mice," Eur. J. Immunol. 32:2317-2327.
Lefranc et al. (1999) "IMGT, the international ImMunoGeneTics database," Nucl. Acids Res. 27:209-212.
Lemaire et al. (Feb. 17, 2011) "Induction of autoantibodies against mouse soluble proteins after immunization with living cells presenting the autoantigen at the cell surface in fusion with a human type 2 transmembrane protein," J. Immunol. Methods. 367(1-2):56-62.
Leong et al. (2001) "Adapting pharmacokinetic properties of a humanized anti-interleukin-8 antibody for therapeutic applications using site-specific pegylation," Cytokines. 16(3):106-119.
Lonning et al. (Dec. 2011) "Antibody targeting of TGF-β in cancer patients," Current Pharmaceutical Biotechnology. 12:2176-2189.
MacCallum et al. (1996) "Antibody-antigen interactions: contact analysis and binding site topography," J. Mol. Biol. 262:732-745.
Marks et al. (1991) "By-passing immunization. Human antibodies from V-gene libraries displayed on phage," J. Mol. Biol. 222:581-597.
Martin et al. (1996) "Structural families in loops of homologous proteins: automatic classification, modelling and application to antibodies," J. Mol. Biol. 263:800-815.
Mather et al. (1980) "Establishment and characterization of two distinct mouse testicular epithelial cell lines," Biol. Reprod. 23:243-251.
Mather et al. (1982) "Culture of testicular cells in hormone-supplemented serum-free medium," Ann. NY Acad. Sci. 383:44-68.
Liewen et al. (2005) "Characterization of the human GARP (Golgi associated retrograde protein) complex," Exp. Cell Res. 306(1):24-34.
Miller et al. (Jan. 18, 2014) "CD4+CD25+ T regulatory cells activated during feline immunodeficiency virus infection convert T helper cells into functional suppressors through a membrane-bound TGFβ / GARP-mediated mechanism," Virol. J. 11(1):7. pp. 1-14.

(56) References Cited

OTHER PUBLICATIONS

International Search Report with Written Opinion corresponding to International Patent Application No. PCT/IB2016/000182, dated May 10, 2016, 15 pages.

Non-Final Rejection corresponding to U.S. Appl. No. 15/013,706, dated Nov. 1, 2017, 14 pages.

* cited by examiner

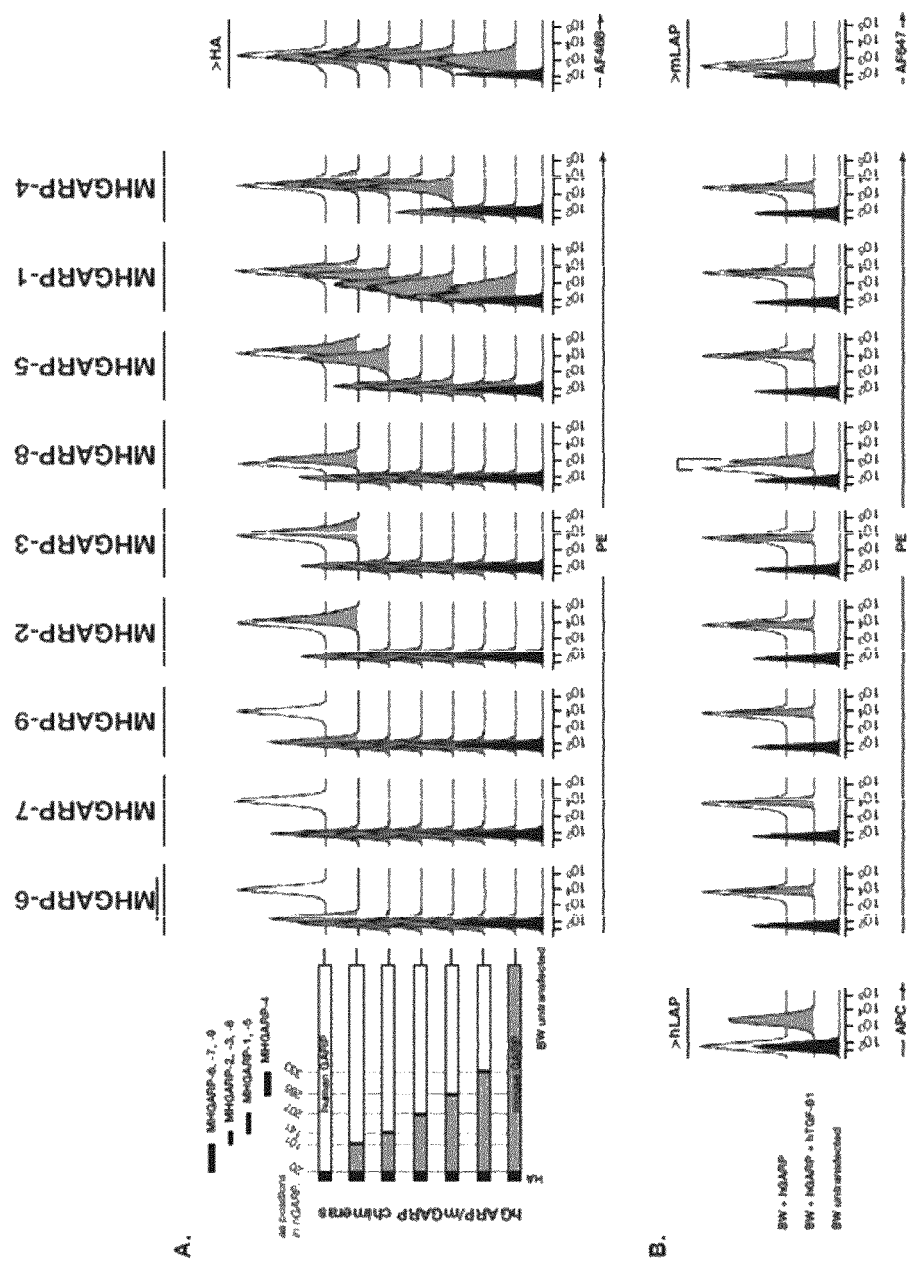
FIG. 3A-B

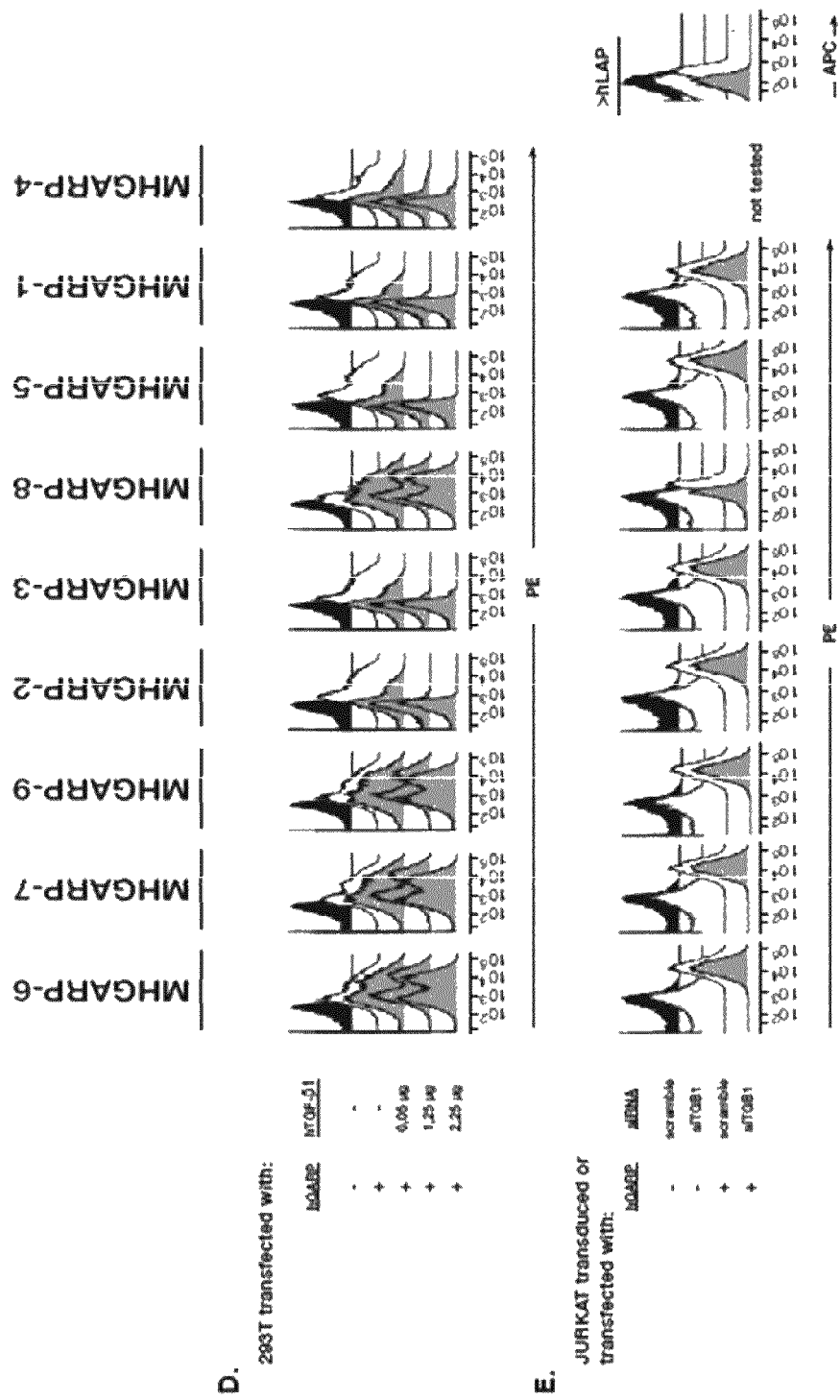
FIG. 3D-E

A
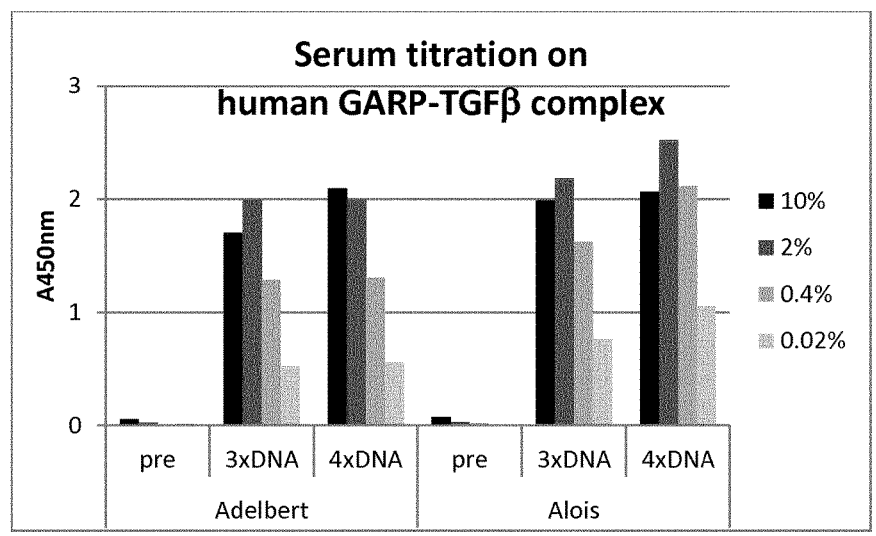
B
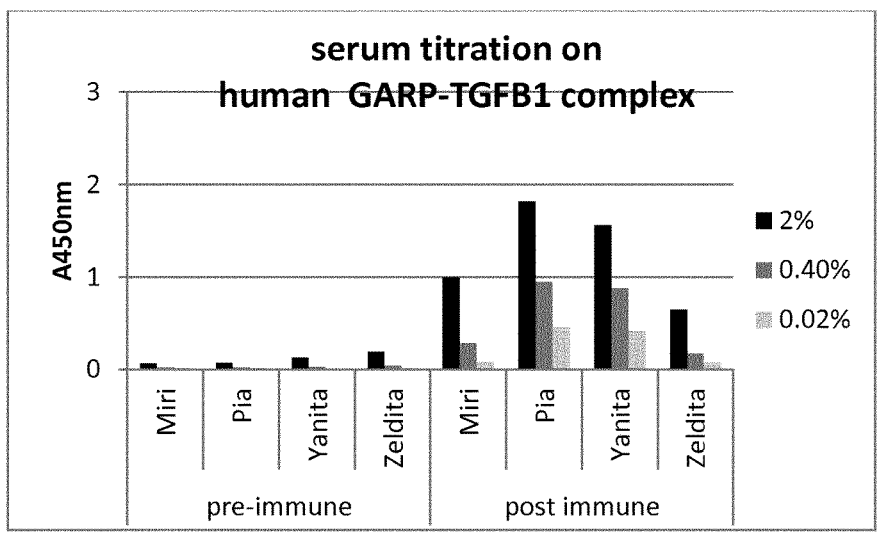
FIG. 8

LHG10 VH sequences

```
                        CDR1                          CDR2
LHG-10  EVQLVQPGAELRNSGASVKVSCKASGYRFT STYID WVRQAPGQGLEWMG RIDPEDGGTKYAQKFQG RVTFTADTSTSTAVELSSLRSEDTAVYYCAR NEWETVVGDLMYEYEY
                                                                                                            CDR3
        WGQGTQVTVSS
```

LHG10 VL sequences

```
                             CDR1                    CDR2                                   CDR3
LHG10   DIQMTQSPTSLSASLGDRVTITC QASQSISSYLA WYQQKPGQAPKLLIY GASRLQT GVPSRFSGSGSGTSFTLTISGLEAEDAGTYYC QQYDSLPVT FGQGTKVELK
```

VK sequences of affinity optimized shuffle variants of LHG-10

```
                             CDR1                    CDR2                                   CDR3
LHG10    DIQMTQSPTSLSASLGDRVTITC QASQSISSYLA WYQQKPGQAPKLLIY GASRLQT GVPSRFSGSGSGTSFTLTISGLEAEDAGTYYC QQYDSLPVT FGQGTKVELK
LHG10.4  DIQMTQSPSSLSASLGDRVTITC QASQSISSYLA WYQQKPGQAPKLLIY GTSRLKT GVPSRFSGSGSGTSFTLTISGLEAEDAGTYYC QQYYSAPVT FGQGTKVELK
LHG10.6  DIQMTQSPSSLSASLGDRVTITC QASQSISVSYLA WYQQKPGQAPNLLIY GASRLKT GVPSRFSGSGSGTSFTLTISGLEAEDAGTYYC QQYASVPVT FGQGTKVELK
LHG10.3  DIQMTQSPSSLSASLGDRVTITC QASQSIVSYLA WYQQKPGQAPKLLIY GASRLQT GVPSRFSGSGSGTSFTLTISGLEAEDAGTYYC QQYASAPVT FGQGTKVELK
LHG10.5  DIQMTQSPSPLSLGDRVTITC QASQTISSFLA WYHQKPGQPPKLLIY RASIPQT GVPSRFSGSGSGTSFTLTIGGLEAEDAGTYYC QQYVSAPPT FGQGTKVELK

LHG10    DIQMTQSPTSLSASLGDRVTITC QASQSISSYLA WYQQKPGQAPKLLIY GASRLQT GVPSRFSGSGSGTSFTLTISGLEAEDAGTYYC QQYDSLPVT FGQGTKVELK
LHG10.4  ............S............. .............. ................ ...T..K. ................................ ....Y.A.. ..........
LHG10.6  ............S............. .............. ...........NI... ......K. ................................ ....A.V.. ..........
LHG10.3  ............S..P.......... ........V..... ................ ...R..IP. ................................ ....A.A.. ..........
LHG10.5  ............S..P.......... ..T.F......... ....H......P.... ..R.IP. .........................G...... ...V.A.P. ..........
```

Table X: CDR sequences of LHG-10 (VH and VK) as well as those of the affinity optimized VK variants

| mAb | CDR1 | SEQ ID NO | CDR2 | SEQ ID NO | CDR3 | SEQ ID NO |
|---|---|---|---|---|---|---|
| LHG-10 VH | SYYID | 13 | RIDPEDGGTKYAQKFQG | 14 | NEWETVVGDLMYEYEY | 15 |
| LHG10 VK | QASQSISSYLA | 19 | GASRLQT | 20 | QQYDSLPVT | 21 |
| LHG10.3 VK | QASQSIVSYLA | 22 | GASRLQT | 23 | QQYASAPVT | 24 |
| LHG10.4 VK | QASQSISSYLA | 25 | GTSRLKT | 26 | QQYYSAPVT | 27 |
| LHG10.5 VK | QASQTISSFLA | 28 | RASIPQT | 29 | QQYVSAPPT | 30 |
| LHG10.6 VK | QASQSISSYLA | 31 | GASRLKT | 32 | QQYASVPVT | 33 |

FIG. 10

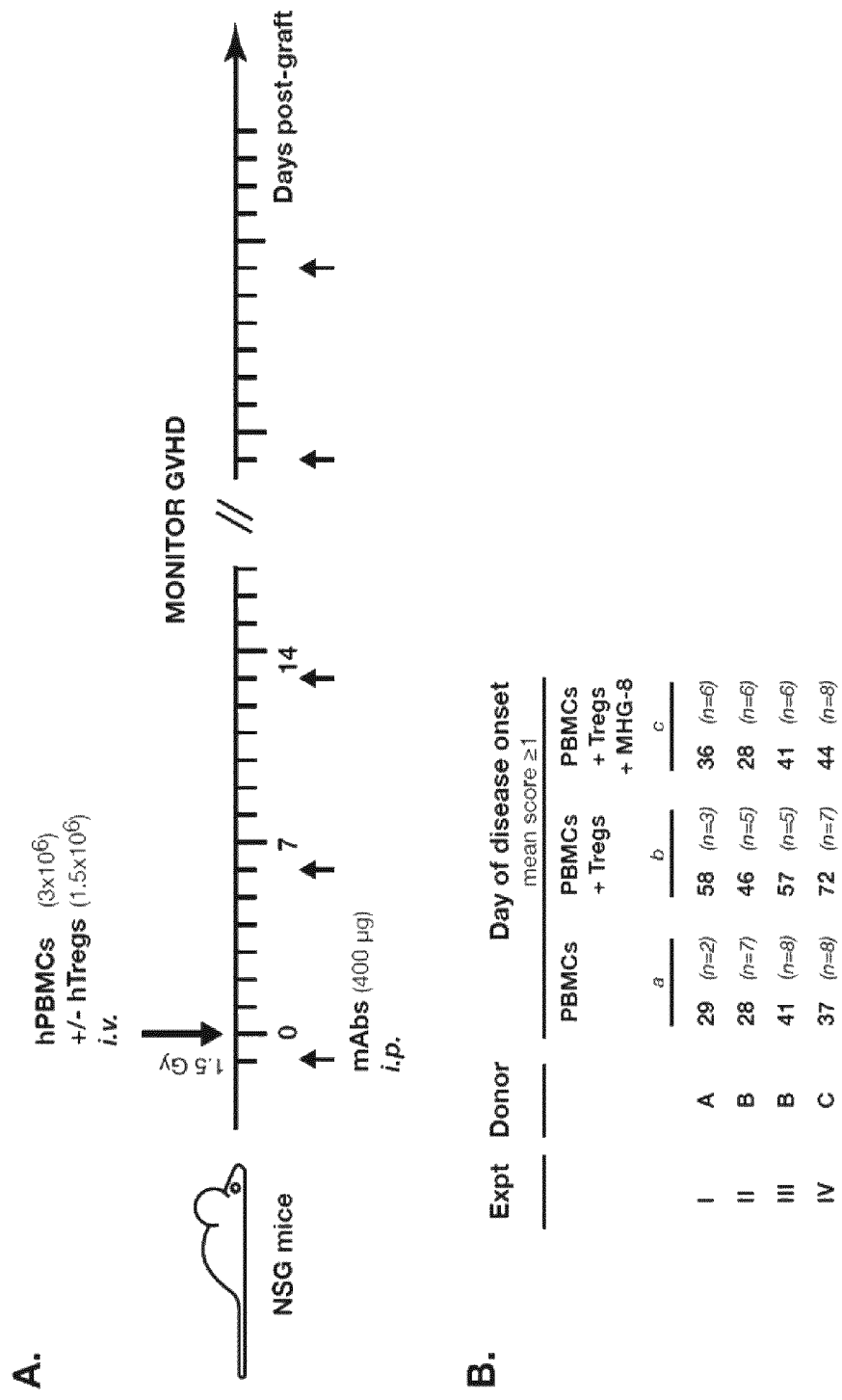
FIG. 16A-B

METHOD FOR INHIBITING THE IMMUNE SUPPRESSIVE FUNCTION OF HUMAN T REGULATORY CELLS BY ADMINISTERING AN ANTI-GARP MONOCLONAL ANTIBODY

RELATED APPLICATIONS

This application is a 35 U.S.C. § 371 filing of International Application No. PCT/EP2014/066650, filed Aug. 1, 2014, which claims priority to European Patent Application No. 13178958.8, filed Aug. 1, 2013, European Patent Application No. 14167425.9, filed May 7, 2014, and U.S. Provisional Patent Application No. 61/861,008, filed Aug. 1, 2013 each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 15, 2016, is named 578295_AGX5-024US_SL.txt and is 46,389 bytes in size.

FIELD OF INVENTION

The present invention relates to human anti-GARP protein that inhibits TGF-β signaling. The present invention also relates to the treatment of immune disorders and diseases such as cancer.

BACKGROUND OF INVENTION

Since the molecular identification of the first human tumor antigens in the early 1990's, several clinical trials were completed to evaluate the effects of therapeutic vaccination of cancer patients with shared tumor-specific antigens (Boon, T. et al. Annu. Rev. Immunol. 2006, 24:175-208). Evidence of tumor regressions was observed in about 20% of the patients, with objective clinical responses in 5-10%. Therefore, vaccination with tumor-specific antigens represents a new promising therapy for treating cancer.

Strategies are needed to improve the proportion of patients that respond to vaccination. The main limiting factor to clinical efficacy of current therapeutic cancer vaccines does not appear to be the vaccine itself, but local factors controlling the tumor microenvironment in which the anti-tumor T cells have to work.

Regulatory T cells, or Tregs, are a subset of CD4+T lymphocytes specialized in the inhibition of immune responses. Insufficient Treg function results in autoimmune pathology, while excessive Treg function may inhibit anti-tumor immune responses in cancer patients. The exact mechanisms by which Tregs inhibit immune responses are not fully understood.

Due to their immunosuppressive functions, Tregs represent potential inhibitors of spontaneous or vaccine-induced anti-tumor immune responses. In murine models, the depletion of Tregs can improve immune responses against experimental tumors (Colombo et al. Nat. Rev. Cancer 2007, 7:880-887). Thus, targeting Tregs in humans could improve the efficacy of immunotherapy against cancer.

As the inventors previously showed that active TGF-β is produced by human Tregs, but not other types of human T lymphocytes (Stockis, J. et al. Eur. J. Immunol. 2009, 39:869-882), TGF-β could be a target of interest.

However, antibodies against hTGF-β were not found promising. Phase 1 clinical trials have been conducted in focal segmental glomerulosclerosis (FSGS), idiopathic pulmonary fibrosis (IPF) and advanced malignant melanoma or renal cell carcinoma (RCC) (Lonning S et al. Current Pharmaceutical Biotechnology 2011, 12:2176-2189). Depending on the trial, adverse events were observed in some patients. The main adverse reactions reported consisted in the development of keratoacanthoma (KA) and squamous cell carcinoma (SCC) in melanoma patients. It is possible that KA or SCC lesions in melanoma patients evolved from pre-cancerous cells whose proliferation was being inhibited by endogenous TGF-β(Lonning S et al. Current Pharmaceutical Biotechnology 2011, 12:2176-2189). Therefore, a major concern regarding the use of anti-TGF-β antibodies in the context of cancer is that they may favor the appearance of new neoplastic lesions, due to the inhibition of the tumor-suppressive effect exerted by endogenous TGF-β on pre-cancerous cells.

One object of the invention is to provide a new strategy for improving cancer treatment by targeting Tregs via their production of TGF-β.

It was previously shown that the production of TGF-β is tightly regulated by a multi-step process. The precursor named pro-TGF-β1 homodimerizes prior to cleavage by pro-protein convertase FURIN. The resulting product is called latent TGF-β1, in which the C-terminal fragment, or mature TGF-β1, remains non-covalently bound to the N-terminal fragment known as the Latency Associated Peptide, or LAP. This latent complex is inactive because LAP prevents mature TGF-β1 from binding to its receptor.

In the present invention, the inventors show that latent TGF-β binds to the surface of Tregs through the transmembrane protein GARP (glycoprotein A repetitions predominant).

The present invention thus aims at providing a new strategy for targeting Treg based on an anti-GARP protein inhibiting TGF-β signaling.

SUMMARY

One object of the invention is a protein binding to Glycoprotein A repetitions predominant (GARP) in the presence of TGF-β. In an embodiment, said protein binds to GARP only in the presence of TGF-β. In another embodiment, said protein binds to GARP when GARP is complexed to TGF-β. In another embodiment, said protein binds to a complex of GARP and TGF-β.

In an embodiment of the invention, said protein is an antibody molecule selected from the group consisting of a whole antibody, a humanized antibody, a single chain antibody, a dimeric single chain antibody, a Fv, a Fab, a F(ab)'2, a defucosylated antibody, a bi-specific antibody, a diabody, a triabody, a tetrabody.

In another embodiment, said protein is an antibody fragment selected from the group consisting of a unibody, a domain antibody, and a nanobody.

In another embodiment, said protein is an antibody mimetic selected from the group consisting of an affibody, an affilin, an affitin, an adnectin, an atrimer, an evasin, a DARPin, an anticalin, an avimer, a fynomer, a versabody and a duocalin.

Another object of the invention is a protein as described here above or a protein binding GARP and inhibiting TGF-β signaling.

In embodiment, said protein is an antibody or antigen binding fragment thereof that binds to a conformational epitope comprising one or more amino acids of GARP or an epitope of GARP modified as a result of GARP being complexed with latent TGF-β.

In another embodiment, said antibody or antigen binding fragment thereof further binds one or more amino acids of latent TGF-β. In another embodiment, said antibody or antigen binding fragment thereof binds an epitope comprising one or more residues from 101 to 141 residues of GARP as set forth in SEQ ID NO: 1.

Another object of the invention is a protein having the variable region of the heavy chain comprising at least one of the following CDRs:

```
                                      (SEQ ID NO: 2)
VH-CDR1:        GFSLTGYGIN
or (SEQ ID NO: 52)
                GYGIN;

(SEQ ID NO: 3)
VH-CDR2:        MIWSDGSTDYNSVLTS;
and (SEQ ID NO: 4)
VH-CDR3:        DRNYYDYDGAMDY,
``` or any CDR having an amino acid sequence that shares at least 60% of identity with SEQ ID NO: 2-4 or 52,
or having the variable region of the light chain comprising at least one of the following CDRs:

```
                                      (SEQ ID NO: 5)
VL-CDR1: KASDHIKNWLA;

(SEQ ID NO: 6)
VL-CDR2: GATSLEA;
and (SEQ ID NO: 7)
VL-CDR3: QQYWSTPWT,
``` or any CDR having an amino acid sequence that shares at least 60% of identity with SEQ ID NO: 5-7;
or the variable region of the heavy chain comprises at least one of the following CDRs:

```
                                      (SEQ ID NO: 13)
VH-CDR1: SYYID;

(SEQ ID NO: 14)
VH-CDR2: RIDPEDGGTKYAQKFQG;
or (SEQ ID NO: 15)
VH-CDR3: NEWETVVVGDLMYEYEY,
``` or any CDR having an amino acid sequence that shares at least 60% of identity with SEQ ID NO: 13-15;
or wherein the variable region of the light chain comprises at least one of the following CDRs:
VL-CDR1: QASQX$_1$IX$_2$SX$_3$LA (SEQ ID NO: 16), wherein X$_1$ is S or T, X$_2$ is S or V, X$_3$ is Y or F;
VL-CDR2: X$_1$X$_2$SX$_3$X$_4$X$_5$T (SEQ ID NO: 17), wherein X$_1$ is G or R; X$_2$ is A or T; X$_3$ is R or I; X$_4$ is L or P; X$_5$ is Q or K;
VL-CDR3: QQYX$_1$SX$_2$PX$_3$T, wherein X$_1$ is D, A, Y or V; X$_2$ is A, L or V; X$_3$ is V or P (SEQ ID NO: 18);
or any CDR having an amino acid sequence that shares at least 60% of identity with SEQ ID NO: 16-18.

In an embodiment, the variable region of the heavy chain comprises at least one of the following CDRs:

```
                                      (SEQ ID NO: 2)
VH-CDR1:        GFSLTGYGIN
or (SEQ ID NO: 52)
                GYGIN;

(SEQ ID NO: 3)
VH-CDR2:        MIWSDGSTDYNSVLTS;
and (SEQ ID NO: 4)
VH-CDR3:        DRNYYDYDGAMDY,
``` or any CDR having an amino acid sequence that shares at least 60% of identity with SEQ ID NO: 2-4 or 52,
and the variable region of the light chain comprises at least one of the following CDRs:

```
                                      (SEQ ID NO: 5)
VL-CDR1: KASDHIKNWLA;

(SEQ ID NO: 6)
VL-CDR2: GATSLEA;
and (SEQ ID NO: 7)
VL-CDR3: QQYWSTPWT,
``` or any CDR having an amino acid sequence that shares at least 60% of identity with SEQ ID NO: 5-7;
or the variable region of the heavy chain comprises at least one of the following CDRs:

```
                                      (SEQ ID NO: 13)
VH-CDR1: SYYID;

(SEQ ID NO: 14)
VH-CDR2: RIDPEDGGTKYAQKFQG;
or (SEQ ID NO: 15)
VH-CDR3: NEWETVVVGDLMYEYEY;
``` or any CDR having an amino acid sequence that shares at least 60% of identity with SEQ ID NO: 13-15,
and the variable region of the light chain comprises at least one of the following CDRs:
VL-CDR1: QASQX$_1$IX$_2$SX$_3$LA (SEQ ID NO: 16), wherein X$_1$ is S or T, X$_2$ is S or V, X$_3$ is Y or F;
VL-CDR2: X$_1$X$_2$SX$_3$X$_4$X$_5$T (SEQ ID NO: 17), wherein X$_1$ is G or R; X$_2$ is A or T; X$_3$ is R or I; X$_4$ is L or P; X$_5$ is Q or K;
VL-CDR3: QQYX$_1$SX$_2$PX$_3$T, wherein X$_1$ is D, A, Y or V; X$_2$ is A, L or V; X$_3$ is V or P (SEQ ID NO: 18);
or any CDR having an amino acid sequence that shares at least 60% of identity with SEQ ID NO: 16-18.

In another embodiment, the variable region of the heavy chain comprises the following CDRs: GFSLTGYGIN (SEQ ID NO: 2), MIWSDGSTDYNSVLTS (SEQ ID NO: 3), DRNYYDYDGAMDY (SEQ ID NO: 4) and the variable region of the light chain comprises the following CDRs: KASDHIKNWLA (SEQ ID NO: 5), GATSLEA (SEQ ID NO: 6), QQYWSTPWT (SEQ ID NO: 7) or any CDR having an amino acid sequence that shares at least 60% of identity with said SEQ ID NO: 2-7;
or the variable region of the heavy chain comprises the following CDRs: GYGIN (SEQ ID NO: 52), MIWSDGST- DYNSVLTS (SEQ ID NO: 3), DRNYYDYDGAMDY (SEQ ID NO: 4) and the variable region of the light chain comprises the following CDRs: KASDHIKNWLA (SEQ ID NO: 5), GATSLEA (SEQ ID NO: 6), QQYWSTPWT (SEQ ID NO: 7) or any CDR having an amino acid sequence that shares at least 60% of identity with said SEQ ID NO: 52 and 3-7;
or wherein the variable region of the heavy chain comprises the following CDRs: SYYID (SEQ ID NO: 13), RIDPEDGGTKYAQKFQG (SEQ ID NO: 14), or NEWETVVVGDLMYEYEY (SEQ ID NO: 15); and the variable region of the light chain comprises the following CDRs: QASQX$_1$IX$_2$SX$_3$LA (SEQ ID NO: 16), wherein X$_1$ is S or T, X$_2$ is S or V, X$_3$ is Y or F; X$_1$X$_2$SX$_3$X$_4$X$_5$T (SEQ ID NO: 17), wherein X$_1$ is G or R; X$_2$ is A or T; X$_3$ is R or I; X$_4$ is L or P; X$_5$ is Q or K; QQYX$_1$SX$_2$PX$_3$T, wherein X$_1$ is D, A, Y or V; X$_2$ is A, L or V; X$_3$ is V or P (SEQ ID NO: 18); or any CDR having an amino acid sequence that shares at least 60% of identity with said SEQ ID NO: 16-18.

In another embodiment, the amino acid sequence of the heavy chain variable region is SEQ ID NO: 8 or SEQ ID NO: 50 and the amino acid sequence of the light chain variable region is SEQ ID NO: 9 or SEQ ID NO: 51, or the amino acid sequence of the heavy chain variable region is SEQ ID NO: 34 and the amino acid sequence of the light chain variable region is one of SEQ ID NO: 35-39 or any sequence having an amino acid sequence that shares at least 60% of identity with said SEQ ID NO: 8-9, 50-51 or 34-39.

Another object of the invention is a protein as defined here above binding to an epitope on the polypeptide having the amino acid sequence SEQ ID No: 1 recognized by an antibody comprising a heavy chain variable region as set forth in SEQ ID NO: 8 or in SEQ ID NO: 50 and a light chain variable region as set forth in SEQ ID NO: 9 or in SEQ ID NO: 51, or by an antibody comprising a heavy chain variable region as set forth in SEQ ID NO: 34 and one of the light chain variable region as set forth in SEQ ID NO: 35-39.

Another object of the invention is an antibody or antigen binding fragment produced by a hybridoma registered under the accession number LMBP 10246CB on May 30, 2013.

Another object of the invention is a polynucleotide sequence encoding the antibody or antigen binding fragment as described here above.

Another object of the invention is an expression vector comprising the polynucleotide according to claim as described here above.

Another object of the invention is a hybridoma cell line producing an antibody against GARP registered under the accession number LMBP 10246CB on May 30, 2013.

Another object of the invention is a pharmaceutical composition comprising the protein as described here above and a pharmaceutically acceptable excipient.

Another object of the invention is a pharmaceutical composition as described here above for treating a TGF-β related disorder in a subject in need thereof. In an embodiment, the TGF-β related disorder is selected from the group consisting of inflammatory diseases, chronic infection, cancer, fibrosis, cardiovascular diseases, cerebrovascular disease (e.g. ischemic stroke), and neurodegenerative diseases.

In another embodiment, the pharmaceutical composition as described here above is to be administered in combination with another treatment for cancer or another immunotherapeutic agent such as a tumor vaccine or an immunostimulatory antibody. In another embodiment, the pharmaceutical composition as described here above is to be administered as an immunostimulatory antibody for treatment of cancer patients.

Definitions

In the present invention, the following terms have the following meanings:

"Antibody" or "Immunoglobulin"—As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. human GARP). The term "GARP antibodies" is used herein to refer to antibodies which exhibit immunological specificity for human GARP protein. As explained elsewhere herein, "specificity" for human GARP does not exclude cross-reaction with species homologues of GARP. In addition, it also does not exclude antibodies recognising an epitope spanning GARP protein residues and TGF-β protein residue. Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000 Daltons. The four chains are joined by disulfide bonds in a "Y" configuration wherein the light chains bracket the heavy chains starting at the mouth of the "Y" and continuing through the variable region. The light chains of an antibody are classified as either kappa or lambda ([κ], [λ]). Each heavy chain class may be bonded with either a kappa or lambda light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementarity determining regions (CDRs) on each of the VH and VL chains.

"An isolated antibody"—As used herein, an "isolated antibody" is one that has been separated and/or recovered from a component of its natural environment. Contaminant components of its natural environment are materials that would interfere with diagnostic or therapeutic uses of the antibody, and may include enzymes, hormones, and other proteinaceous or non proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

"Affinity variants"—As used herein, the term "affinity variant" refers to a variant antibody which exhibits one or more changes in amino acid sequence compared to a reference GARP antibody, wherein the affinity variant exhibits an altered affinity for the human GARP protein or GARP/TGF-β complex in comparison to the reference antibody. Typically, affinity variants will exhibit an improved affinity for human GARP or human GARP/TGF-β complex, as compared to the reference GARP antibody. The improvement may be either a lower KD, for human GARP, or a faster off-rate for human GARP or an alteration in the pattern of cross-reactivity with non-human GARP homologues. Affinity variants typically exhibit one or more changes in amino acid sequence in the CDRs, as compared to the reference GARP antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"Binding Site"—As used herein, the term "binding site" comprises a region of a polypeptide which is responsible for selectively binding to a target antigen of interest (e.g. human GARP). Binding domains or binding regions comprise at least one binding site. Exemplary binding domains include an antibody variable domain. The antibody molecules of the invention may comprise a single antigen binding site or multiple (e.g., two, three or four) antigen binding sites.

"Conservative amino acid substitution"—As used herein, a "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

"Chimeric"—As used herein, a "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric GARP antibodies include fusion proteins comprising camelid-derived VH and VL domains, or humanised variants thereof, fused to the constant domains of a human antibody, e.g. human IgG1, IgG2, IgG3 or IgG4.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | CDR definitions | | |
|---|---|---|---|
| | Kabat (1) | Chothia (2) | MacCallum (3) |
| VH CDR1 | 31-35 | 26-32 | 30-35 |
| VH CDR2 | 50-65 | 53-55 | 47-58 |
| VH CDR3 | 95-102 | 96-101 | 93-101 |
| VL CDR1 | 24-34 | 26-32 | 30-36 |
| VL CDR2 | 50-56 | 50-52 | 46-55 |
| VL CDR3 | 89-97 | 91-96 | 89-96 |

(1) Residue numbering follows the nomenclature of Kabat et al., supra
(2) Residue numbering follows the nomenclature of Chothia et al., supra
(3) Residue numbering follows the nomenclature of MacCallum et al., supra "CH2 domain"—As used herein the term "CH2 domain" includes the region of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

"Camelid-Derived"—In certain preferred embodiments, the GARP antibody molecules of the invention comprise framework amino acid sequences and/or CDR amino acid sequences derived from a camelid conventional antibody raised by active immunization of a camelid with GARP antigen. However, GARP antibodies comprising camelid-derived amino acid sequences may be engineered to comprise framework and/or constant region sequences derived from a human amino acid sequence or other non-camelid mammalian species. For example, a human or non-human primate framework region, heavy chain region, and/or hinge region may be included in the subject GARP antibodies. In an embodiment, one or more non-camelid amino acids may be present in the framework region of a "camelid-derived" GARP antibody, e.g., a camelid framework amino acid sequence may comprise one or more amino acid mutations in which the corresponding human or non-human primate amino acid residue is present. Moreover, camelid-derived VH and VL domains, or humanized variants thereof, may be linked to the constant domains of human antibodies to produce a chimeric molecule, as extensively described elsewhere herein.

"Derived From"—As used herein the term "derived from" a designated protein (e.g. a GARP antibody or antigen-binding fragment thereof) refers to the origin of the polypeptide. In an embodiment, the polypeptide or amino acid sequence which is derived from a particular starting polypeptide is a CDR sequence or sequence related thereto. In an embodiment, the amino acid sequence which is derived from a particular starting polypeptide is not contiguous. For example, in an embodiment, one, two, three, four, five, or six CDRs are derived from a starting antibody. In an embodiment, the polypeptide or amino acid sequence which is derived from a particular starting polypeptide or amino acid sequence has an amino acid sequence that is essentially identical to that of the starting sequence, or a region thereof wherein the region consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence. In an embodiment, the one or more CDR sequences derived from the starting antibody are altered to produce variant CDR sequences, e.g. affinity variants, wherein the variant CDR sequences maintain GARP binding activity.

"Diabodies"—As used herein, the term "diabodies" refers to small antibody fragments prepared by constructing sFv fragments (see sFv paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Holliger et al., Proc. Natl. Acad. Sci., 90:6444-6448 (1993).

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Epitope"—As used herein, the term "epitope" refers to a specific arrangement of amino acids located on a peptide or protein or proteins to which an antibody binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

"Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat. In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a [beta]-sheet conformation and the CDRs form loops which connect, and in some cases form part of, the [beta]-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Fragment"—As used herein, the term "fragment" refers to a part or region of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to human GARP). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, diabodies or any antigen-binding molecule formed by combination, assembly or conjugation of such antigen binding fragments. Fragments can be obtained, e.g., via chemical or enzymatic treatment of an intact or complete antibody or antibody chain or by recombinant means.

"Fv"—As used herein, the term "Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region"—As used herein, the term "heavy chain region" includes amino acid sequences derived from the constant domains of an immunoglobulin heavy chain. A polypeptide comprising a heavy chain region comprises at least one of: a CH1 domain, a hinge (e.g., upper, middle, and/or lower hinge region) domain, a CH2 domain, a CH3 domain, or a variant or fragment thereof. In an embodiment, a binding molecule of the invention may comprise the Fc region of an immunoglobulin heavy chain (e.g., a hinge portion, a CH2 domain, and a CH3 domain). In another embodiment, a binding molecule of the invention lacks at least a region of a constant domain (e.g., all or part of a CH2 domain). In certain embodiments, at least one, and preferably all, of the constant domains are derived from a human immunoglobulin heavy chain. For example, in one preferred embodiment, the heavy chain region comprises a fully human hinge domain. In other preferred embodiments, the heavy chain region comprising a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a polypeptide may comprise a CH2 domain derived from an IgG1 molecule and a hinge region derived from an IgG3 or IgG4 molecule. In other embodiments, the constant domains are chimeric domains comprising regions of different immunoglobulin molecules. For example, a hinge may comprise a first region from an IgG1 molecule and a second region from an IgG3 or IgG4 molecule. As set forth above, it will be understood by one of ordinary skill in the art that the constant domains of the heavy chain region may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region"—As used herein, the term "hinge region" includes the region of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains. The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated. The more highly conserved regions of variable domains are called the framework region (FR), as defined below. The variable domains of native heavy and light chains each comprise four FRs (FR1, FR2, FR3 and FR4, respectively), largely adopting a [beta]-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215: 175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"Humanising substitutions"—As used herein, the term "humanising substitutions" refers to amino acid substitutions in which the amino acid residue present at a particular position in the VH or VL domain antibody GARP antibody (for example a camelid-derived GARP antibody) is replaced with an amino acid residue which occurs at an equivalent position in a reference human VH or VL domain. The reference human VH or VL domain may be a VH or VL domain encoded by the human germline, in which case the substituted residues may be referred to as "germlining substitutions". Humanising/germlining substitutions may be made in the framework regions and/or the CDRs of a GARP antibody, defined herein.

"High human homology"—An antibody comprising a heavy chain variable domain (VH) and a light chain variable domain (VL) will be considered as having high human homology if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity human germline sequences, including for example antibodies comprising VH and VL domains of camelid conventional antibodies, as well as engineered, especially humanized, variants of such antibodies and also "fully human" antibodies. In an embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%. In an embodiment the VH domain of the antibody with high human homology may contain one or more (e.g. 1 to 10) amino acid sequence mis-matches across the framework regions FR1, FR2, FR3 and FR4, in comparison to the closest matched human VH sequence. In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In an embodiment the VL domain of the antibody with high human homology may contain one or more (e.g. 1 to 10) amino acid sequence mis-matches across the framework regions FR1, FR2, FR3 and FR4, in comparison to the closest matched human VL sequence. Before analyzing the percentage sequence identity between the antibody with high human homology and human germline VH and VL, the canonical folds may be determined, which allow the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a data file. In these data files, the key residue positions are shown with the allowed amino acids at each position. The sequence of the variable region of the antibody of interest is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)). With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines). To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions. Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., NAR 27: 209-212 (1999); http://im.gt.cines.fr). Antibodies with high human homology may comprise hypervariable loops or CDRs having human or human-like canonical folds, as discussed in detail below. In an embodiment at least one hypervariable loop or CDR in either the VH domain or the VL domain of the antibody with high human homology may be obtained or derived from a VH or VL domain of a non-human antibody, for example a conventional antibody from a species of Camelidae, yet exhibit a predicted or actual canonical fold structure which is substantially identical to a canonical fold structure which occurs in human antibodies. It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196: 901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone. The predicted canonical fold structures for the hypervariable loops of any given VH or VL sequence in an antibody with high human homology can be analysed using algorithms which are publicly available from www.bioinf.org.uk/abs/chothia.html, www.biochem.ucl.ac.uk/~martin/antibodies-.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence. In the case of the VH domain, H1 and H2 loops may be scored as having a canonical fold structure "substantially identical" to a canonical fold structure known to occur in human antibodies if at least the first, and preferable both, of the following criteria are fulfilled:

1. An identical length, determined by the number of residues, to the closest matching human canonical structural class.

2. At least 33% identity, preferably at least 50% identity with the key amino acid residues described for the corresponding human H1 and H2 canonical structural classes (note for the purposes of the foregoing analysis the H1 and H2 loops are treated separately and each compared against its closest matching human canonical structural class). The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the H1 and H2 loops in the antibody of interest matches the structure of a human canonical fold. Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline. In an embodiment, both HI and H2 in the VH domain of the antibody with high human homology exhibit a predicted or actual canonical fold structure which is substantially identical to a canonical fold structure which occurs in human antibodies. Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a Camelidae species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a Camelidae species, and form one of the following canonical fold combinations: 1-1, 1-2, 1-3, 1-6, 1-4, 2-1, 3-1 and 3-5. An antibody with high human homology may contain a VH domain which exhibits both high sequence identity/sequence homology with human VH, and which contains hypervariable loops exhibiting structural homology with human VH. It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains. Thus, in an embodiment the VH domain of the GARP antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a Camelidae species), but form a combination of predicted or actual canonical fold structures which is the same as a canonical fold combination known to occur naturally in the same human VH domain. In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies. As with the VH domains, the hypervariable loops of VL domains of both VLambda and VKappa types can adopt a limited number of conformations or canonical structures, determined in part by length and also by the presence of key amino acid residues at certain canonical positions. Within an antibody of interest having high human homology, L1, L2 and L3 loops obtained from a VL domain of a non-human species, e.g. a Camelidae species, may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.

2. At least 33% identity, preferably at least 50% identity with the key amino acid residues described for the corresponding human L1 or L2 canonical structural classes, from either the VLambda or the VKappa repertoire (note for the purposes of the foregoing analysis the L1 and L2 loops are treated separately and each compared against its closest matching human canonical structural class). The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by +1 or +2 amino acids) but the actual structure of the Camelidae loops matches a human canonical fold. Key amino acid residues found in the human canonical structural classes for the CDRs of human VLambda and VKappa domains are described by Morea et al. Methods, 20:

267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference. L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html).

In a further embodiment, all three of L1, L2 and L3 in the VL domain of an antibody with high human homology may exhibit a substantially human structure. It is preferred that the VL domain of the antibody with high human homology exhibit both high sequence identity/sequence homology with human VL, and also that the hypervariable loops in the VL domain exhibit structural homology with human VL.

In an embodiment, the VL domain of the GARP antibody with high human homology may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain. It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g. camelid-derived VH/VL pairings) with maximal sequence and structural homology to human-encoded VH/VL pairings.

"Immunospecific", "specific for" or to "specifically bind"—As used herein, an antibody is said to be "immunospecific", "specific for" or to "specifically bind" an antigen if it reacts at a detectable level with the antigen, preferably with an affinity constant, Ka, of greater than or equal to about $10^4$ $M^{-1}$, or greater than or equal to about $10^5$ $M^{-1}$, greater than or equal to about $10^6 M^{-1}$, greater than or equal to about $10^7 M^{-1}$, or greater than or equal to $10^8$ $M^{-1}$, or greater than or equal to $10^9$ $M^{-1}$, or greater than or equal to $10^{10}$ $M^{-1}$. Affinity of an antibody for its cognate antigen is also commonly expressed as a dissociation constant Kd, and in certain embodiments, an antibody specifically binds to antigen if it binds with a Kd of less than or equal to $10^{-4}$ M, less than or equal to about $10^{-5}$ M, less than or equal to about $10^{-6}$ M, less than or equal to $10^{-7}$ M, or less than or equal to $10^{-8}$ M, or less than or equal to $5 \cdot 10^{-9}$ M, or less than or equal to $10^{-9}$ M, or less than or equal to $5 \cdot 10^{-10}$ M, or less than or equal to $10^{-10}$ M. Affinities of antibodies can be readily determined using conventional techniques, for example, those described by Scatchard G et al. (The attractions of proteins for small molecules and ions. Ann NY Acad Sci 1949; 51:660-672). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

"Isolated nucleic acid"—As used herein, is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man. The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylation, acetylation, phosphorylation and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen. An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining. Isolated polypeptide includes the polypeptide in situ within recombinant cells since at least one component of the polypeptide's natural environment will not be present. Ordinarily, however, isolated polypeptide will be prepared by at least one purification step.

"Identity" or "identical"—As used herein, the term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

"Modified antibody"—As used herein, the term "modified antibody" includes synthetic forms of antibodies which are altered such that they are not naturally occurring, e.g., antibodies that comprise at least two heavy chain regions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain region lacking a CH2 domain and comprising a binding domain of a polypeptide comprising the binding region of one member of a receptor ligand pair.

"Mammal"—As used herein, the term "mammal" refers to any mammal, including humans, domestic and farm animals, and zoo, sports, or pet animals, such as dogs, cats, cattle, horses, sheep, pigs, goats, rabbits, etc. Preferably, the mammal is human.

"Monoclonal antibody"—As used herein, the term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

"Native sequence"—As used herein, the term "native sequence" refers to a polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means. A polynucleotide "variant", as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art. A polypeptide "variant", as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or region of a polypeptide of the invention, one skilled in the art will typically change one or more of the codons of the encoding DNA sequence. For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and of course, its underlying DNA coding sequence, and nevertheless obtain a protein with similar properties. It is thus contemplated that various changes may be made in the peptide sequences of the disclosed compositions, or corresponding DNA sequences that encode said peptides without appreciable loss of their biological utility or activity. In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take several of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

"Pharmaceutically acceptable excipient"—As used herein, the term "pharmaceutically acceptable excipient" includes any and all solvents, dispersion media, coatings, antibacterial and antifungal agents, isotonic and absorption delaying agents and the like. Said excipient does not produce an adverse, allergic or other untoward reaction when administered to an animal, preferably a human. For human administration, preparations should meet sterility, pyrogenicity, and general safety and purity standards as required by FDA Office of Biologics standards.

"Specificity"—As used herein, the term "specificity" refers to the ability to specifically bind (e.g., immunoreact with) a given target, e.g., GARP. A polypeptide may be monospecific and contain one or more binding sites which specifically bind a target, or a polypeptide may be multi-specific and contain two or more binding sites which specifically bind the same or different targets. In an embodiment, an antibody of the invention is specific for more than one target. For example, in an embodiment, a multispecific binding molecule of the invention binds to GARP and a second molecule expressed on a tumor cell. Exemplary antibodies which comprise antigen binding sites that bind to antigens expressed on tumor cells are known in the art and one or more CDRs from such antibodies can be included in an antibody of the invention.

"Synthetic"—As used herein the term "synthetic" with respect to polypeptides includes polypeptides which comprise an amino acid sequence that is not naturally occurring. For example, non-naturally occurring polypeptides are modified forms of naturally occurring polypeptides (e.g., comprising a mutation such as an addition, substitution or deletion) or polypeptides which comprise a first amino acid sequence (which may or may not be naturally occurring) that is linked in a linear sequence of amino acids to a second amino acid sequence (which may or may not be naturally occurring) to which it is not naturally linked in nature.

"Single-chain Fv" also abbreviated as "sFv" or "scFv"—As used herein, the terms "Single-chain Fv", "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

"Variable region" or "variable domain"—As used herein, the term "variable" refers to the fact that certain regions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1 (λ), L2 (λ) and L3 (λ) and may be defined as comprising residues 24-33 (L1(λ), consisting of 9, 10 or 11 amino acid residues), 49-53 L2 (λ), consisting of 3 residues) and 90-96 (L3(λ), consisting of 6 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (HI, consisting of 7, 8 or 9 residues), 52-56 (H2, consisting of 3 or 4 residues) and 91-105 (H3, highly variable in length) in the VH domain (Morea et al., Methods 20:267-279 (2000)). Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including [gamma], [epsilon], [delta], a or [mu]. The hypervariable loops L1, L2, L3, H1, H2 and H3 may each comprise part of a "complementarity determining region" or "CDR", as defined below.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules preferably have at least one binding site specific for a human GARP molecule. In particular embodiments the GARP antibodies provided herein may be at least bivalent.

"Treating" or "treatment" or "alleviation"—As used herein, the terms "treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

"TGF-β"—As used herein, the term TGF-β refers to the three isoforms named TGF-β1, TGF-β2 and TGF-β3. The peptide structures of the TGF-β isoforms are highly similar (homologies on the order of 70-80%). They are all encoded as large protein precursors; TGF-β1 (GenBank Access No: NM_000660 contains 390 amino acids and TGF-β2 (GenBank Access No: NM_001135599 and NM_003238) and TGF-β3 (GenBank Access No: XM_005268028) each contain 412 amino acids. They each have an N-terminal signal peptide of 20-30 amino acids that they require for secretion from a cell, a pro-region (named latency associated peptide or LAP), and a 112-114 amino acid C-terminal region that becomes the mature TGF-β molecule following its release from the pro-region by proteolytic cleavage.

DETAILED DESCRIPTION

One object of the invention is a protein binding to GARP in the presence of TGF-β. Another object of the invention is a protein comprising an antigen binding domain, wherein the antigen binding domain binds specifically to GARP in the presence of TGF-β.

In an embodiment, said protein binds to GARP only in the presence of TGF-β.

GARP is also called Leucin Rich Repeat Containing 32 (LRRC32) and belongs to the Leucin Rich Repeat family. The complete amino acid sequence of the human GARP protein transcript variant 2 of the present invention (SEQ ID NO: 1) (GenBank Accession NM_001128922) is:

```
MRPQILLLLALLTLGLAAQHQDKVPCKMVDKKVSCQVLGLLQVPSVLPPD

TETLDLSGNQLRSILASPLGFYTALRHLDLSTNEISFLQPGAFQALTHLE

HLSLAHNRLAMATALSAGGLGPLPRVTSLDLSGNSLYSGLLERLLGEAPS

LHTLSLAENSLTRLTRHTFRDMPALEQLDLHSNVLMDIEDGAFEGLPRLT

HLNLSRNSLTCISDFSLQQLRVLDLSCNSIEAFQTASQPQAEFQLTWLDL

RENKLLHFPDLAALPRLIYLNLSNNLIRLPTGPPQDSKGIHAPSEGWSAL

PLSAPSGNASGRPLSQLLNLDLSYNEIELIPDSFLEHLTSLCFLNLSRNC

LRTFEARRLGSLPCLMLLDLSHNALETLELGARALGSLRTLLLQGNALRD

LPPYTFANLASLQRLNLQGNRVSPCGGPDEPGPSGCVAFSGITSLRSLSL

VDNEIELLRAGAFLHTPLTELDLSSNPGLEVATGALGGLEASLEVLALQG

NGLMVLQVDLPCFICLKRLNLAENRLSHLPAWTQAVSLEVLDLRNNSFSL

LPGSAMGGLETSLRRLYLQGNPLSCCGNGWLAAQLHQGRVDVDATQDLIC

RFSSQEEVSLSHVRPEDCEKGGLKNINLIIILTFILVSAILLTTLAACCC

VRRQKFNQQYKA.
```

In an embodiment, the protein of the invention binds to GARP when GARP is complexed to TGF-β.

In another embodiment, the protein of the invention binds to GARP when GARP is complexed to latent TGF-β.

In another embodiment, the protein of the invention binds to a complex of GARP and TGF-β.

In an embodiment, the protein of the invention binds to a complex of GARP and TGF-β1; TGF-β2, isoform 1; TGF-β2, isoform 2; TGF-β3. Preferably, the protein of the invention binds to a complex of GARP and TGF-β1.

In another embodiment, the protein of the invention binds to a complex of GARP and latent TGF-β.

The term "latent TGF-β" as used herein comprises a complex whose C-terminal fragment, or mature TGF-β1, remains non-covalently bound to the N-terminal fragment known as LAP.

In another embodiment, the protein of the invention binds to a complex of GARP and latent TGF-β at a KD (the equilibrium dissociation constant between the antibody and its antigen) of less than $10^{-10}$ M.

In an embodiment, said protein is an antibody molecule selected from the group consisting of a whole antibody, a humanized antibody, a single chain antibody, a dimeric single chain antibody, a Fv, a Fab, a F(ab)'2, a defucosylated antibody, a bi-specific antibody, a diabody, a triabody, a tetrabody.

In another embodiment, said protein is an antibody fragment selected from the group consisting of a unibody, a domain antibody, and a nanobody.

In another embodiment, said protein is an antibody mimetic selected from the group consisting of an affibody, an affilin, an affitin, an adnectin, an atrimer, an evasin, a DARPin, an anticalin, an avimer, a fynomer, a versabody and a duocalin.

A domain antibody is well known in the art and refers to the smallest functional binding units of antibodies, corresponding to the variable regions of either the heavy or light chains of antibodies.

A nanobody is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3).

A unibody is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

An affibody is well known in the art and refers to affinity proteins based on a 58 amino acid residue protein domain, derived from one of the IgG binding domain of staphylococcal protein A.

DARPins (Designed Ankyrin Repeat Proteins) are well known in the art and refer to an antibody mimetic DRP (designed repeat protein) technology developed to exploit the binding abilities of non-antibody polypeptides.

Anticalins are well known in the art and refer to another antibody mimetic technology, wherein the binding specificity is derived from lipocalins. Anticalins may also be formatted as dual targeting protein, called Duocalins.

Avimers are well known in the art and refer to another antibody mimetic technology. Versabodies are well known in the art and refer to another antibody mimetic technology. They are small proteins of 3-5 kDa with >15% cysteines, which form a high disulfide density scaffold, replacing the hydrophobic core the typical proteins have.

In another embodiment, said protein is an immunoconjugate comprising an antibody or fragment thereof conjugated to a therapeutic agent.

In another embodiment, said protein is a conjugate comprising the protein of the invention conjugated to an imaging agent. Said protein could be used for example for imaging applications.

Another object of the invention is a protein that binds to GARP and inhibits TGF-β signaling.

In an embodiment, said protein binds to GARP when GARP is complexed to TGF-β.

In another embodiment, said protein binds to GARP when GARP is complexed to latent TGF-β.

In another embodiment, said protein binds to a complex of GARP and TGF-β.

In another embodiment, said protein binds to a complex of GARP and latent TGF-β.

In an embodiment, said protein is an antibody molecule selected from the group consisting of a whole antibody, a humanized antibody, a single chain antibody, a dimeric single chain antibody, a Fv, a Fab, a F(ab)'2, a defucosylated antibody, a bi-specific antibody, a diabody, a triabody, a tetrabody.

In another embodiment, said protein is an antibody fragment selected from the group consisting of a unibody, a domain antibody, and a nanobody.

In another embodiment, said protein is an antibody mimetic selected from the group consisting of an affibody, an affilin, an affitin, an adnectin, an atrimer, an evasin, a DARPin, an anticalin, an avimer, a fynomer, a versabody and a duocalin.

In an embodiment, said protein is an anti-hGARP (anti human GARP) antibody or antigen binding fragment thereof that inhibits TGF-β signaling.

In an embodiment, said protein prevents or inhibits active TGF-β to be released or inhibits the release of mature TGF-β from Tregs.

In another embodiment, said protein inhibits or prevents mature TGF-β to bind to TGF-β receptors.

In another embodiment, said protein inhibits TGF-β activity and/or the activation of molecules from the TGF-β receptor signaling pathway.

As used herein, the term "inhibit" means that the protein is capable of blocking, reducing, preventing or neutralizing TGF-β signaling or the release of mature TGF-β from Tregs or the binding of mature TGF-β to TGF-β receptors or TGF-β activity and/or the activation of molecules from the TGF-β receptor signaling pathway.

In an embodiment, said protein is a monoclonal antibody.

In another embodiment, said protein is a polyclonal antibody.

In another embodiment, said protein binds to a conformational epitope.

In another embodiment, said conformational epitope comprises one or more amino acids of hGARP.

In another embodiment, said conformational epitope comprises an epitope of GARP modified as a result of GARP being complexed with latent TGF-β. In another embodiment, said conformational epitope comprises amino acids of hGARP and amino acids of latent TGF-β.

In another embodiment, said conformational epitope is a mixed conformational epitope and comprises amino acids from both GARP and TGF-β.

In another embodiment, said conformational epitope is a binding-induced conformational epitope and comprises amino acids from GARP only, but that adopts a different conformation in the presence of TGF-β.

In an embodiment, said epitope comprises one or more residues from 101 to 141 residues of hGARP amino acid sequence (SEQ ID NO: 1).

These 101 to 141 residues are as set forth in SEQ ID NO: 12:

```
HLSLAHNRLAMATALSAGGLGPLPRVTSLDLSGNSLYSGLL.
```

In another embodiment of the invention, said epitope comprises the residues 137, 138 and 139: YSG of hGARP amino acid sequence (SEQ ID NO: 1).

In another embodiment of the invention, said epitope comprises the residues 137, 138 and 139: YSG of hGARP amino acid sequence (SEQ ID NO: 1) and requires the presence of TGF-β.

In another embodiment of the invention, said epitope comprises the residues 137, 138 and 139: YSG of hGARP amino acid sequence (SEQ ID NO: 1) and 1, 2, 3, 4, 5, 6, 7, 8, 9, 10, 11, 12, 13, 14, 15, 16, 17, 18, 19, 20 contiguous residues in N-terminal and/or C-terminal of the residues 137, 138 and 139: YSG of SEQ ID NO: 1.

In another embodiment of the invention, said epitope comprises the residues 137, 138 and 139: YSG of hGARP amino acid sequence (SEQ ID NO: 1) and 1, 2, 3, 4, 5, 6, 7, 8, 9, 10, 11, 12, 13, 14, 15, 16, 17, 18, 19, 20 contiguous residues in N-terminal and/or C-terminal of the residues 137, 138 and 139: YSG of SEQ ID NO: 1, and requires the presence of TGF-β.

In an embodiment of the invention, the protein of the invention binds to epitopes preferably within the region 101-141 of hGARP and inhibits the release of latent TGF-β from GARP.

One skilled in the art can determine the ability of a protein to inhibit TGF-β signaling by measuring for example activation of molecules from the TGF-β receptor signaling pathway. One example of such test is typically the measure of the phosphorylation of SMAD2 (as shown in Example 2 of the present invention).

An object of the invention is an antibody against human GARP or antigen binding fragment thereof wherein the variable region of the heavy chain comprises at least one of the followings CDRs:

```
                                        (SEQ ID NO: 2)
VH-CDR1:    GFSLTGYGIN
or
                                        (SEQ ID NO: 52)
            GYGIN;

(SEQ ID NO: 3)
VH-CDR2:    MIWSDGSTDYNSVLTS;
and (SEQ ID NO: 4)
VH-CDR3:    DRNYYDYDGAMDY.
```

Another object of the invention is an anti-hGARP antibody or antigen binding fragment thereof wherein the variable region of the light chain comprises at least one of the followings CDRs:

```
                                        (SEQ ID NO: 5)
VL-CDR1:  KASDHIKNWLA;

(SEQ ID NO: 6)
VL-CDR2:  GATSLEA;
and (SEQ ID NO: 7)
VL-CDR3:  QQYWSTPWT.
```

Another object of the invention is an antibody against human GARP or antigen binding fragment thereof wherein the variable region of the heavy chain comprises at least one of the followings CDRs:

```
                                            (SEQ ID NO: 13)
    VH-CDR1: SYYID;

(SEQ ID NO: 14)
    VH-CDR2: RIDPEDGGTKYAQKFQG;
    and (SEQ ID NO: 15)
    VH-CDR3: NEWETVVVGDLMYEYEY.
```

Another object of the invention is an anti-hGARP antibody or antigen binding fragment thereof wherein the variable region of the light chain comprises at least one of the followings CDRs:
VL-CDR1: QASQX$_1$IX$_2$SX$_3$LA (SEQ ID NO: 16), wherein X$_1$ is S or T, X$_2$ is S or V, X$_3$ is Y or F;
VL-CDR2: X$_1$X$_2$SX$_3$X$_4$X$_5$T (SEQ ID NO: 17), wherein X$_1$ is G or R; X$_2$ is A or T; X$_3$ is R or I; X$_4$ is L or P; X$_5$ is Q or K; and
VL-CDR3: QQYX$_1$SX$_2$PX$_3$T, wherein X$_1$ is D, A, Y or V; X$_2$ is A, L or V; X$_3$ is V or P (SEQ ID NO: 18).

Another object of the invention is an anti-hGARP antibody or antigen binding fragment thereof wherein the variable region of the heavy chain comprises the VH-CDR1 of SEQ ID NO: 13, VH-CDR2 of SEQ ID NO: 14 and VH-CDR3 of SEQ ID NO: 15 and the variable region of the light chain comprises at least one of VL-CDR1 as set forth in SEQ ID NO: 19; SEQ ID NO: 22; SEQ ID NO: 25; SEQ ID NO: 28; or SEQ ID NO: 31; at least one of VL-CDR2 as set forth in SEQ ID NO: 20; SEQ ID NO: 23; SEQ ID NO: 26; SEQ ID NO: 29; or SEQ ID NO: 32 and at least one of VL-CDR3 as set forth in SEQ ID NO: 21; SEQ ID NO: 24; SEQ ID NO: 27; SEQ ID NO: 30; or SEQ ID NO: 33.

Another object of the invention is an anti-hGARP antibody or antigen binding fragment thereof wherein the variable region of the light chain comprises at least one of the followings CDRs:

```
                                            (SEQ ID NO: 19)
    VL-CDR1: QASQSISSYLA;

(SEQ ID NO: 20)
    VL-CDR2: GASRLQT;
    and (SEQ ID NO: 21)
    VL-CDR3: QQYDSLPVT.
```

Another object of the invention is an anti-hGARP antibody or antigen binding fragment thereof wherein the variable region of the light chain comprises at least one of the followings CDRs:

```
                                            (SEQ ID NO: 22)
    VL-CDR1: QASQSIVSYLA;

(SEQ ID NO: 23)
    VL-CDR2: GASRLQT;
    and (SEQ ID NO: 24)
    VL-CDR3: QQYASAPVT.
```

Another object of the invention is an anti-hGARP antibody or antigen binding fragment thereof wherein the variable region of the light chain comprises at least one of the followings CDRs:

```
                                            (SEQ ID NO: 25)
    VL-CDR1: QASQSISSYLA;

(SEQ ID NO: 26)
    VL-CDR2: GTSRLKT;
    and (SEQ ID NO: 27)
    VL-CDR3: QQYYSAPVT.
```

Another object of the invention is an anti-hGARP antibody or antigen binding fragment thereof wherein the variable region of the light chain comprises at least one of the followings CDRs:

```
                                            (SEQ ID NO: 28)
    VL-CDR1: QASQTISSFLA;

(SEQ ID NO: 29)
    VL-CDR2: RASIPQT;
    and (SEQ ID NO: 30)
    VL-CDR3: QQYVSAPPT.
```

Another object of the invention is an anti-hGARP antibody or antigen binding fragment thereof wherein the variable region of the light chain comprises at least one of the followings CDRs:

```
                                            (SEQ ID NO: 31)
    VL-CDR1: QASQSISSYLA;

(SEQ ID NO: 32)
    VL-CDR2: GASRLKT;
    and (SEQ ID NO: 33)
    VL-CDR3: QQYASVPVT.
```

In an embodiment of the invention, the anti-hGARP antibody or antigen binding fragment thereof may comprise the CH1 domain, hinge region, CH2 domain and CH3 domain of a human antibody, in particular IgG1, IgG2, IgG3 or IgG4.

In an embodiment of the invention, the anti-hGARP antibody or antigen binding fragment thereof comprises in its heavy chain the following CDRs: VH-CDR1 GFSLTGYGIN (SEQ ID NO: 2), VH-CDR2 MIWSDGSTDYNSVLTS (SEQ ID NO: 3) and VH-CDR3 DRNYYDYDGAMDY (SEQ ID NO: 4).

In another embodiment of the invention, the anti-hGARP antibody or antigen binding fragment thereof comprises in its heavy chain the following CDRs: VH-CDR1 GYGIN (SEQ ID NO: 52), VH-CDR2 MIWSDGSTDYNSVLTS (SEQ ID NO: 3) and VH-CDR3 DRNYYDYDGAMDY (SEQ ID NO: 4).

In another embodiment of the invention, the anti-hGARP antibody or antigen binding fragment thereof comprises in its light chain the following CDRs: VL-CDR1 KASDHIKNWLA (SEQ ID NO: 5), VL-CDR2 GATSLEA (SEQ ID NO: 6) and VL-CDR3 QQYWSTPWT (SEQ ID NO: 7).

In an embodiment of the invention, the anti-hGARP antibody or antigen binding fragment thereof comprises in its heavy chain the following CDRs: VH-CDR1 SYYID (SEQ ID NO: 13), VH-CDR2 RIDPEDGGTKYAQKFQG (SEQ ID NO: 14) and VH-CDR3 NEWETVVVGDLMYEYEY (SEQ ID NO: 15).

In another embodiment of the invention, the anti-hGARP antibody or antigen binding fragment thereof comprises in its light chain the following CDRs: VL-CDR1 QASQX$_1$I X$_2$SX$_3$LA (SEQ ID NO: 16), wherein X$_1$ is S or T, X$_2$ is S or V, X$_3$ is Y or F; VL-CDR2 X$_1$X$_2$SX$_3$X$_4$X$_5$T (SEQ ID NO: 17), wherein X$_1$ is G or R; X$_2$ is A or T; X$_3$ is R or I; X$_4$ is L or P; X$_5$ is Q or K; and VL-CDR3 QQYX$_1$SX$_2$PX$_3$T, wherein X$_1$ is D, A, Y or V; X$_2$ is A, L or V; X$_3$ is V or P (SEQ ID NO: 18).

In another embodiment of the invention, the anti-hGARP antibody or antigen binding fragment thereof comprises in its light chain the following CDRs: VL-CDR1 QASQSIS-SYLA (SEQ ID NO: 19), VL-CDR2 GASRLQT (SEQ ID NO: 20), and VL-CDR3 QQYDSLPVT (SEQ ID NO: 21).

In another embodiment of the invention, the anti-hGARP antibody or antigen binding fragment thereof comprises in its light chain the following CDRs: VL-CDR1 QASQSIV-SYLA (SEQ ID NO: 22); VL-CDR2 GASRLQT (SEQ ID NO: 23); and VL-CDR3: QQYASAPVT (SEQ ID NO: 24).

In another embodiment of the invention, the anti-hGARP antibody or antigen binding fragment thereof comprises in its light chain the following CDRs: VL-CDR1 QASQSIS-SYLA (SEQ ID NO: 25); VL-CDR2 GTSRLKT (SEQ ID NO: 26); and VL-CDR3 QQYYSAPVT (SEQ ID NO: 27).

In another embodiment of the invention, the anti-hGARP antibody or antigen binding fragment thereof comprises in its light chain the following CDRs: VL-CDR1 QASQTISS-FLA (SEQ ID NO: 28); VL-CDR2 RASIPQT (SEQ ID NO: 29); and VL-CDR3 QQYVSAPPT (SEQ ID NO: 30).

In another embodiment of the invention, the anti-hGARP antibody or antigen binding fragment thereof comprises in its light chain the following CDRs: VL-CDR1 QASQSIS-SYLA (SEQ ID NO: 31); VL-CDR2 GASRLKT (SEQ ID NO: 32); and VL-CDR3 QQYASVPVT (SEQ ID NO: 33).

According to the invention, any of the CDRs 1, 2 and 3 of the heavy and light chains may be characterized as having an amino acid sequence that shares at least 60%, 70%, 75%, 80%, 85%, 90%, 95%, 96%, 97%, 98%, 99% of identity with the particular CDR or sets of CDRs listed in the corresponding SEQ ID NO.

In another embodiment of the invention, the anti-hGARP antibody or antigen binding fragment thereof is selected from the group consisting of an antibody having:
  (i) the heavy chain CDR 1, 2 and 3 (VH-CDR1, VH-CDR2, VH-CDR3) amino acid sequences as shown in SEQ ID NO: 2, 3 and 4; and
  (ii) the light chain CDR 1, 2 and 3 (VL-CDR1, VL-CDR2, VL-CDR3) amino acid sequences as shown in SEQ ID NO: 5, 6 and 7 respectively;
optionally wherein one, two, three or more of the amino acids in any of said sequences may be substituted by a different amino acid.

In another embodiment of the invention, the anti-hGARP antibody or antigen binding fragment thereof is selected from the group consisting of an antibody having:
  (i) the heavy chain CDR 1, 2 and 3 (VH-CDR1, VH-CDR2, VH-CDR3) amino acid sequences as shown in SEQ ID NO: 52, 3 and 4; and
  (ii) the light chain CDR 1, 2 and 3 (VL-CDR1, VL-CDR2, VL-CDR3) amino acid sequences as shown in SEQ ID NO: 5, 6 and 7 respectively;
optionally wherein one, two, three or more of the amino acids in any of said sequences may be substituted by a different amino acid.

In another embodiment of the invention, the anti-hGARP antibody or antigen binding fragment thereof is selected from the group consisting of an antibody having:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 16, 17 and 18 respectively;
optionally wherein one, two, three or more of the amino acids in any of said sequences may be substituted by a different amino acid.

In another embodiment of the invention, the anti-hGARP antibody or antigen binding fragment thereof comprises:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 19, 20 and 21 respectively;
optionally wherein one, two, three or more of the amino acids in any of said sequences may be substituted by a different amino acid.

In another embodiment of the invention, the anti-hGARP antibody or antigen binding fragment thereof comprises:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 22, 23 and 24 respectively;
optionally wherein one, two, three or more of the amino acids in any of said sequences may be substituted by a different amino acid.

In another embodiment of the invention, the anti-hGARP antibody or antigen binding fragment thereof comprises:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 25, 26 and 27 respectively;
optionally wherein one, two, three or more of the amino acids in any of said sequences may be substituted by a different amino acid.

In another embodiment of the invention, the anti-hGARP antibody or antigen binding fragment thereof comprises:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 28, 29 and 30 respectively;
optionally wherein one, two, three or more of the amino acids in any of said sequences may be substituted by a different amino acid.

In another embodiment of the invention, the anti-hGARP antibody or antigen binding fragment thereof comprises:
  (i) the heavy chain CDR 1, 2 and 3 (VH-CDR1, VH-CDR2, VH-CDR3) amino acid sequences as shown in SEQ ID NO: 13, 14 and 15; and
  (ii) the light chain CDR 1, 2 and 3 (VL-CDR1, VL-CDR2, VL-CDR3) amino acid sequences as shown in SEQ ID NO: 31, 32 and 33 respectively;
optionally wherein one, two, three or more of the amino acids in any of said sequences may be substituted by a different amino acid.

In an embodiment, the anti-hGARP antibody or antigen binding fragment thereof comprises a variable heavy chain CDR3 comprising an amino acid sequence of SEQ ID NO:

4 (DRNYYDYDGAMDY), or sequence variant thereof, wherein the sequence variant comprises one, two or three amino acid substitutions in the recited sequence.

In an embodiment, the anti-hGARP antibody or antigen binding fragment thereof comprises a variable heavy chain CDR3 comprising an amino acid sequence of SEQ ID NO: 15, or sequence variant thereof, wherein the sequence variant comprises one, two or three amino acid substitutions in the recited sequence.

Another object of the invention is the anti-hGARP antibody MHGARP8 or antigen binding fragment thereof comprising a heavy chain variable region of sequence SEQ ID NO: 8 and a light chain variable region of sequence SEQ ID NO: 9.

(SEQ ID NO: 8)
MAVLALLFCLVTFPSCILSQVQLKESGPGLVAPSQSLSITCTVSGFSLTG

YGINWVRQPPGKGLEWLGMIWSDGSTDYNSVLTSRLRISKDNSNSQVFLK

MNSLQVDDTARYYCARDRNYYDYDGAMDYWGQGTSVTVSS.

(SEQ ID NO: 9)
MKFPSQLLLFLLFRITGIICDIQVTQSSSYLSVSLGDRVTITCKASDHIK

NWLAWYQQKPGIAPRLLVSGATSLEAGVPSRFSGSGSGKNFTLSITSLQT

EDVATYYCQQYWSTPWTFGGGTTLEIR.

Another object of the invention is the anti-hGARP antibody MHGARP8 or antigen binding fragment thereof comprising a heavy chain variable region of sequence SEQ ID NO: 50 and a light chain variable region of sequence SEQ ID NO: 51, wherein SEQ ID NO: 50 and SEQ ID NO: 51 correspond, respectively, to SEQ ID NO: 8 and SEQ ID NO: 9 wherein the signal peptide sequences were removed.

(SEQ ID NO: 50)
QVQLKESGPGLVAPSQSLSITCTVSGFSLTGYGINWVRQPPGKGLEWLGM

IWSDGSTDYNSVLTSRLRISKDNSNSQVFLKMNSLQVDDTARYYCARDRN

YYDYDGAMDYWGQGTSVTVSS.

(SEQ ID NO: 51)
DIQVTQSSSYLSVSLGDRVTITCKASDHIKNWLAWYQQKPGIAPRLLVSG

ATSLEAGVPSRFSGSGSGKNFTLSITSLQTEDVATYYCQQYWSTPWTFGG

GTTLEIR.

Another object of the invention is the anti-hGARP antibody LHG10 or antigen binding fragment thereof comprising a heavy chain variable region of sequence SEQ ID NO: 34 and a light chain variable region of sequence SEQ ID NO: 35.

(SEQ ID NO: 34)
EVQLVQPGAELRNSGASVKVSCKASGYRFTSYYIDWVRQAPGQGLEWMGR

IDPEDGGTKYAQKFQGRVTFTADTSTSTAYVELSSLRSEDTAVYYCARNE

WETVVVGDLMYEYEYWGQGTQVTVSS.

(SEQ ID NO: 35)
DIQMTQSPTSLSASLGDRVTITCQASQSISSYLAWYQQKPGQAPKLLIYG

ASRLQTGVPSRFSGSGSGTSFTLTISGLEAEDAGTYYCQQYDSLPVTFGQ

GTKVELK.

Another object of the invention is the anti-hGARP antibody LHG10.3 or antigen binding fragment thereof comprising a heavy chain variable region of sequence SEQ ID NO: 34 and a light chain variable region of sequence SEQ ID NO: 36.

(SEQ ID NO: 36)
DIQMTQSPSSLSASLGDRVTITCQASQSIVSYLAWYQQKPGQAPKLLIYG

ASRLQTGVPSRFSGSGSGTSFTLTISGLEAEDAGTYYCQQYASAPVTFGQ

GTGVELK.

Another object of the invention is the anti-hGARP antibody LHG10.4 or antigen binding fragment thereof comprising a heavy chain variable region of sequence SEQ ID NO: 34 and a light chain variable region of sequence SEQ ID NO: 37.

(SEQ ID NO: 37)
DIQMTQSPSSLSASLGDRVTITCQASQSISSYLAWYQQKPGQAPKLL

IYGTSRLKTGVPSRFSGSGSGTSFTLTISGLEAEDAGTYYCQQYYSA

PVTFGQGTKVELK.

Another object of the invention is the anti-hGARP antibody LHG10.5 or antigen binding fragment thereof comprising a heavy chain variable region of sequence SEQ ID NO: 34 and a light chain variable region of sequence SEQ ID NO: 38.

(SEQ ID NO: 38)
DIQMTQSPSSLSPSLGDRVTITCQASQTISSFLAWYHQKPGQPPKLL

IYRASIPQTGVPSRFSGSGSGTSFTLTIGGLEAEDAGTYYCQQYVSA

PPTFGQGTKVELK.

Another object of the invention is the anti-hGARP antibody LHG10.6 thereof comprising a heavy chain variable region of sequence SEQ ID NO: 34 and a light chain variable region of sequence SEQ ID NO: 39.

(SEQ ID NO: 39)
DIQMTQSPSSLSASLGDRVTITCQASQSISSYLAWYQQKPGQAPNIL

IYGASRLKTGVPSRFSGSGSGTSFTLTISGLEAEDAGTYYCQQYASV

PVTFGQGTKVELK.

In an embodiment of the invention, one, two, three or more of the amino acids of the heavy chain or light chain variable regions as described here above may be substituted by a different amino acid.

In another embodiment, an antibody of the invention comprises heavy and light chain variable regions comprising amino acid sequences that are homologous to the amino acid sequences of the MHGARP8 antibody described herein, and wherein the antibodies retain the desired functional properties of the protein of the invention.

In an embodiment of the invention, the sequence of the heavy chain variable region of an anti-hGARP of the invention encompasses sequences that have 60%, 70%, 75%, 80%, 85%, 90%, 95%, 96%, 97%, 98%, 99% of identity with SEQ ID NO: 8 or with SEQ ID NO: 50.

In an embodiment of the invention, the sequence of light chain variable region of an anti-hGARP of the invention encompasses sequences that have 60%, 70%, 75%, 80%, 85%, 90%, 95%, 96%, 97%, 98%, 99% of identity with SEQ ID NO: 9 or with SEQ ID NO: 51.

In another embodiment, an antibody of the invention comprises heavy and light chain variable regions comprising amino acid sequences that are homologous to the amino acid sequences of the LHG10 antibody described herein, and wherein the antibodies retain the desired functional properties of the protein of the invention.

In an embodiment of the invention, the sequence of the heavy chain variable region of an anti-hGARP of the invention encompasses sequences that have 60%, 70%, 75%, 80%, 85%, 90%, 95%, 96%, 97%, 98%, 99% of identity with SEQ ID NO: 34.

In an embodiment of the invention, the sequence of light chain variable region of an anti-hGARP of the invention encompasses sequences that have 60%, 70%, 75%, 80%, 85%, 90%, 95%, 96%, 97%, 98%, 99% of identity with SEQ ID NO: 35; 36; 37; 38 or 39.

In any of the antibodies of the invention, e.g. MHGARP8 or LHG10, the specified variable region and CDR sequences may comprise conservative sequence modifications. Conservative sequence modifications refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein. anti-hGARP antibodies may also be CDR-grafted antibodies in which the CDRs are derived from a camelid antibody, for example a camelid anti-hGARP antibody raised by active immunization with hGARP.

In an embodiment, the invention provides an antibody that binds essentially the same epitope as the MHGARP8 or LHG10 antibody.

In some embodiments of this invention, anti-hGARP antibodies comprising VH and VL domains, or CDRs thereof may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have a fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Advantageously, the CH1 domain, hinge region, CH2 domain, CH3 domain and CL domain (and CH4 domain if present) may all have a fully or substantially human amino acid sequence. In the context of the constant region of a humanized or chimeric antibody, or an antibody fragment, the term "substantially human" refers to an amino acid sequence identity of at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required. The presence of a "fully human" hinge region in the anti-hGARP antibodies of the invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved effector function. See Caron et al., J. Exp. Med. 176: 1191-1195 (1992) and Shopes, B. J. Immunol. 148:2918-2922 (1992). Alternatively, a GARP antibody can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, 2010 Nature Reviews: Immunology, 10:301-316, incorporated herein by reference. Variant anti-hGARP antibodies in which the Fc region is modified by protein engineering, as described herein, may also exhibit an improvement in efficacy (e.g. in therapeutics/diagnostics), as compared to an equivalent antibody (i.e. equivalent antigen-binding properties) without the Fc modification.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. In still another embodiment, the glycosylation of an antibody is modified. For example, an aglycoslated antibody can be made (i.e., the antibody lacks glycosylation). Glycosylation can be altered to, for example, increase the affinity of the antibody for the GARP target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Also envisaged are variant anti-hG-ARP antibodies having an altered type of glycosylation, such as a hypofucosylated antibody having reduced amounts of fucosyl residues or a non-fucosylated antibody (as described by Natsume et al., 2009 Drug Design Development and Therapy, 3:7-16) or an antibody having increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, 2009 mAbs 1(3):230-236).

In an embodiment of the invention, the anti-hGARP antibody comprises an Fc region having the sequence SEQ ID NO: 47.

(SEQ ID NO: 47)
PKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLH

QDWLNGKEYKCKVSNKALPAPIEKTISKAKGQPREPQVYTLPPSRDE

LTKNQVSLTCLVKGFYPSDIAVEWESNGQPENNYKTTPPVLDSDGSF

FLYSKLTVDKSRWQQGNVFSCSVMHEALHNHYTQKSLSLSPGK.

In another embodiment of the invention, the anti-hGARP antibody comprises the heavy chain constant domain region having the sequence SEQ ID NO: 48, wherein X is N or is mutated into Q to inhibit ADCC.

(SEQ ID NO: 48)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPE

VTCVVVDVSHEDPEVKFNWYVDGVEVHNAKTKPREEQYXSTYRVVSV

LTVLHQDWLNGKEYKCKVSNKALPAPIEKTISKAKGQPREPQVYTLP

PSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

K.

In an embodiment of the invention, the residue 297 of SEQ ID NO: 48 is aglycosylated.

In another embodiment of the invention, the N residue at the position 297 of SEQ ID NO: 48 is mutated into Q.

In an embodiment of the invention, the anti-hGARP antibody comprises the light chain constant domain region having the sequence SEQ ID NO: 49.

(SEQ ID NO: 49)
RTVAAPSVFIFPPSDEQLKSGTASVVCLLNNFYPREAKVQWKVDNAL

QSGNSQESVTEQDSKDSTYSLSSTLTLSKADYEKHKVYACEVTHQGL

SSPVTKSFNRGEC.

In further embodiments of the invention, anti-hGARP antibodies may be lacking effector function, either because the Fc region of the antibody is of an isotype which naturally lacks effector function, or which exhibits significantly less potent effector function than human IgG1, for example human IgG2 or human IgG4, or because the Fc region of the antibody has been engineered to reduce or substantially eliminate effector function, as described in Armour K L, et al., Eur. J. Immunol., 1999, 29:2613-2624.

In further embodiments, the Fc region of the anti-hGARP antibody may be engineered to facilitate the preferential formation of bispecific antibodies, in which two antibody heavy chains comprising different variable domains pair to form the Fc region of the bispecific antibody. Examples of such modifications include the "knobs-into-hole" modifications described by Ridgway J B, Presta L G, Carter P., 1996 Protein Eng. July; 9(7):617-21 and Merchant A M, et al. 1998 Nat Biotechnol. July; 16(7):677-81.

In an embodiment of the invention, the anti-hGARP antibody of the invention may exhibit one or more effector functions selected from antibody-dependent cell-mediated cytotoxicity (ADCC), complement dependent cytotoxicity (CDC) and antibody-dependent cell-mediated phagocytosis (ADCP) against cells expressing human GARP protein on the cell surface. The antibody may exhibit ADCC against GARP-related dysfunctional cells. The antibody may exhibit enhanced ADCC function in comparison to a reference antibody which is an equivalent antibody comprising a native human Fc domain. In a non-limiting embodiment, the ADCC function may be at least 10× enhanced in comparison to the reference antibody comprising a native human Fc domain. In this context "equivalent" may be taken to mean that the antibody with enhanced ADCC function displays substantially identical antigen-binding specificity and/or shares identical amino acid sequence with the reference antibody, except for any modifications made (relative to native human Fc) for the purposes of enhancing ADCC. The antibody may contain the hinge region, CH1 domain, CH2 domain and CH3 domain of a human IgG, most preferably human IgG1. The antibody may include modifications in the Fc region, such as for example substitutions, deletions or insertion or other structural modifications to enhance or reduce Fc-dependent functionalities.

One object of this invention relates to anti-hGARP antibodies or antigen binding fragment thereof which inhibit TGF-β signaling, and that may be particularly suitable for therapeutic applications which benefit from antibody effector function, i.e. ADCC, CDC, ADCP, and in particular enhanced effector function. Hence, the GARP antibodies described herein which exhibit effector function (or enhanced effector function) and which inhibit TGF-β may be particularly advantageous for certain therapeutic applications, e.g. cancer, chronic infection, fibrosis treatments which benefit from antibody effector function.

Another object of the invention is an isolated polynucleotide sequence encoding the heavy chain variable region of sequence SEQ ID NO: 8 or of SEQ ID NO: 50. Preferably, said nucleic sequence is SEQ ID NO: 10:

```
ATGGCTGTCCTGGCATTACTCTTCTGCCTGGTAACATTCCCAAGCTG

TATCCTTTCCCAGGTGCAGCTGAAGGAGTCAGGACCTGGCCTGGTGG

CGCCCTCACAGAGCCTGTCCATCACATGCACCGTCTCAGGGTTCTCA

TTAACCGGCTATGGTATAAACTGGGTTCGCCAGCCTCCAGGAAAGGG

TCTGGAGTGGCTGGGAATGATATGGAGTGATGGAAGCACAGACTATA

ATTCAGTTCTCACATCCAGACTGAGGATCAGTAAGGATAATTCCAAT

AGCCAGGTTTTCTTAAAAATGAACAGTCTGCAAGTTGATGACACAGC

CAGGTACTATTGTGCCAGAGATCGAAACTACTATGATTACGACGGGG

CTATGGACTACTGGGGTCAAGGAACCTCAGTCACCGTCTCCTCA.
```

Another object of the invention is an isolated polynucleotide sequence encoding the light chain variable region of sequence SEQ ID NO: 9 or of SEQ ID NO: 51. Preferably, said nucleic sequence is SEQ ID NO: 11:

```
ATGAAGTTTCCTTCTCAACTTCTGCTCTTCCTGCTGTTCAGAATCAC

AGGCATAATATGTGACATCCAGGTGACACAATCTTCATCCTACTTGT

CTGTATCTCTAGGAGACAGGGTCACCATTACTTGCAAGGCAAGTGAC

CACATTAAAAATTGGTTAGCCTGGTATCAGCAGAAACCAGGAATTGC

TCCTAGGCTCTTAGTTTCTGGTGCAACCAGTTTGGAAGCTGGGGTTC

CTTCAAGATTCAGTGGCAGTGGATCTGGAAAGAATTTCACTCTCAGC

ATTACCAGTCTTCAGACTGAAGATGTTGCTACTTATTACTGTCAACA

GTATTGGAGTACACCGTGGACGTTCGGTGGAGGCACCACTCTGGAGA

TCAGA.
```

Another object of the invention is an expression vector comprising the nucleic sequences encoding the anti-hGARP antibody of the invention. In an embodiment, the expression vector of the invention comprises at least one of SEQ ID NO: 10 and SEQ ID NO: 11 or any sequence having a nucleic acid sequence that shares at least: 60%, 70%, 75%, 80%, 85%, 90%, 95%, 96%, 97%, 98%, 99% of identity with said SEQ ID NO: 10 and SEQ ID NO: 11.

Another object of the invention is an isolated host cell comprising said vector. Said host cell may be used for the recombinant production of the antibodies of the invention. In an embodiment, host cells may be prokaryote, yeast, or eukaryotes cells preferably mammalian cells, such as, for example: monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); mouse myeloma cells SP2/0-AG14 (ATCC CRL 1581; ATCC CRL 8287) or NSO (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art. It should be noted that the term "host cell" generally refers to a cultured cell line. Whole human beings into which an expression vector encoding an antigen binding polypeptide according to the invention has been introduced are explicitly excluded from the definition of a "host cell".

Another objet of the invention is a method of producing an anti-hGARP antibody or antigen binding fragment thereof which comprises culturing host cells containing the isolated polynucleotide sequence encoding the anti-hGARP antibody under conditions suitable for expression of the anti-hGARP antibody, and recovering the expressed anti-hGARP antibody. This recombinant process can be used for large scale production of GARP antibodies according to the invention, including antibodies monoclonal antibodies intended for in vitro, ex vivo, in vivo therapeutic, diagnostic uses. These processes are available in the art and will be known by the skilled person.

Another object of the invention is a hybridoma cell line which produce said antibody of the invention.

The preferred hybridoma cell lines according to the invention were deposited with the BCCM/LMBP Plasmid Collection, Department of Biomedical Molecular Biology, Ghent University, 'Fiers-Schell-Van Montagu' building, Technologiepark 927, B-9052 Gent-Zwijnaarde BELGIUM (Table 2):

TABLE 2

| Cell line | Deposition No. | Date of deposit |
|---|---|---|
| MHGARP8 hybridoma | LMBP 10246CB | 30 May 2013 |

Fragments and derivatives of antibodies of this invention (which are encompassed by the term "antibody" or "antibodies" as used in this application, unless otherwise stated or clearly contradicted by context), preferably a MHGARP8-like antibody, can be produced by techniques that are known in the art. "Fragments" comprise a region of the intact antibody, generally the antigen binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multi-specific antibodies formed from antibody fragments. Fragments of the present antibodies can be obtained using standard methods. For instance, Fab or F(ab')2 fragments may be produced by protease digestion of the isolated antibodies, according to conventional techniques. It will be appreciated that immune-reactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al, Cytokines 16 (3): 106-119 (2001) and Delgado et al, Br. J. Cancer 73 (2): 175-182 (1996), the disclosures of which are incorporated herein by reference.

Alternatively, the DNA of a hybridoma producing an antibody of the invention, preferably a MHGARP8-like or LHG10-like antibody, may be modified so as to encode a fragment of the invention. The modified DNA is then inserted into an expression vector and used to transform or transfect an appropriate cell, which then expresses the desired fragment.

In certain embodiments, the DNA of a hybridoma producing an antibody of this invention, preferably a MHGARP8-like or LHG10-like antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

Thus, according to another embodiment, the antibody of this invention, preferably a MHGARP8 or LHG10-like antibody is humanized. "Humanized" forms of antibodies according to this invention are specific chimeric immunoglobulins, immunoglobulin chains or fragments thereof (such as Fv, Fab, Fab', F(ab')2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework (FR) residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a region of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 3, pp. 394 (1992); Verhoeyen et al. Science, 239, pp. 1534; and U.S. Pat. No. 4,816,567, the entire disclosures of which are herein incorporated by reference. Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence that is closed to the mouse sequence is then accepted as the human framework (FR) for the humanized antibody (Sims et al., J. Immunol. 151, pp. 2296 (1993); Chothia and Lesk, J. Mol. Biol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al. J. Immunol., 151 (1993)). It is further important that antibodies be humanized with retention of high affinity for GARP and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al. Nature 362 (1993) 255), or by selection of antibody repertoires using phage display methods. Such techniques are known to the skilled person and can be implemented starting from monoclonal antibodies as disclosed in the present application.

In an embodiment, Camelidae hypervariable loops (or CDRs) may be obtained by active immunization of a species in the family Camelidae with a desired target antigen. As discussed and exemplified in detail herein, following immunization of Camelidae (either the native animal or a transgenic animal engineered to express the immunoglobulin repertoire of a camelid species) with the target antigen, B cells producing (conventional Camelidae) antibodies having specificity for the desired antigen can be identified and polynucleotide encoding the VH and VL domains of such antibodies can be isolated using known techniques.

In an embodiment, the invention provides a recombinant antigen binding polypeptide immunoreactive with a target antigen, the polypeptide comprising a VH domain and a VL domain, wherein at least one hypervariable loop or complementarity determining region in the VH domain or the VL domain is obtained from a VH or VL domain of a species in the family Camelidae, which antigen binding polypeptide is obtainable by a process comprising the steps of:
  (a) immunizing a species in the family Camelidae with a target antigen or with a polynucleotide encoding said target antigen and raising an antibody to said target antigen;
  (b) determining the nucleotide sequence encoding at least one hypervariable loop or complementarity determining region (CDR) of the VH and/or the VL domain of a Camelidae conventional antibody immunoreactive with said target antigen; and
  (c) expressing an antigen binding polypeptide immunoreactive with said target antigen, said antigen binding polypeptide comprising a VH and a VL domain, wherein at least one hypervariable loop or complementarity determining region (CDR) of the VH domain or the VL domain has an amino acid sequence encoded by the nucleotide sequence determined in part (a).

Isolated Camelidae VH and VL domains obtained by active immunization can be used as a basis for engineering antigen binding polypeptides according to the invention. Starting from intact Camelidae VH and VL domains, it is possible to engineer one or more amino acid substitutions, insertions or deletions which depart from the starting Camelidae sequence.

In an embodiment, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerization, etc.) or to enhance some other favourable property of the molecule (e.g. solubility, stability, bioavailability, etc.).

In another embodiment, changes in primary amino acid sequence can be engineered in one or more of the hypervariable loops (or CDRs) of a Camelidae VH and/or VL domain obtained by active immunization. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerization, etc., or to enhance some other favourable property of the molecule, e.g. solubility, stability, bioavailability, etc.

The antibodies of the present invention, preferably a MHGARP8 or LHG10-like antibody, may also be derivatized to "chimeric" antibodies (immunoglobulins) in which a region of the heavy/light chain(s) is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity and binding specificity (Cabilly et al., supra; Morrison et al., Proc. Natl. Acad. Sci., pp. 6851 (1984)).

An object of the invention is a composition comprising at least one of the protein of the invention as described here above.

Another object of the invention is a pharmaceutical composition comprising at least one of the protein of the invention as described here above and a pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the invention is the protein of the invention for inhibiting TGF-β activity in a subject in need thereof.

Another object of the invention is a method for inhibiting TGF-β activity in a subject in need thereof, comprising administering to the subject an effective amount of the protein of the invention.

Another object of the invention is the protein of the invention or the pharmaceutical composition as defined here above for treating a TGF-β-related disorder in a subject in need thereof.

Another object of the invention is a method for treating a TGF-β-related disorder in a subject in need thereof, comprising administering to the subject an effective amount of the protein of the invention.

Diseases or disorders where the methods of the invention can be used include all diseases where inhibition of TGF-β can be beneficial.

Said TGF-β-related disorder includes, but is not limited to, inflammatory diseases, chronic infection, cancer, fibrosis, cardiovascular diseases, cerebrovascular disease (e.g. ischemic stroke), and neurodegenerative diseases.

For use in administration to a subject, the composition will be formulated for administration to the subject. The compositions of the present invention may be administered orally, parenterally, by inhalation spray, topically, rectally, nasally, buccally, vaginally or via an implanted reservoir. The term administration used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for intravenous (IV) administration in 9.0 mg/mL sodium chloride, 7.35 mg/mL sodium citrate dihydrate, 0.7 in g/mL polysorbate 80, and Sterile Water for Injection. The pH is adjusted to 6.5. It will be appreciated that these schedules are exemplary and that an optimal schedule and regimen can be adapted taking into account the affinity and tolerability of the particular antibody in the pharmaceutical composition that must be determined in clinical trials.

Another object of the invention is a method for reducing immunosuppression in the tumor environment in a subject in need thereof, comprising administering to the subject a therapeutically effective amount of the protein of the invention.

Another object of the invention is a method for boosting the immune system in a subject in need thereof, comprising administering to the subject a therapeutically effective amount of the protein of the invention.

Another object of the invention is a method for inhibiting the immune suppressive function of human Tregs in a subject in need thereof, comprising administering to the subject a therapeutically effective amount of the protein of the invention.

Another object of the invention is a method for treating cancer in a subject in need thereof, comprising administering to the subject a therapeutically effective amount of the protein of the invention.

Another object of the invention is a method for treating cancer in a subject in need thereof, wherein the pharmaceutical composition of the invention is to be administered as an immunostimulatory antibody for treatment of cancer patients.

Another object of the invention is a method for treating cancer in a subject in need thereof, comprising administering to the subject a therapeutically effective amount of the protein of the invention in combination with another treatment for cancer or an immunotherapeutic agent.

Another object of the invention is a combination of the protein of the invention and another treatment for cancer or another immunotherapeutic agent for treating or for use in treating cancer.

In an embodiment of the invention, said immunotherapeutic agent is a tumor vaccine.

In another embodiment of the invention, said immunotherapeutic agent is an immunostimulatory antibody.

Without willing to be bound to a theory, the inventors believe the protein of the invention will prevent immunosuppression in the tumor environment, thereby increasing the efficacy of the immunotherapeutic agent.

Various cancers can be treated by the present invention such as for an adrenocortical carcinoma, anal cancer, bladder cancer, brain tumor, glioma, breast carcinoma, carcinoid tumor, cervical cancer, colon carcinoma, endometrial cancer, esophageal cancer, extrahepatic bile duct cancer, Ewings tumor, extracranial germ cell tumor, eye cancer, gall bladder cancer, gastric cancer, germ cell tumor, gestational trophoblastic tumor, head and neck cancer, hypopharyngeal cancer, islet cell carcinoma, kidney cancer, laryngeal cancer, leukemia, lip and oral cavity cancer, liver cancer, lung cancer, lymphoma, melanoma, mesothelioma, merkel cell carcinoma, metastatic squamous head and neck cancer, myeloma, neoplasm, nasopharyngeal cancer, neuroblastoma, oral cancer, oropharyngeal cancer, osteosarcoma, ovarian cancer, pancreatic cancer, sinus and nasal cancer, parathyroid cancer, penile cancer, pheochromocytoma cancer, pituitary cancer, plasma cell neoplasm, prostate cancer, rhabdomyosarcoma, rectal cancer, renal cell carcinoma, salivary gland cancer, skin cancer, Kaposi's sarcoma, T-cell lymphoma, soft tissue sarcoma, stomach cancer, testicular cancer, thymoma, thyroid cancer, urethral cancer, uterine cancer, vaginal cancer, vulvar cancer, or Wilms' tumor.

Suitable tumor antigens for use as a tumor vaccine known in the art include for example: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, IA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le<x> (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH). Other tumor antigens include pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein\cyclophilin C-associated protein), TAAL6, TAG72, TLP, TPS, and the like.

Suitable immunostimulatory antibodies include, but are not limited to: anti-CTLA-4, anti-PD1, anti-PDL1 and anti-KIR antibodies.

In an embodiment of the invention, the method for treating cancer in a subject in need thereof, comprises administering to the subject the protein of the invention prior to, concurrent to and/or posterior to another anti-cancer agent or cancer treatment, such as chemotherapy treatment.

Another object of the present invention is a method to prevent infectious diseases such as HIV, malaria, or Ebola, or improve vaccination against these infections, comprising administering to the subject a therapeutically effective amount of the protein of the invention.

In an embodiment, the protein of the invention may be used in vitro or in vivo to identify samples, tissues, organs or cells that express GARP.

Examples of assays in which the protein of the invention may be used, include, but are not limited to, ELISA, sandwich ELISA, RIA, FACS, tissue immunohistochemistry, Western-blot, and immunoprecipitation.

In an embodiment of the invention, the sample is a biological sample. Examples of biological samples include, but are not limited to, bodily fluids, preferably blood, more preferably blood serum, plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages, tissue lysates and extracts prepared from diseased tissues.

In an embodiment of the invention, the term "sample" is intended to mean a sample taken from an individual prior to any analysis.

In another embodiment, the protein of the invention may be labeled for diagnostic or detection purposes. By labeled herein is meant that a compound has at least one element, isotope or chemical compound attached to enable the detection of the compound. Examples of labels include, but are not limited to, isotopic labels such as radioactive or heavy isotopes; magnetic, electric or thermal labels and colored or luminescent dyes. For example: lanthanide complexes, quantum dots, fluorescein, rhodamine, tetramethylrhodamine, eosin, erythrosin, coumarin, methyl-coumarins, pyrene, malachite green, stilbene, Lucifer yellow, cascade blue, texas red, alexa dyes, cy dyes.

One object of the invention is a method for identifying activated Tregs in a sample based on the use of the protein of the invention.

Another object of the invention is a method for identifying soluble or complexed latent TGF-β based on the use of the protein of the invention.

Another object of the invention is a kit comprising at least one protein of the invention.

By "kit" is intended any manufacture (e.g., a package or a container) comprising at least one reagent, i.e. for example an antibody, for specifically detecting the expression of GARP. The kit may be promoted, distributed, or sold as a unit for performing the methods of the present invention. Furthermore, any or all of the kit reagents may be provided within containers that protect them from the external environment, such as in sealed containers. The kits may also contain a package insert describing the kit and methods for its use.

Kits for performing the sandwich ELISA methods of the invention generally comprise a capture antibody, optionally immobilized on a solid support (e.g., a microtiter plate), and a revelation antibody coupled with a detectable substance, such as, for example HRP, a fluorescent label, a radioisotope, beta-galactosidase, and alkaline phosphatase.

(B) Abundance of the epitope recognized by MHGARP-8 increases upon overexpression of TGF-β1. Parental BW5147 T cells (BW untransfected) or clones stably transfected with hGARP alone (BW+hGARP) or with hTGFB1 (BW+hGARP+hTGF-b1) were stained as in A, or with >mLAP-AF647 or >hLAP-APC antibodies, and analyzed by flow cytometry.

(C) MHGARP-1, -2, -3, -4 and -5 recognize free hGARP, but not hGARP bound to TGF-β1. Cell lysates from parental BW5147 T cells or a clone stably transfected with hGARP and hTGFB1 were imunoprecipitated with >hGARP mAbs (MHGARP1 to 9, as indicated on top of the figure). Cell lysates (30% input) or IP products were analyzed by Western blot with a commercial >hGARP mAb (clone Plato-1, top panels) and with an antibody directed against a C-terminal epitope of TGF-β1, which detects pro-TGF-β1 as a 50 kDa band and mature TGF-β1 as a 13 kDa band (bottom panels).
* Aspecific product detected in untransfected cells.

(D) Overexpression of hTGFB1 in hGARP-transfected 293T cells decreases binding of MHGARP-1, -2, -3, -4, and -5, but increases binding of MHGARP-8. 293T cells were co-transfected with a hGARP-encoding plasmid (0.25 µg), the indicated amounts of a hTGFB1-encoding plasmid, and an empty plasmid to bring the total amount of transfected DNA to 2.5 µg in all conditions. Transfected cells were stained with >hGARP mAbs (MHGARP1 to 9, as indicated on top of the figure), and analyzed by flow cytometry.

(E) Silencing of hTGFB1 in hGARP-transduced JURKAT cells decreases binding of MHGARP-8. JURKAT cells, transduced or not with hGARP, were transfected with siRNA specific for the TGFB1 mRNA (siTGFB1) or a scramble siRNA control. Transfected cells were stained with >hGARP mAbs (MHGARP1 to 9, as indicated on top of the figure) or with an >hLAP antibody, and analyzed by flow cytometry.

Figure 4:
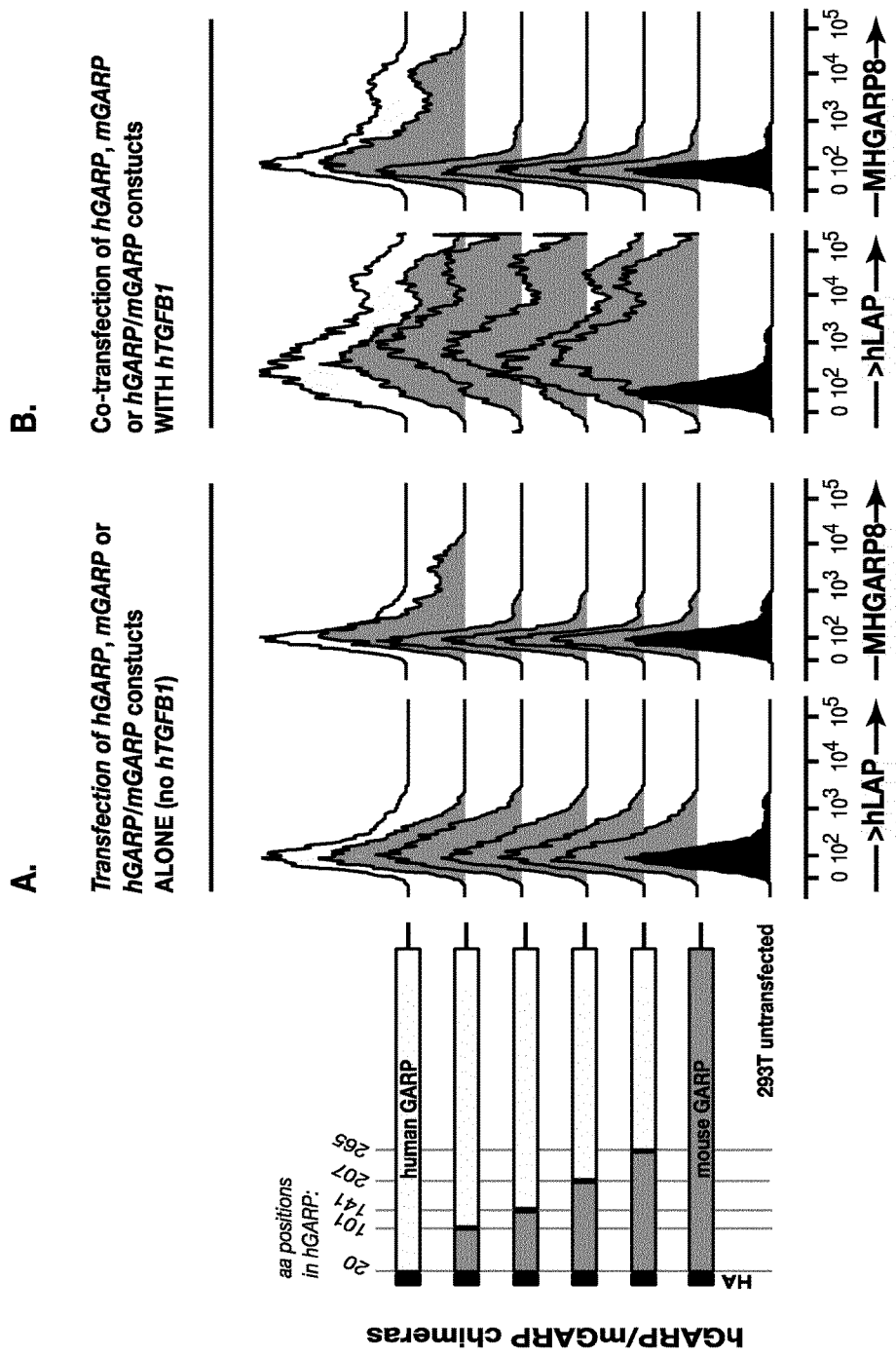

FIG. 4. Presentation of hTGF-β1 on the cell surface is not sufficient for binding by MHGARP8. 293T cells were transfected as indicated below, stained with >hLAP antibodies or with MGARP8, then analyzed by flow cytometry.

(A) Transfection with constructs encoding the HA-tagged proteins schematized on the left, without a hTGFB1 construct.

(B) Co-transfection with constructs encoding the HA-tagged proteins schematized on the left, with a hTGFB1 construct.

Figure 5:
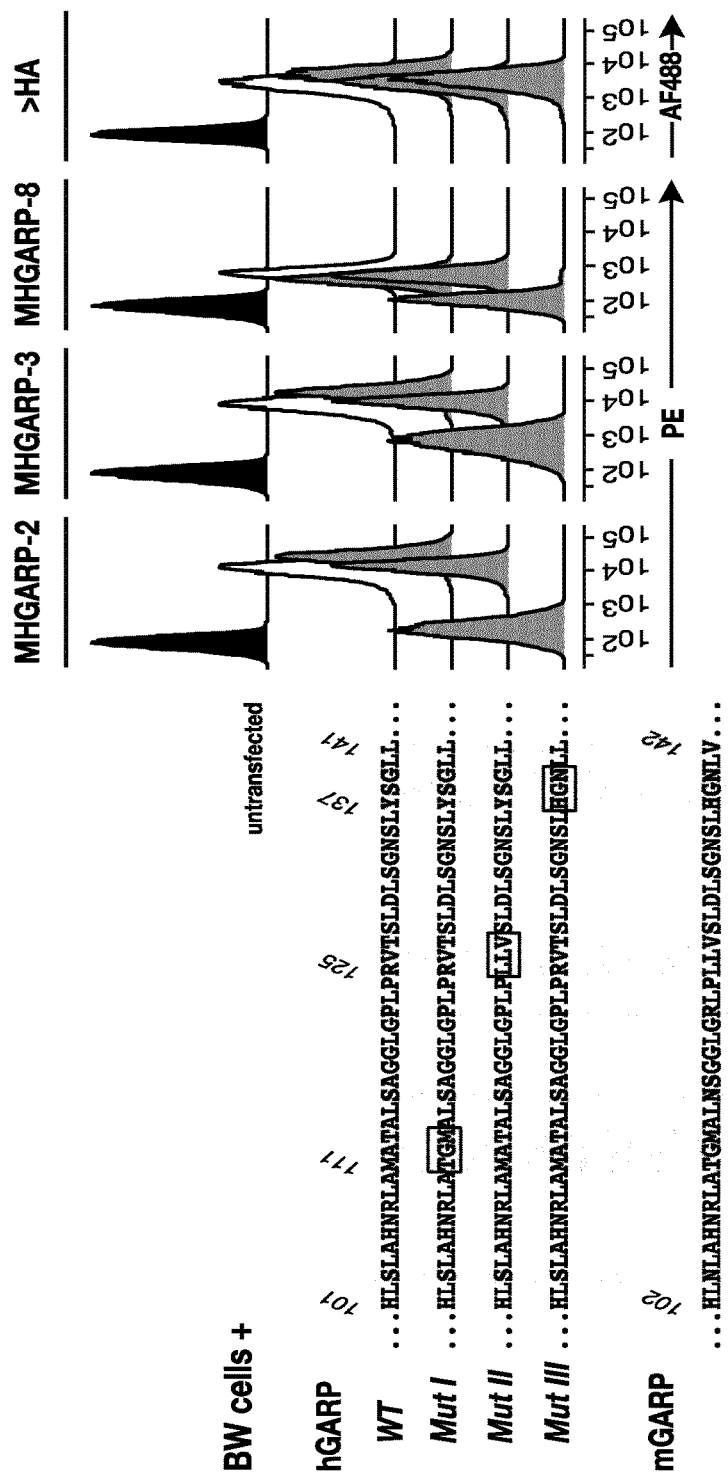

FIG. 5. Binding of MHGARP-2, -3 and -8 requires amino-acids 137-138-139 of hGARP. Parental BW5147 T cells (BW untransfected) or clones stably transfected with plasmids encoding HA-tagged forms of hGARP were stained with the indicated >hGARP or >HA antibodies, and analyzed by flow cytometry. The HA-tagged forms of hGARP tested here comprised aa 20-662 of hGARP (wild type, WT), or aa 20-662 of hGARP in which groups of 3 amino-acids located in region 101-141 were replaced by the amino-acids found in the corresponding region of mGARP (Mut I, Mut II and Mut III). Amino-acid sequences of region 101-141 of hGARP-WT (SEQ ID NO: 53), -Mut I (SEQ ID NO: 54), -Mut II (SEQ ID NO: 55), -Mut III (SEQ ID NO: 56) and mGARP (SEQ ID NO: 57) are indicated on the left. Amino-acids that differ between human and mouse GARP are highlighted by grey vertical boxes, and amino-acids mutated in Mut I, Mut II and Mut III are indicated by black horizontal boxes.

Figure 6:
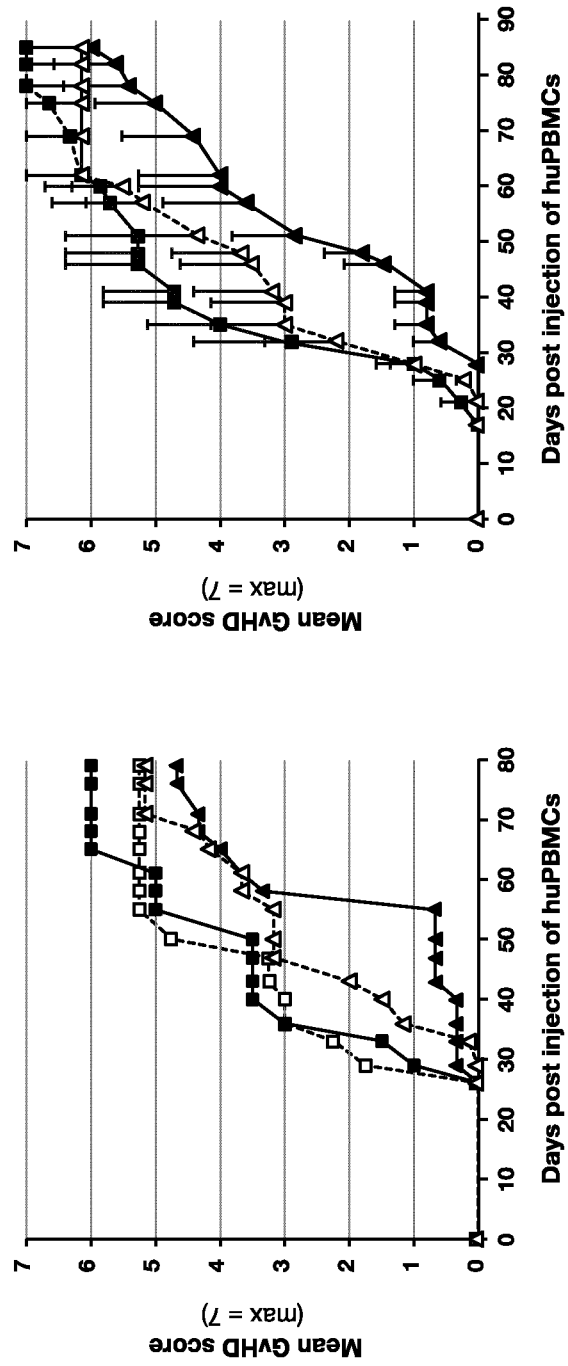

FIG. 6. MHGARP8 inhibits Treg function in vivo. On day 0, the indicated groups of NSG mice received i.v. injections of human PBMCs, in combination or not with human Tregs. Mice from groups III and IV were treated with the MHG-ARP8 antibody, injected i.p. once a week, starting on day −1. Objective signs of GvHD development in the recipient mice were monitored bi-weekly. A GvHD score was established based on weight loss (0: <10%; 1: 10%-20%; 2: >20%; 3: >30%), anemia (0: red or pink tail; 1: white tail), posture (0: normal; 1: hump), general activity (0: normal; 1: limited), hair loss (0: no hair loss; 1: hair loss) and icterus (0: white or red tail; 1: yellow tail). Maximum disease severity or death corresponded to a score of 7. (A) Experiment 1. Values represent mean scores. (B) Experiment 2. Values represent mean scores+SEM.

Figure 7A:
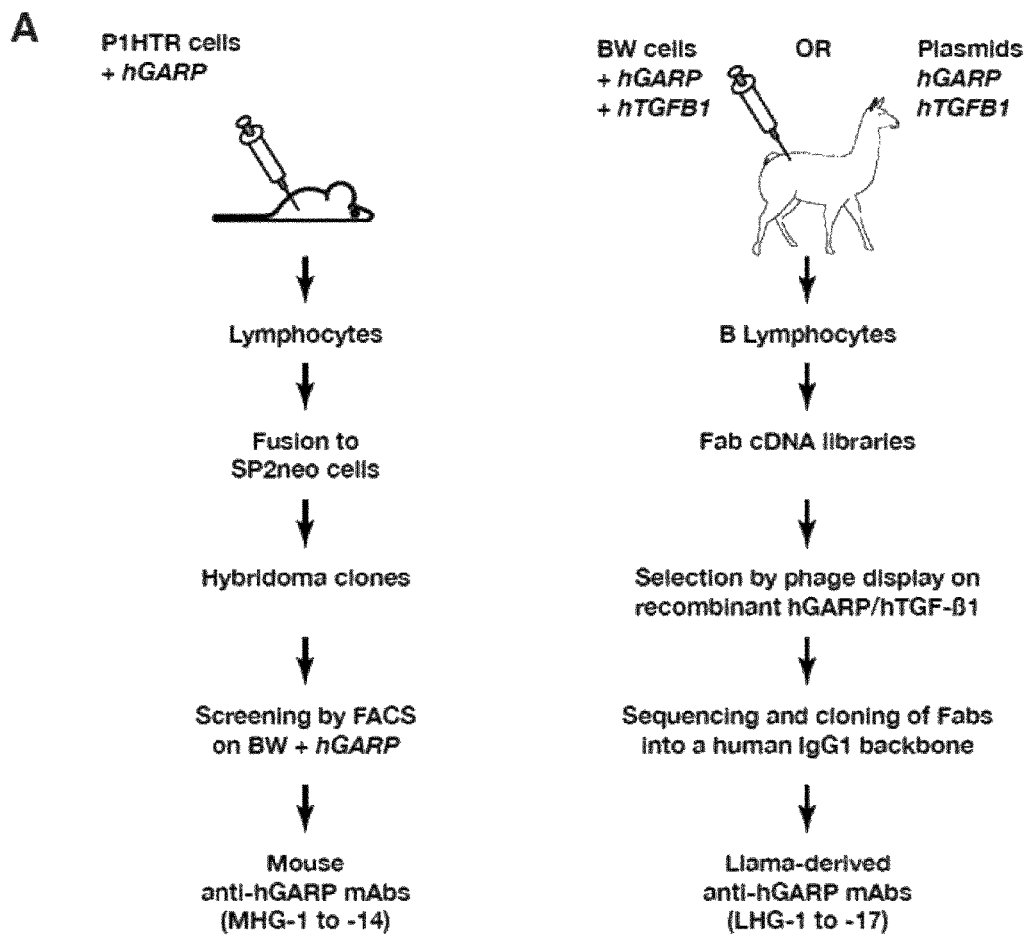
Figure 7B:
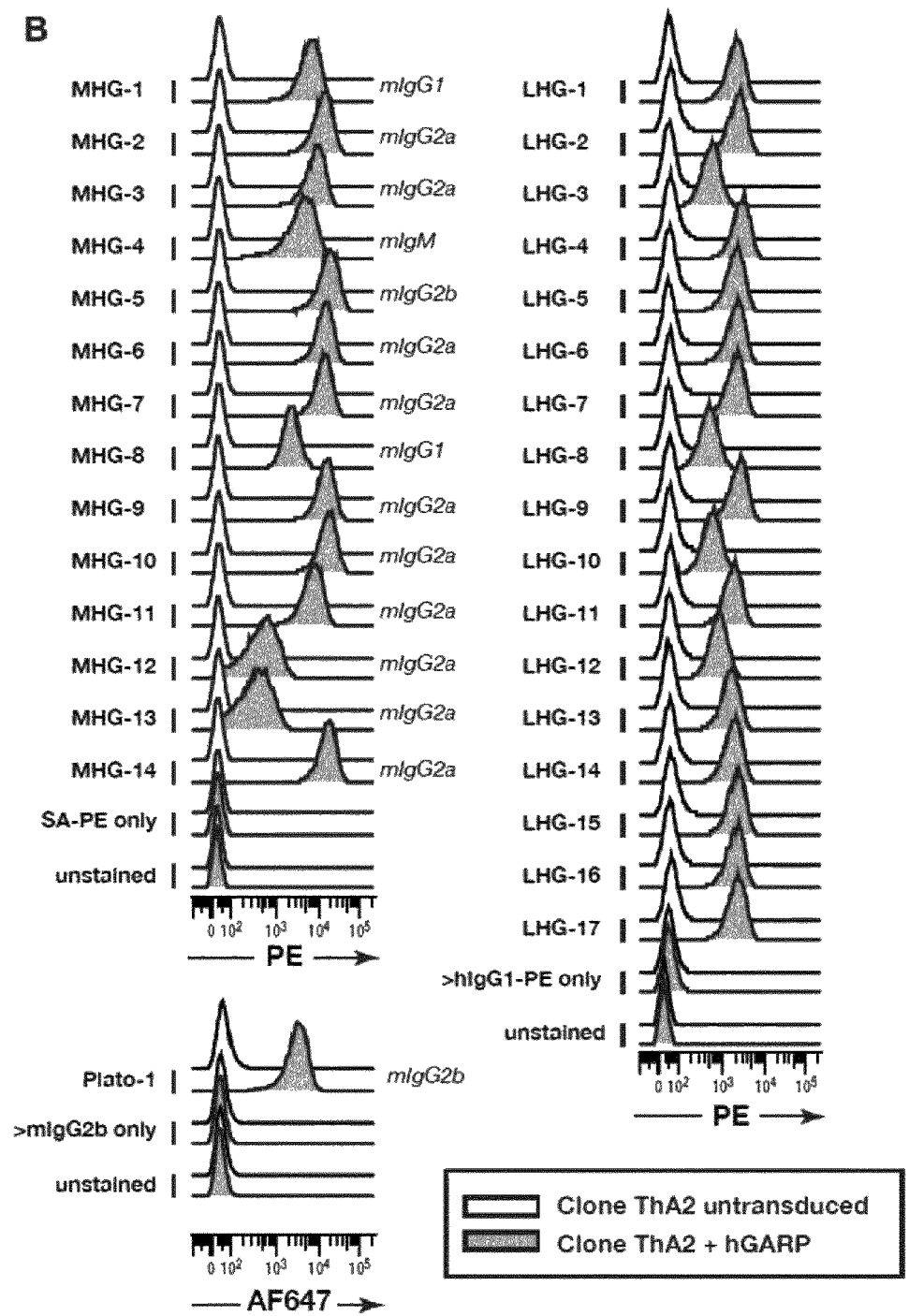

FIG. 7. New anti-hGARP mAbs. (A) Schematic representation of the experimental strategies used to derive anti-hGARP mAbs. (B) Flow cytometry analyses of clone ThA2 (human CD4+Th cells which do not express hGARP), or ThA2 cells transduced with hGARP, after staining with biotinylated MHG-1 to -14 mAbs and streptavidin coupled to PE (SA-PE), with LHG-1 to -17 mAbs and a secondary anti-hIgG1 antibody coupled to PE, or with a commercially available mouse anti-hGARP mAb (clone Plato-1) and a secondary anti-mIgG2b antibody coupled to AF647.

FIG. 8. Immune responses from immunized llamas. (A) shows immune responses from DNA immunized llamas. (B) shows immune responses from llamas immunized with BW cells expressing hGARP/hTGFβ.

Figure 9:
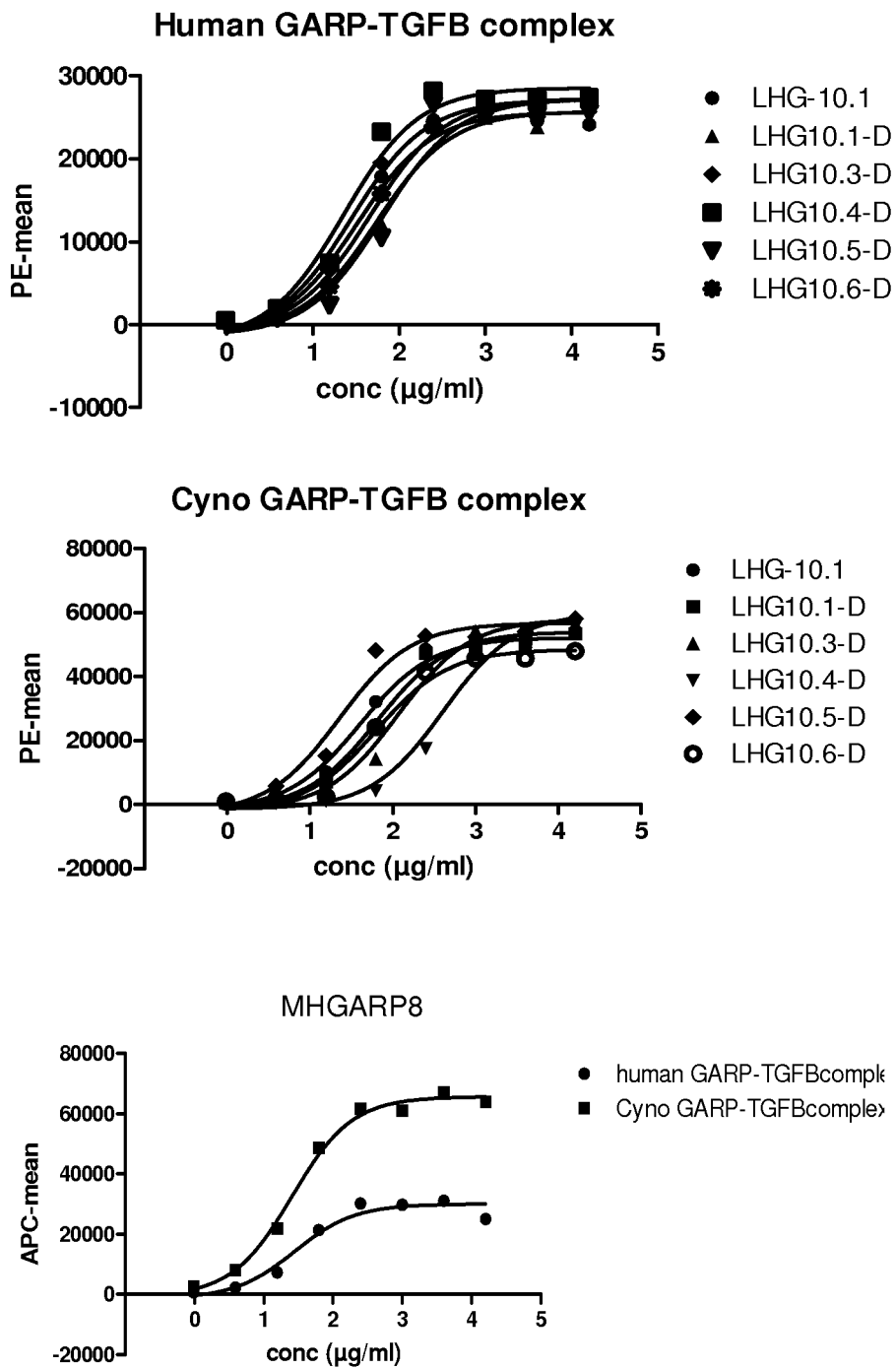

FIG. 9. Cross-reactivity to cynomolgus GARP-TGFβ measured on cells by FACS. 293E cells were transfected with human/cyno GARP and human/cyno TGFB. LHG-10-D and the affinity optimized variants are cross-reactive with cynomolgus GARP-TGFB.

FIG. 10. Sequences of LHG-10 antibodies and its shuffle variants. FIG. 10 discloses SEQ ID NOS 34, 35, 35, 37, 39, 36, 38, 35, 37, 39, 36, 38, 13-15 and 19-33, respectively, in order of appearance.

FIG. 11. MHGARP8 and LHG-10 inhibit production of active TGF-β by human Tregs. After a short in vitro amplification, human CD4+CD25hiCD12710 cells (Tregs) were re-stimulated with anti-CD3/CD28 coated beads during 24 hours, in the presence or absence of the indicated mAbs (10 µg/ml). Cells lysates were analyzed by Western Blot with antibodies against phosphorylated SMAD2 (pSMAD2), as a read-out for active TGF-β production, or β-ACTIN (loading control).

Figure 12:
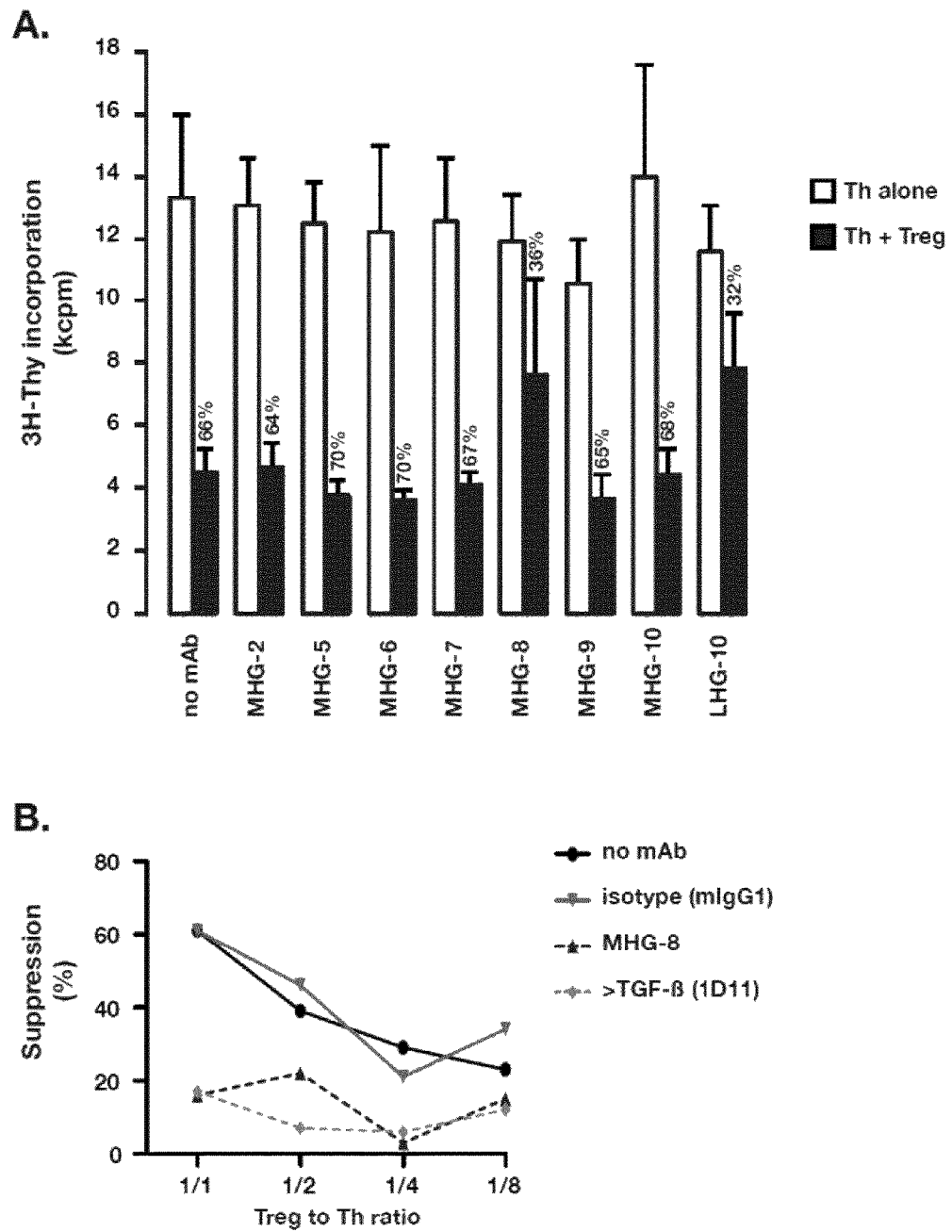

FIG. 12. MHGARP8 and LHG-10 inhibit the suppressive activity of human Tregs in vitro. (A) Freshly isolated human CD4+CD25−CD127hi cells (Th; $2 \times 10^4$ per microwell) were seeded alone or with clone Treg A1 (Stockis, J. et al. Eur. J. Immunol. 2009, 39:869-882) at a 1/1 Treg to Th ratio. Cells were stimulated with coated anti-CD3 and soluble anti-CD28, in the presence or absence of the indicated anti-hGARP mAbs (10 µg/ml). 3H-Thymidine (3H-Thy) was added during the last 16 hours of a 4-day culture and incorporation was measured in a scintillation counter as a read-out for proliferation. Bar histograms indicate kcpm (means of triplicates+SD). Clone Treg A1 did not proliferate in the absence of Th cells (Treg alone: 0.5±0.04 kcpm). Suppression of Th proliferation in the presence of Tregs is indicated above each black bar, and is calculated as follows: % suppression=1−(kcpm (Th alone)/kcpm (Th+Treg). (B) Clone ThA2 cells (Th; $1 \times 10^4$ per microwell) were seeded with clone Treg A1 at the indicated Treg to Th ratios, in the presence or absence of MHGARP8 (MHG-8), anti-hTGF-β1 mAb (clone 1D11) or an isotype control (mIgG1). Stimulation, measure of proliferation and calculation of suppression were performed as in A.

Figure 13:
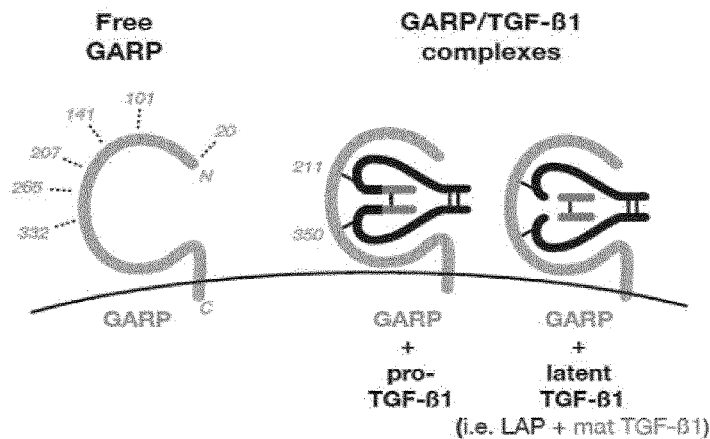

FIG. 13. Forms and regions of GARP bound by anti-GARP mAbs. (A) Schematic representations of GARP and GARP/TGF-β complexes. Protein GARP is represented by a thick curved grey line. Numbers indicate amino-acid positions. TGF-β is represented with the Latency Associated Peptide (LAP) as thick black lines, and the mature TGF-β1 peptide as thick straight grey lines. Thin black lines represent inter-chain disulfide bonds. (B) Classification of anti-hGARP mAbs based on their binding requirements.

FIG. 14. Three groups of anti-hGARP mAbs bind free GARP only, free GARP and GARP/TGF-β1 complexes, or GARP/TGF-β1 complexes only, respectively. (A) Cell lysates of BW cells transfected with hGARP and hTGFB1 were immunoprecipitated with the indicated anti-hGARP mAbs. Total lysates (BW+hGARP+hTGFB1 or untransfected controls) and IP products were analysed by Western Blot with antibodies against hGARP (clone Plato-1), LAP or the mature TGF-β peptide. (B) Flow cytometry analyses of 293T cells, untransfected or transfected with hGARP, hTGFB1 or both, and stained as indicated with anti-LAP-APC, biotinylated MHG mAbs and streptavidin-PE, clone Plato-1 and >mIgG2b-AF647, or LHG mAbs and >hIgG1-PE.

Figure 15A:
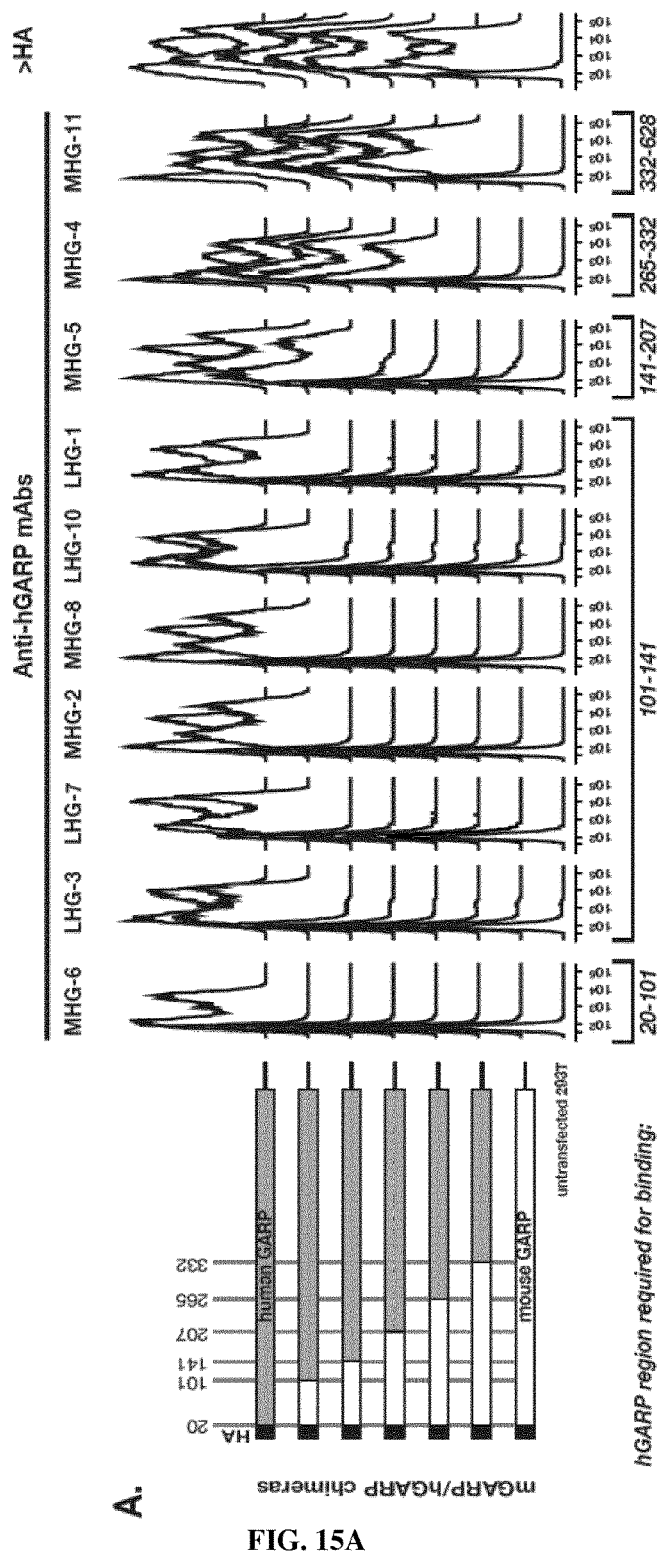
Figure 15B:
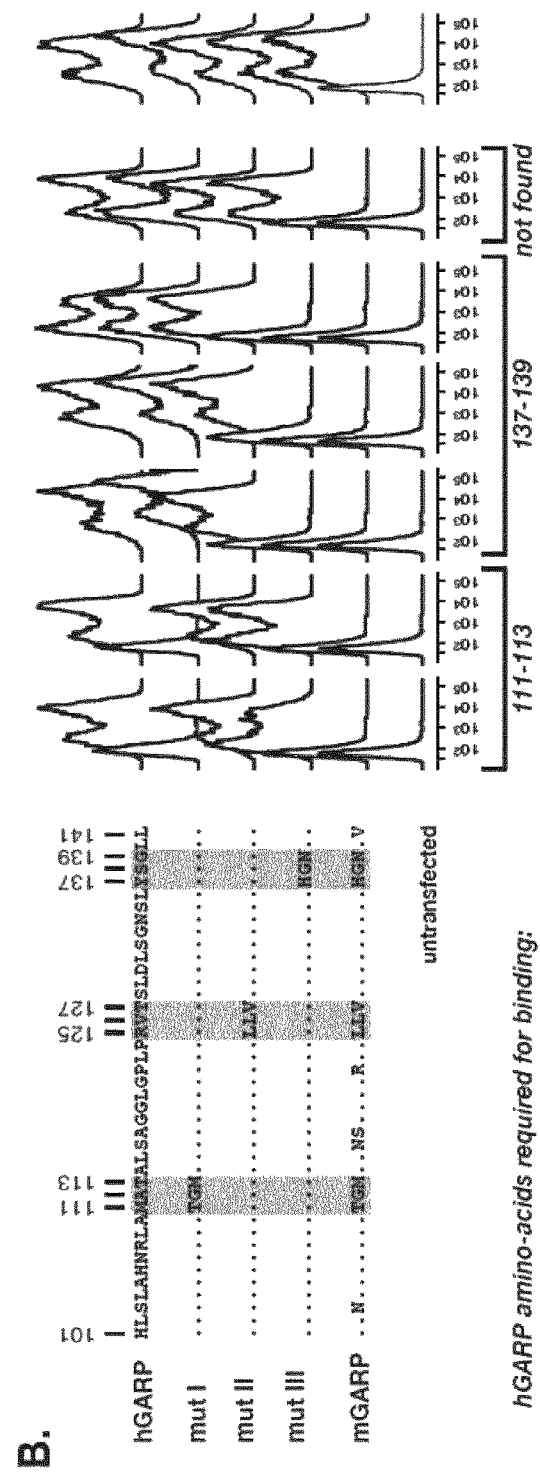

FIG. 15. Amino-acids of hGARP required for binding by MHG and LHG mAbs. (A) Flow cytometry analyses of 293T cells transfected with plasmids encoding the HA-tagged mGARP/hGARP chimeras schematized on the left (numbers represent amino-acid positions in hGARP). Cells were stained with biotinylated MHG mAbs and streptavidin-PE, LHG mAbs and >hIgG1-PE, or anti-HA and >mIgG1-AF647. hTGFB1 was co-transfected with mGARP/hGARP chimeras for the analyses of mAbs that bind hGARP/hTGF-β1 complexes only (LHG-3, MHGARP8 (MHG-8), LHG-10). (B) As above, except that 293T cells were transfected with plasmids encoding mutated forms of full-length HA-tagged hGARP. In each mutant, 3 amino-acids of hGARP were replaced by the 3 amino-acids found in mGARP, as illustrated in the alignment on the left (numbers represent amino-acid positions in hGARP). FIG. 15B discloses SEQ ID NOS 53-57, respectively, in order of appearance.

FIG. 16. Inhibition of human Treg function by anti-hGARP in vivo. (A) shows the protocol on day 0, the indicated groups of NSG mice received i.v. injections of human PBMCs, in combination or not with human Tregs. (B) shows the results of 4 independent experiments (I to IV), performed with cells from donors A, B or C, with the indicated numbers of mice per group (n). Disease onset is the day when mean disease score becomes ≥1, and is indicated for 3 experimental groups in which mice were grafted with PBMCs only (group a), PBMCs and Tregs (group b), or PBMCs and Tregs and treated with MHGARP8 (MHG-8) (group c). (C) Detailed results from experiment IV, showing the evolution of mean disease score (left) and survival curves (right) in the indicated groups of mice. Statistical significance of differences between groups b (PBMCs+Tregs) and c (PBMCs+Tregs+MHG-8) were calculated using 2-way Anova analysis for progression of disease scores (p=0.0001), and a Log-rank (Mantel-Cox) test for survival (p=0.0027).

EXAMPLES

The present invention is further illustrated by the following examples.

Example 1: New Monoclonal Antibodies Directed Against Human GARP (>hGARP Monoclonals)

DBA/2 or Balb/c mice were immunized with murine P1HTR cells transfected with human GARP. Sera from immunized mice were tested for the presence of >hGARP antibodies, by screening for binding to hGARP-expressing BW cells by FACS. Splenocytes from mice with high titers of >hGARP antibodies were fused to SP2/neo cells. Hybridomas were selected in HAT medium and cloned under limiting dilution. Supernatants of +/−1600 hybridoma clones were screened by FACS for the presence of antibodies binding to hGARP-expressing BW cells. We identified 38 clones producing >hGARP monoclonals in this screening. Nine clones were selected and amplified for large scale-production and purification of 9 new >hGARP monoclonals (MHGARP1 to 9).

Figure 1:
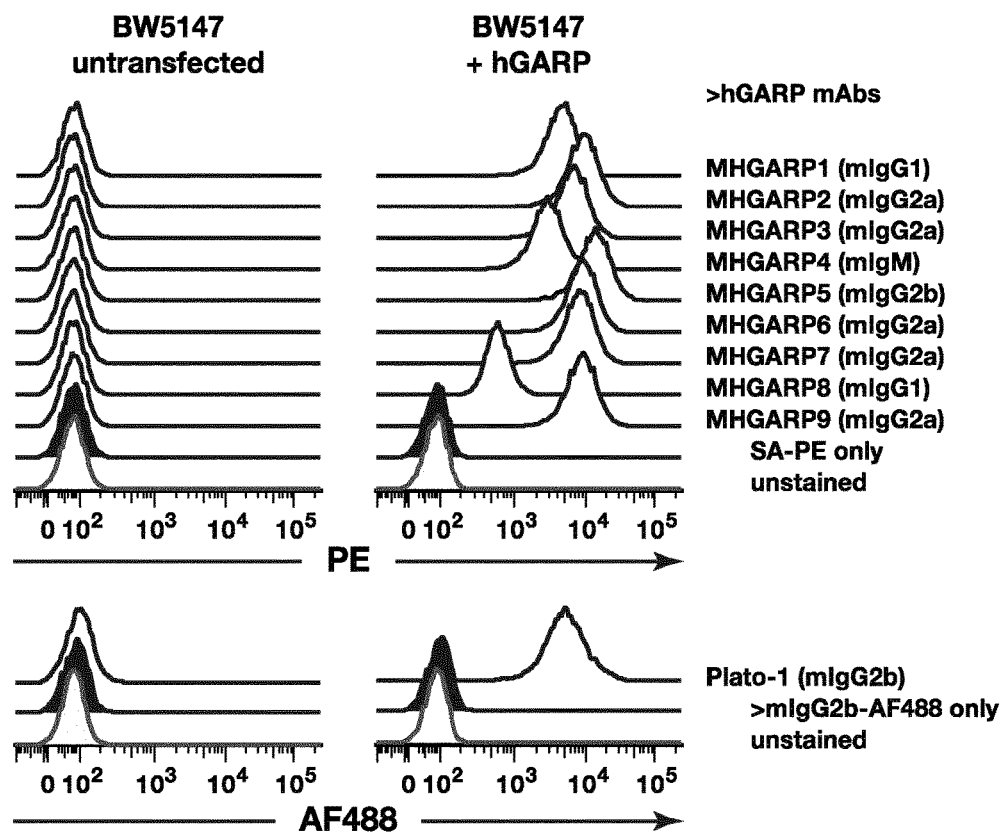
FIG. 1. New monoclonal antibodies that recognize human GARP on the cell surface. Murine BW5147 T cells, transfected or not with human GARP (hGARP) were stained with biotinylated in-house >hGARP antibodies (MHGARP1 to 9) and streptavidin-PE (SA-PE, top panels), or with a commercial anti-hGARP antibody (clone Plato-1) and secondary anti-mouse IgG2b coupled to AlexaFluor 488 (AF488, bottom panels).

As shown in FIG. 1, MHGARP1 to 9 bind to murine BW5147 cells transfected with hGARP, but not to untransfected cells. MHGARP1 to 9 also bind 293T cells transfected with hGARP and two human T cells lines (clone Th A2 and Jurkat) transduced with a hGARP-encoding lentivirus, but not the corresponding parental cells (not shown). This recognition pattern is identical to that of a commercially available >hGARP mAb (clone Plato-1) used here as a positive control. These results show that MHGARP1 to 9 recognize hGARP on cell surfaces.

As shown in FIG. 7, 5 additional MHGARP antibodies were produced and purified. MHGARP antibodies (MHG-1 to -14 on the figure) do not bind clone ThA2 (human CD4+T helper cells, which do not express hGARP), but bind ThA2 transduced with hGARP.

Example 2: MHGARP8, but None of 12 Other >hGARP Monoclonals, Inhibits Active TGF-βProduction by Human Treg Cells A human Treg clone (1E+06 cells/ml) was stimulated in serum-free medium with coated anti-CD3 (1 µg/ml) and soluble anti-CD28 (1 µg/ml) antibodies, in the presence or absence of 20 µg/ml of an >hGARP monoclonal antibody. Thirteen >hGARP monoclonals were tested in this assay: our 9 new monoclonals (MHGARP1 to 9), and commercially available antibody clones Plato-1 (Enzo Life Sciences, catalog No. ALX-804-867), 272G6 (Synaptic Systems, catalog No. 221 111), 50G10 (Synaptic Systems, catalog No. 221 011) and 7B11 (BioLegend, catalog No. 352501). Cells were collected after 24 hours, lysed and submitted to SDS-PAGE under reducing conditions. Gels were blotted on nitrocellulose membranes with the iBlot system (Life Technologies). After blocking, membranes were hybridized with primary antibodies directed against phosphorylated SMAD2 (pSMAD2, Cell Signaling Technologies) or β-ACTIN (SIGMA), then hybridized with secondary HRP-coupled antibodies and revealed with Enhanced ChemiLuminescent (ECL) substrate (ThermoFisher Scientific). The presence of pSMAD2 indicates production of active TGF-β1 by the stimulated Treg clone. ECL signals were quantified by measuring the density of the 55 kDa pSMAD2 and 40 kDa β-ACTIN bands on autoradiographs, using the Image J software.

Figure 2:
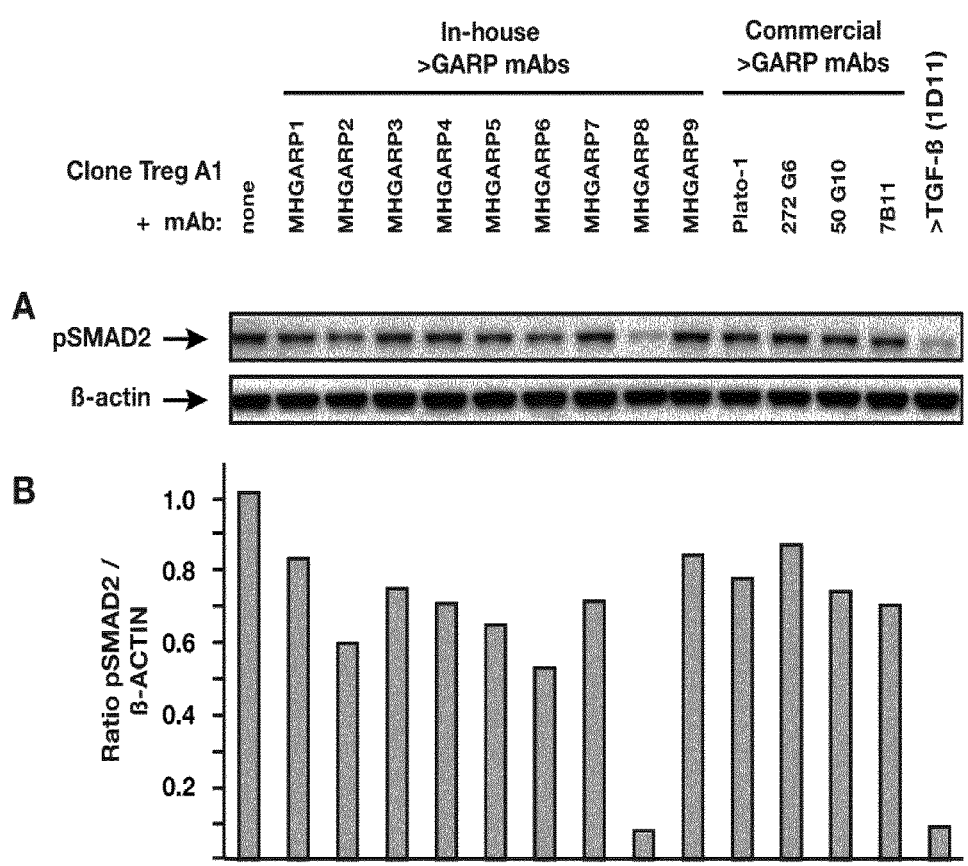
FIG. 2. MHGARP8 inhibits active TGF-β production by a human Treg clone. Clone Treg A1 was stimulated during 24 hours with >CD3/CD28 antibodies, alone or in the presence of the indicated >hGARP mAbs (20 µg/ml). (A) Cell lysates were analyzed by WB with >pSMAD2 and >β-ACTIN antibodies. (B) Quantification of ECL signals from WB shown in A.

To examine whether hGARP is required for active TGF-β production by TCR-stimulated Treg cells, we stimulated a human Treg clone through its T cell receptor (TCR), alone or in the presence of >hGARP mAbs. Active TGF-β produced by stimulated Tregs triggers an autocrine signal, which leads to the phosphorylation and activation of SMAD2 and SMAD3 transcription factors. We measured the presence of phosphorylated SMAD2 (pSMAD2) by Western Blot (WB), as read-out for active TGF-β production by the stimulated Treg clone. As shown in FIG. 2, pSMAD2 was reduced more than 10 fold in the presence of MHGARP8. This reduction is similar to that observed in the presence of an anti-TGF-β mAb, used here as a positive control. None of the 12 other >hGARP mAbs (8 other in-house produced MHGARP and 4 commercially available anti-GARP antibodies) inhibited active TGF-β production by the Treg clone. Altogether, our data demonstrate that GARP is required for active TGF-β production by human Tregs, as MHGARP8, an antibody directed against hGARP, prevented active TGF-β production.

Example 3: MHGARP8, but not Other >hGARP mAbs, Recognizes a Conformational Epitope that Requires the Presence of TGF-β

Mapping the Regions Recognized by >hGARP Monoclonals
Murine BW5147 T cells were electroporated with plasmids encoding the HA-tagged proteins schematized in FIG. 3A, corresponding to hGARP, mGARP or mGARP/hGARP chimeras. Stable clones selected in neomycin were stained with biotinylated anti-hGARP antibodies (>hGARP1 to 9)

and streptavidin-PE, with the commercial anti-hGARP antibody (clone Plato-1) and a secondary anti-mIgG2b-AF488, or with an anti-HA antibody and secondary anti-mouse IgG1-AF488. Histograms are gated on live cells. Black histograms show signals on untransfected BW cells, white histograms show signals on BW cells expressing the HA-tagged hGARP, and grey histograms show signals on BW cells expressing HA-tagged mGARP or mGARP/hGARP chimeras.

Parental BW5147 T cells (BW non-transfected) or clones stably transfected with hGARP alone (BW+hGARP) or with hTGFB1 (BW+hGARP+hTGF-β1) were stained with biotinylated anti-hGARP antibodies (>hGARP1 to 9) and streptavidin-PE, with the commercial anti-hGARP antibody (clone Plato-1) and a secondary anti-mIgG2b-AF488, or with >mLAP-AF647 or >hLAP-APC antibodies.

We investigated the mechanism by which MHGARP8, but not other >hGARP mAbs, inhibits active TGF-β production by Tregs. We hypothesized that MHGARP8 may recognize an epitope in hGARP that is distinct from the epitopes recognized by the other >hGARP mAbs.

With the exception of MHGARP-1, our MHGARP mAbs do not recognize murine GARP (mGARP). We thus constructed plasmids encoding HA-tagged hGARP, mGARP or hGARP/mGARP chimeras to map the hGARP regions recognized by our mAbs. We transfected murine BW cells and derived stable clones expressing the HA-tagged proteins (schematically represented in FIG. 3). All clones expressed similar levels of HA-tagged protein on the surface, as indicated by similar fluorescence intensities after staining with an >HA mAb (FIG. 3A). As expected, all the MHGARP mAbs bound to the clone expressing HA-tagged hGARP, whereas none, except MHGARP-1, bound to the clone expressing HA-tagged mGARP. Four groups of mAbs emerged from the analysis of binding to the HA-tagged hGARP/mGARP chimeras (FIG. 3A). Monoclonal antibodies in the first group (MHGARP-6, -7 and -9) bound none of the chimeras, indicating that they recognize an epitope located between aa 20 and 101 of hGARP (region 20-101). mAbs in the second group (MHGARP-2, -3 and -8) bound to only 1 of the 5 chimeras, and thus recognize an epitope in region 101-141. A third group comprises MHGARP-5, which bound to 2 of the chimeras and therefore recognizes region 141-207. This group probably also contains MHGARP-1, which is cross-reactive but bound these 2 chimeras more efficiently than it bound mGARP or the 3 other chimeras. Finally, mAbs in the fourth group (MHGARP-4 and Plato-1) bound 4 of the 5 chimeras, and thus recognize region 265-333.

Based on the above, we grouped the >hGARP mAbs into 4 families of antibodies that recognize 4 distinct regions of the hGARP protein. MHGARP-8, which displays neutralizing activity, binds to region 101-141. This region is also recognized by MHGARP-2 and -3, which are not neutralizing. Therefore, the ability to bind region 101-141 is not sufficient to confer neutralizing activity.

To further define the epitopes recognized by MHGARP-2, -3 and -8, we compared the binding of the >hGARP antibodies to clones of BW cells expressing hGARP alone (BW+hGARP), or hGARP and hTGF-β1 (BW+hGARP+hTGF-β1). With the notable exception of MHGARP8, all >hGARP antibodies stained BW+hGARP+hTGF-β1 with the same intensity as BW+hGARP, indicating that the two clones express the same levels of hGARP on the cell surface. The MHGARP8 antibody in contrast, stained BW+hGARP+ hTGF-β1 more intensely than BW+hGARP (FIG. 3B). This indicates that although hGARP levels are similar on the two clones, the epitope recognized by MHGARP8 is more abundant on BW+hGARP+hTGF-β1 than on BW+hGARP cells.

A plausible explanation for this observation is that the epitope recognized by MHGARP8 appears only when hGARP is bound to murine (m) or human (h) TGF-β1. This could be due to one of two mechanisms: either the epitope comprises amino-acids from both hGARP and TGF-β1 (mixed conformational epitope), or it comprises amino-acids from hGARP only, but that adopt a different conformation in the presence of TGF-β1 (binding-induced conformational epitope). BW cells express murine TGF-β1, and murine TGF-β1 binds to hGARP (FIG. 3B). Therefore, binding of MHGARP8 to BW+hGARP (in the absence of transfected hTGF-β1) could be due to recognition of hGARP/mTGF-β1 complexes.

Figure 3C:
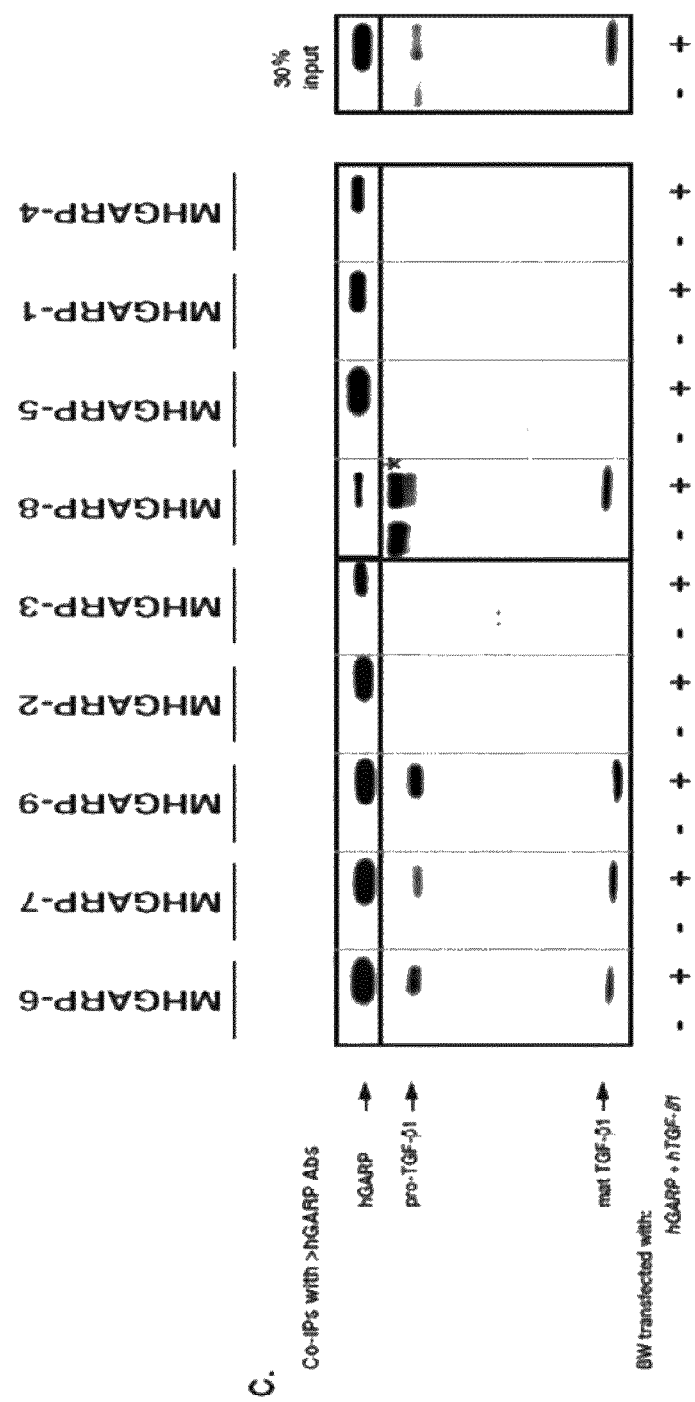
FIG. 3. (A) Regions in the hGARP protein required for binding by >hGARP antibodies. Murine BW5147 T cells expressing the HA-tagged proteins schematized on the left were stained with >hGARP (MHGARP1 to 9, as indicated on top of the figure) or >HA antibodies, and analyzed by flow cytometry. Histograms are gated on live cells. Based on the FACS results, regions required for binding by the various MHGARP mAbs were identified and are indicated by horizontal bars above the representations of the HA-tagged chimeras.

To explore the hypothesis that MHGARP8 recognizes GARP when it is bound to TGF-β1, we performed co-immunoprecipitation experiments. We used the different anti-GARP antibodies to immunoprecipitate GARP from BW+hGARP+hTGF-β1 cells, then checked if TGF-β was co-immunoprecipitated with GARP. As shown in FIG. 3C, all anti-GARP antibodies efficiently immunoprecipitated GARP (FIG. 3C, top panels). Co-immunoprecipitation of TGF-β1 was observed with MHGARP-6, -7, -8, and -9 mAbs, indicating that these antibodies bind GARP bound to TGF-β1. In contrast, MHGARP-1, -2, -3, -4 and -5 immunoprecipitated GARP as efficiently as the other anti-GARP mAbs, but they did not co-immunoprecipitate TGF-β(FIG. 3C, bottom panels). This indicates that MHGARP-1, -2, -3, -4 and -5 recognize free GARP, but not GARP that is bound to TGF-β. It is important to note that MHGARP-2 and -3, which require the $GARP_{101\text{-}141}$ region for binding, recognize only free GARP, whereas neutralizing MHGARP8, which also requires $GARP_{101\text{-}141}$, recognizes GARP bound to TGF-β.

To confirm this observation, we used 293T cells, which express low levels of endogenous TGF-β1, to co-transfect hGARP with increasing amounts of hTGFB1 (FIG. 3D). Binding of MHGARP-1, -2, -3, -4 and -5 decreased dose-dependently when hTGFB1 was co-transfected with hGARP. It was completely abrogated at the highest doses of hTGFB1. This confirms that MHGARP-1 to -5 bind only free GARP. Binding of MHGARP-6, -7, and -9 was not modified by co-transfection of hTGFB1, indicating that these mAbs bind hGARP whether or not it is bound to TGF-β1 (i.e. they bind both free GARP and GARP bound to TGF-β1). In striking contrast, binding of MHGARP8 increased dose-dependently when hTGFB1 was co-transfected with hGARP. This suggests again that in contrast to all other antibodies, MHGARP8 does not bind free GARP, but only GARP bound to TGF-β1.

To demonstrate that MHGARP8 binding requires the presence of TGF-β1, we used siRNAs to silence the expression of TGFB1 in Jurkat cells transduced with hGARP (FIG. 3E). The siRNA against TGFB1 mRNA efficiently reduced expression of TGF-β 1, as illustrated by the decrease in surface LAP detected on Jurkat+hGARP cells (FIG. 3E, right panel). Reduced expression of TGF-β1 in Jurkat+ hGARP decreased the binding of the MHGARP8 antibody, but it did not modify the binding of the other anti-GARP antibodies (FIG. 3E, foreground histograms). This confirms that in contrast to the other anti-GARP antibodies, MHGARP8, does not bind free GARP, but only binds GARP in the presence of TGF-β1.

Finally, we sought to exclude the unlikely hypothesis that presentation of TGF-β on the cell surface, irrespective of hGARP expression, is sufficient for binding by MHGARP8. In other words, we sought to demonstrate that MHGARP8 recognizes a mixed or a binding-induced conformational epitope that requires expression of both hGARP and TGF-β. For this, we transfected 293T cells with constructs encoding hGARP, mGARP or the hGARP/mGARP chimeras described above, with or without a construct encoding hTGF-β1. Transfected cells were analyzed by FACS to measure binding of the MHGARP8 antibody, and presentation of hTGF-β1 on the cell surface with an >hLAP antibody (FIG. 4). By comparison to unstransfected cells, transfection of hGARP, mGARP or hGARP/mGARP constructs alone (no hTGFB1) induced low levels of surface LAP, due to low levels of endogenous hTGFB1 expression (FIG. 4A, left). Surface LAP levels dramatically increased upon transfection of hTGFB1 in cells transfected with hGARP, mGARP, or any hGARP/mGARP construct (FIG. 4B, left histogram). This indicates that hTGF-β1 is presented on the cell surface by hGARP, by mGARP and by all the hGARP/mGARP chimeras. Importantly, MHGARP8 bound only to the surface of cells transfected with hGARP, or with the hGARP/mGARP constructs encoding amino-acids 101 to 141 of hGARP (FIGS. 4A and 4B, right). It did not bind to cells transfected with hTGFB1 and mGARP, nor to cells transfected with hTGFB1 and hGARP/mGARP constructs that do not encode hGARP101-141 (FIG. 4B, right), although these cells presented high levels of LAP on their surface (FIG. 4B, left). This demonstrates that presentation of TGF-β1 on the cell surface (by mGARP or hGARP/mGARP chimeras) is not sufficient for binding by MHGARP8. Binding of MHGARP8 requires the presence of both hGARP (region 101-141) and TGF-β1 on the cell surface.

As indicated above, MHGARP8 does not bind mGARP. Its binding to hGARP requires a region comprising amino-acids 101 to 141. To further define the epitope recognized by MHGARP8, we compared the sequences of region 101-141 in human and murine GARP. In this region, only 13 amino-acids differ between hGARP and mGARP (FIG. 5, amino-acids highlighted by grey boxes). We constructed 3 HA-tagged mutant forms of hGARP. In each mutant (Mut I, Mut II and Mut III), 3 consecutive amino-acids were replaced by the corresponding amino-acids of the mGARP protein (FIG. 5, black boxes). We derived stable clones of BW cells transfected with these HA-tagged forms of wild type (WT) or mutant hGARP. All clones expressed similar levels of HA-tagged protein on the surface, as demonstrated by staining with an >HA antibody (FIG. 5, histograms on the right). We then analyzed the clones after staining with MHGARP-2, -3 and -8, i.e. antibodies which require region 101-141 of hGARP for binding. The three antibodies bound to cells expressing WT, Mut I and Mut II forms of hGARP. In contrast, binding was greatly reduced on cells expressing the Mut III form of hGARP, indicating that MHGARP-2, -3 and -8 require amino-acids 137-138-139 of hGARP for binding.

Altogether, our data show that MHGARP8 is the only available anti-GARP antibody that inhibits active TGF-β1 production by human Tregs. This neutralizing activity is linked to binding of MHGARP8 to an epitope that is distinct from those bound by all other anti-GARP antibodies: binding of MHGARP8 requires both region 101-141 of hGARP and the presence of hTGF-β, whereas binding of non-neutralizing antibodies require other regions of hGARP (for MHGARP-1, -4, -5, -6, -7 and -9), or occurs only in the absence of TGF-β1 (for MHGARP-2 and -3). In region hGARP101-141, amino-acids 137 to 139 are required for the binding of MHGARP-2, -3 and -8.

Affinity of MHGARP8 antibody to immobilized shGARP-TGFβ was measured by BIACOR analysis: Kd of said antibody is 0.2 nM.

Example 4: MHGARP8 Inhibits Human Treg Cell Function In Vivo

To examine whether MHGARP8 also inhibits human Tregs in vivo, we used a model of xenogeneic GvHD induced by transfer of human PBMCs (Peripheral Blood Mononuclear Cells) into immuno-compromised NOD-Scid-IL2Rg$^{-/-}$ (NSG) mice. NSG mice lack functional T, B and NK cells. This allows efficient engraftment of human hematopoietic stem cells (HSCs), which proliferate and generate a functional human immune system in recipient mice. When human PBMCs are used instead of HSCs, efficient engraftment of T cells occurs, but is soon accompanied by the development of a xenogeneic Graft-versus-Host Disease (GvHD). In this model, GvHD results from the activity of human donor cytotoxic T lymphocytes that recognize tissues of the recipient NSG mice as foreign (Shultz, et al. Nature 2012, 12:786-798). The severity of the GvHD can be decreased by co-transferring human Treg cells with human PBMCs (Hannon et al. Transfusion 2014).

Human PBMCs were isolated from total blood of a hemochromatosis donor by centrifugation on density gradients (Lymphoprep™), and frozen for later use. Autologous Tregs were generated as follows: CD4+ T cells were isolated from the blood of the same donor using the RosetteSep™ Human CD4+ T Cell Enrichment Cocktail (StemCell Technologies) and stained with anti-CD4, anti-CD25 and anti-CD127 antibodies coupled to fluorochromes. CD4+CD25hiCD12710 cells were sorted by flow cytometry (>99% purity) then stimulated with anti-CD3/CD28 coated beads (Dynabeads® Human T-Activator CD3/CD28 for T-Cell Expansion and Activation, Life Technologies) in the presence of IL-2 (120 IU/ml) during 14 days. These expanded Treg cells were frozen for later use.

NSG mice were irradiated (2.5 Gy) on day −1, then injected in the tail vein with human PBMCs (2.7×106 per mouse) alone, or mixed with expanded human Tregs (1.4× 106 per mouse) on day 0. Mice also received weekly i.p. injections of MHGARP8 antibody (400 µg on day −1 (day minus 1), 200 µg at later time points), or control PBS. Mice were monitored bi-weekly for GvHD development as indicated in the text.

We transferred human PBMCs with or without Tregs in NSG mice, and treated the mice with i.p. injections of MHGARP8 antibody or control PBS. The large number of human Treg cells required for the transfers were obtained through short in vitro amplification of CD4+CD25+CD12710 cells sorted from human PBMCs by flow cytometry. Objective signs of GvHD development in the recipient mice were monitored bi-weekly. We performed two independent experiments, which yielded similar results. In experiment 1 (FIG. 6A), signs of GvHD (mean score ≥1) appeared 29 days after injection of human PBMCs (group I; n=2). Disease severity increased quickly, and one of the 2 mice was euthanized for ethical reasons on day 55. In mice injected with PBMCs and Tregs (group II; n=3), the appearance of GvHD was delayed by comparison to PBMCs alone (mean score ≥1 reached after 58 days). This indicates that Tregs, as expected, partially protected NSG mice against GvHD. Importantly, treatment of mice receiving PBMCs and Tregs with the MHGARP8 antibody (group III, n=6) aggravated the disease: signs of GvHD appeared earlier (36 days) than in mice from group II. The effect of MHGARP8 appears to depend on the presence of Tregs, as no difference in disease score was observed between mice receiving PBMCs only (group I) or PBMCs and MHGARP8 (group IV; n=4). We repeated this experiment with a larger number of mice per group (FIG. 6B). Again, co-injection of Tregs with PBMCs delayed the appearance of GvHD by comparison to PBMCs alone (day 46 in group II versus day 28 in group I), and treatment with the MHGARP8 antibody aggravated GvHD in mice receiving PBMCs and Tregs (day 28 in group III) by comparisons to untreated mice (day 46 in group II). Altogether, this shows that MHGARP8 inhibits the immune-suppressive function of human Tregs in vivo.

Example 5: New Anti-hGARP Monoclonal Antibodies (mAbs) Using Immunization of Llamas Approach Production of Recombinant Soluble GARP-TGFβ1 Complex Human and murine GARP-TGFβ1 complex was produced as a soluble complex using a truncated GARP expression construct. The human GARP protein sequence was truncated after Leucine 628, followed by a cleavable TEV-3× strep tag (EAAENLYFQGAAWSHPQFEKGAAWSH-PQFEKGAAWSHPQFEKGAA*) (SEQ ID NO: 40). Murine GARP protein sequence was truncated after leucine 629, followed by the same cleavable TEV-3× strep tag. The GARP-TGFβ1 complexes were produced by co-expression of the truncated GARP and the TGFβ1 in HEK293E cells, followed by purification via the Strep-Tag.

Immunization of Llamas

Immunizations of llamas and harvesting of peripheral blood lymphocytes (PBLs) as well as the subsequent extraction of RNA and amplification of antibody fragments were performed as described by De Haard and colleagues (De Haard H, et al., J. Bact. 187:4531-4541, 2005). Four llamas were immunized with BW cells over-expressing human GARP and TGF β1 (FIG. 7A) as confirmed by flow cytometry using MHGARP8 (MHG-8) monoclonal antibody described in this patent application. The llamas were immunized with intramuscular injections in the neck once per week for a period of six weeks. Approximately $10^7$ cells were injected into the neck muscles and Freund's incomplete adjuvant was injected in a second region located a few centimeters from the injection site of the cells. Another four llamas were immunized with a mix of human GARP cDNA and human TGFβ1 cDNA expression vectors, once per two weeks, with four repetitive injections.

Blood samples of 10 ml were collected pre- and post-immunization to investigate the immune response. Three-to-four days after the last immunization, 400 ml blood was collected for extraction of total RNA from the PBLs prepared using a Ficoll-Paque gradient and the method described by Chomczynski P, et al., Anal. Biochem. 162: 156-159, 1987. On average, RNA yields of 450 µg were achieved, which was used for random cDNA synthesis and PCR amplification of the V-regions of the heavy and the light chains (Vλ and Vκ) for construction of the Fab containing phagemid libraries as described by De Haard H et al., (J Biol Chem. 1999 Jun. 25; 274(26): 18218-30), to obtain diverse libraries of good diversity ($1-7\times10^8$).

The immune response to the GARP-TGF β1 complex was investigated by ELISA on coated recombinant soluble GARP-TGF β1 complex (1 µg/ml). Five-fold serial dilutions of sera, starting from 10% sera were prepared and 100 µl of diluted sera was added onto the coated wells and incubated for 1 hour at RT. After washing with 3×PBS/Tween, the plates were blocked with PBS supplemented with 1% casein (FIG. 8). Binding of conventional llama IgG1 to its target GARP-TGFβ was measured in ELISA using a mouse anti llama IgG1 antibody (clone 27E10, Daley L P, et al. Clin. Diagn Lab Immunol. 12, 2005) and a HRP-conjugated donkey anti-mouse antibody (Jackson) for detection.

Selections and Screenings of GARP-TGFβ1 Specific Fabs

Phage expressing Fabs were produced according to standard protocols and selections performed on immobilized recombinant soluble GARP-TGF β1 with total elution of the GARP-TGF β1 binding phage with trypsin according to standard phage display protocols.

Two to three rounds of selections were performed to enrich for human GARP-TGF β1 specific Fabs expressed by the phage. hGARP and hTGF β1 (LAP) counter selections were used to enrich for Fabs binding the hGARP-TGF β1 complexes. Individual colonies were isolated and periplasmic fractions (penis) in 96-well plates were produced by IPTG induction from all the libraries according to standard protocols.

Screening of the hGARP-TGFβ specific Fabs was performed using ELISA. hGARP-TGF β1 was immobilized on a maxisorb plate. After blocking with 1% casein in PBS for 1 h, Fab from 20 µl periplasmic extracts were allowed to bind to hGARP-TGF β1.

Characterization of Monoclonal Antibodies

GARP-TGFβ1/GARP specific clones were sequenced in the VH and the VL regions and divided into VH families based on the sequence of the CDR3 in the VH. 17 families were identified. Of each VH family identified we cloned at least one representative clone in to a full human IgG1 (LHG1-LHG17). These monoclonal antibodies were analyzed on Biacore for their binding characteristics to soluble human GARP-TGFβ1 complex. Recombinant soluble human GARP-TGFβ1 was immobilized at approximately 4,000 RU on a CM5 chip (GE Healthcare).

Binding of monoclonal antibodies to the human and cynomolgus GARP-TGFβ1 complex expressed on HEK-293 cells was analyzed by FACS. Cynomolgus GARP and cynomolgus TGFβ1 encoding sequences were cloned from a cDNA sample from cynomolgus peripheral blood lymphocytes (PBMCs). Primers were based on the predicted sequences of cynomolgus GARP (XM_005579140.1; SEQ ID NO: 41) and cynomolgus TGF β1 (XM_005589338.1; SEQ ID NO: 42) by amplification of overlapping parts of the full sequence. For both cynomolgus GARP and cynomolgus TGFβ1 three separate PCR amplicons were DNA sequence analyzed. They fully aligned with the predicted sequences. Cynomolgus GARP and cynomolgus TGFβ1 were cloned into pCDNA3.1 for transient over-expression in HEK293E cells. Binding to cynomolgus GARP-TGFβ1 was compared to binding to human GARP-TGFβ1 on FACS. LHG-10 and the shuffled variants (LHG-10.3 to LHG-10.6) can be considered as cross-reactive with cynomolgus GARP-TGFβ1 (FIG. 9).

Primers Used:

```
>cyno TGFB S1:
                                (SEQ ID NO: 43)
cgcctc CCCCATGCCG ccctccg >cyno TGFB S2:
                                (SEQ ID NO: 44)
acaattcctg gcgataccte >cyno TGFB AS1:
                                (SEQ ID NO: 45)
CTCAACCACTGCCGCACAAC >cyno TGFB AS2:
                                (SEQ ID NO: 46)
TCAGCTGCATTTGCAGGAGC
```

VK Shuffling for Improved Affinity

VK chain shuffling was used to improve the affinity of the mAb LHG-10 (FIG. 10). In this method, the heavy chain of the parental clone (VHCH1 of LHG-10) was reintroduced in the phagemid-light chain library. The heavy chain was extracted from an expression vector, which lacks the bacteriophage derived gene 3 necessary for display, to further avoid contamination of the parental light chain in the selection procedure. The heavy chain was cloned into the phagemid-light chain library and the ligated DNA was electroporated into E. coli TG1 cells to create the light chain shuffled library. The size of libraries was above $10^8$.

Affinity selections, combined with off-rate washes, were performed to select for chain shuffled Fabs with an improved affinity for human GARP-TGFβ1. A set-up was chosen where Fab expressing phages were incubated with different concentrations of recombinant soluble human GARP-TGFβ1 directly coated to the microsorb plate.

By adding the recombinant soluble human GARP-TGFβ1 in excess over the coated recombinant soluble human GARP-TGFβ1, the binding of the higher affinity phage was favored. Each round the time of washing was increased (Table 3) to select for phages with a better off-rate by washing away the lower affinity variants. Phages were eluted with trypsin and used for infection of E. coli TG1 cells. In total, 5 rounds of selection were done. In addition the amount of input phage was decreased in subsequent rounds to reduce background on the one hand and on the other hand to lower the mAb concentration thereby increasing the stringency of the selection.

TABLE 3

Parameters varied for each round of selection for VK shuffling

|  | RI | RII | RIII | RIV | RV |
|---|---|---|---|---|---|
| Concentrations rhGARP-TGFβ | 10 μg/ml<br>1 μg/ml<br>0.1 μg/ml | 10 μg/ml<br>1 μg/ml<br>0.1 μg/ml | 10 μg/ml<br>1 μg/ml<br>0.1 μg/ml | 10 μg/ml<br>1 μg/ml<br>0.1 μg/ml | 10 μg/ml<br>1 μg/ml<br>0.1 μg/ml |
| Vol. Phage | 10 μl | 1 μl | 1 μl | 1 μl | 1 μl |
| Time of washing | 0 h | 2 h | O/N | O/3N | O/6N |
| Conditions | — | 37° C., 100 μg/ml rhGARP-TGFβ in 1% casein | 37° C., 100 μg/ml rhGARP-TGFβ in 1% casein | 37° C., 100 μg/ml rhGARP-TGFβ in 1% casein | 37° C., 100 μg/ml rhGARP-TGFβ in 1% casein |

Screenings of at least 24 clones from selection rounds III, IV and V were performed. The clones were grown in deep well plates (1 ml expressions) and periplasmic fractions were prepared. These periplasmic extracts were analyzed on Biacore for improved off-rates. Top four Fab clones with improved off-rates were cloned into hIgG1 (LHG-10 series) and also an effector-dead variant hIgG1 with an N297Q substitution in the Fc region (LHG-10-D series), and the resultant IgGs were analyzed for improved binding characteristics on Biacore (Table 4). In addition, the LHG-10-D IgGs were checked for cross-reactivity on cyno GARP/cyno TGF-β1 in a FACS-based assay using HEK-293E cells transfected with cyno GARP/cyno TGFβ1 or human GARP/human TGFβ1. MHGARP8 was also tested in this cross-reactivity assay. All LHG-10-D and MHG-8 are cross-reactive against cyno GARP/cyno TGFβ1 (FIG. 9).

TABLE 4

Binding characteristics of shuffled clones

|  |  | association | | dissociation | | affinity | |
|---|---|---|---|---|---|---|---|
|  |  | ka (1/Ms) | fold improvement | kd (1/s) | Fold improvement | KD | fold improvement |
| mIgG1 | MHGARP8 | 1.25E+05 | N/A | 3.39E−05 | N/A | 2.64E−10 | N/A |
| hIgG1 - N297Q | LHG-10-D | 1.42E+05 | 1.0 | 2.62E−05 | 1.0 | 1.85E−10 | 1.0 |
|  | LHG-10.3-D | 2.31E+05 | 0.6 | 5.18E−06 | 5.1 | 2.24E−11 | 8.3 |
|  | LHG-10.4-D | 3.71E+05 | 0.4 | 1.21E−05 | 2.2 | 3.27E−11 | 5.7 |
|  | LHG-10.5-D | 3.83E+05 | 0.4 | 1.07E−05 | 2.4 | 2.80E−11 | 6.6 |
|  | LHG-10.6-D | 2.84E+05 | 0.5 | 6.15E−06 | 4.3 | 2.16E−11 | 8.6 |
| hIgG1 | LHG-10 | 2.39E+05 | 1.0 | 3.12E−05 | 1.0 | 1.31E−10 | 1.0 |
|  | LHG-10.3 | 2.87E+05 | 0.8 | 6.38E−06 | 4.9 | 2.22E−11 | 5.9 |
|  | LHG-10.4 | 4.48E+05 | 0.5 | 1.30E−05 | 2.4 | 2.91E−11 | 4.5 |
|  | LHG-10.5 | 4.15E+05 | 0.6 | 1.37E−05 | 2.3 | 3.31E−11 | 4.0 |
|  | LHG-10.6 | 2.76E+05 | 0.9 | 4.40E−06 | 7.1 | 1.59E−11 | 8.2 |

Example 6: Two Anti-hGARP mAbs (MHGARP8 and LHG-10) Inhibit Active TGF-β1 Production by Human Tregs Stimulated human Tregs produce active TGF-β1 close to their cell surface. Autocrine and paracrine TGF-β1 activity induces SMAD2 phosphorylation in Tregs themselves, and in Th cells co-cultured with Tregs (Stockis, J. et al. Eur. J. Immunol. 2009, 39:869-882). To test if GARP is required for TGF-β1 activation by Tregs, we stimulated human Tregs in the presence or absence of anti-hGARP mAbs, and measured phosphorylation of SMAD2 by Western Blot. As a source of human Tregs we used CD4$^+$CD25$^{hi}$CD127$^{lo}$ cells sorted from PBMCs and amplified in vitro during 12-14 days (Gauthy E et al PLoS One. 2013 Sep. 30; 8(9):e76186). As determined by methyl-specific qPCR, amplified cell populations contain 44 to 82% cells with a demethylated FOXP3i1 allele, indicating that they are still highly enriched in Tregs.

Figure 11A:
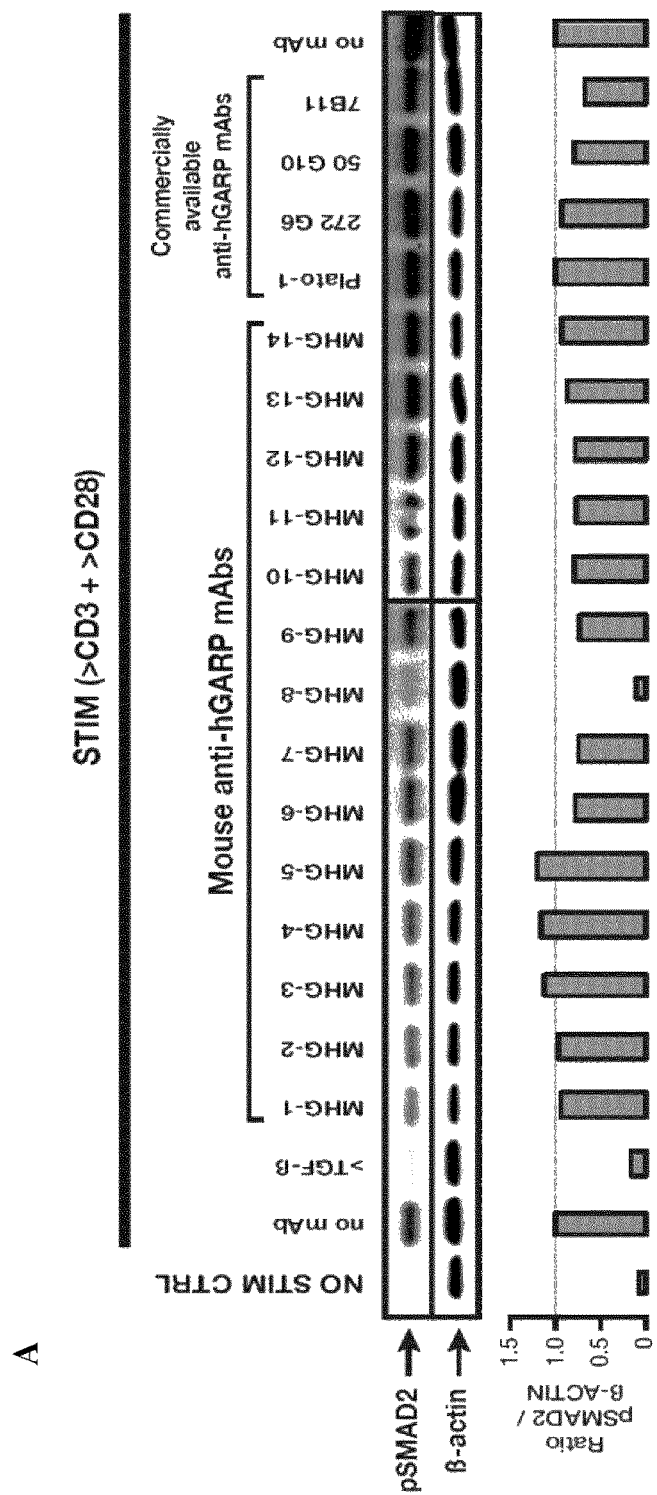
Figure 11B:
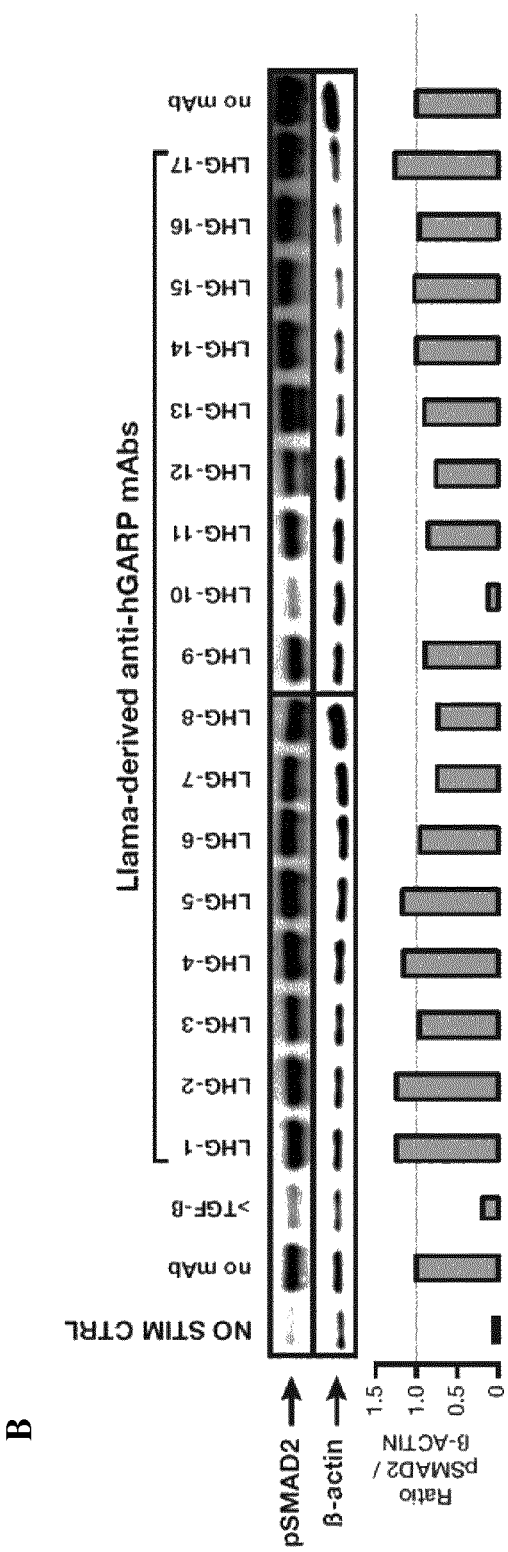

As expected, phosphorylated SMAD2 was detected in the stimulated Tregs, but not in non-stimulated Tregs, nor in Tregs stimulated in the presence of a neutralizing anti-TGF-β1 antibody (FIG. 11). Phosphorylated SMAD2 was greatly reduced in Tregs stimulated in the presence of MHGARP8 (named MHG-8 on FIG. 11A) or LHG-10 (FIG. 11B), indicating that these two anti-hGARP mAbs block active TGF-β production. The 29 other new anti-hGARP mAbs, as well as 4 commercially available anti-hGARP mAbs, did not block TGF-β production by Tregs (FIG. 11).

The inhibitory activity of MHGARP8 and LHG-10 shows that GARP is required for active TGF-β1 production by human Tregs.

Example 7: MHGARP8 and LHG-10 Inhibit the Suppressive Activity of Human Tregs In Vitro We previously showed that human Tregs suppress other T cells at least in part through production of active TGF-β1 (Stockis, J. et al. Eur. J. Immunol. 2009, 39:869-882). We therefore tested whether MHGARP8 (MHG-8) and LHG-10 also inhibit human Treg function in in vitro suppression assays. We used a Treg clone as a source of Tregs, and freshly isolated CD4$^+$CD25$^-$CD127$^{hi}$ cells or a CD4$^+$ T cell clone (Th cells) as targets for suppression. Tregs and Th cells were stimulated with >CD3 and >CD28 in the presence or absence of various additional mAbs. As shown in FIG. 12, clone Treg A1 inhibited the proliferation of CD4$^+$CD25$^-$CD127$^{hi}$ Th cells by 66% in the absence of anti-hGARP mAb. Suppression was reduced to 36% and 32% in the presence of MHG-8 or LHG-10, respectively, but was not reduced in the presence of 6 other anti-hGARP mAbs. We also measured suppression by clone Treg A1 on another Th target (clone Th A2) in the presence of MHGARP8, an anti-hTGF-β1 mAb or an isotype control. MHGARP8 (MHG-8) inhibited the in vitro suppressive activity of Treg A1 in a manner similar to that of the anti-TGF-β1 antibody, whereas the isotype control showed no effect (FIG. 12).

Example 8: Epitopes Recognized by Inhibitory Anti-hGARP mAbs

Only a minority (2/35) of anti-hGARP mAbs block active TGF-β production and suppression by Tregs. This could be due to their ability to bind epitope(s) that are distinct from those bound by non-inhibitory mAbs. We therefore mapped the regions required for binding by inhibitory and non-inhibitory mAbs.

Figure 14A:
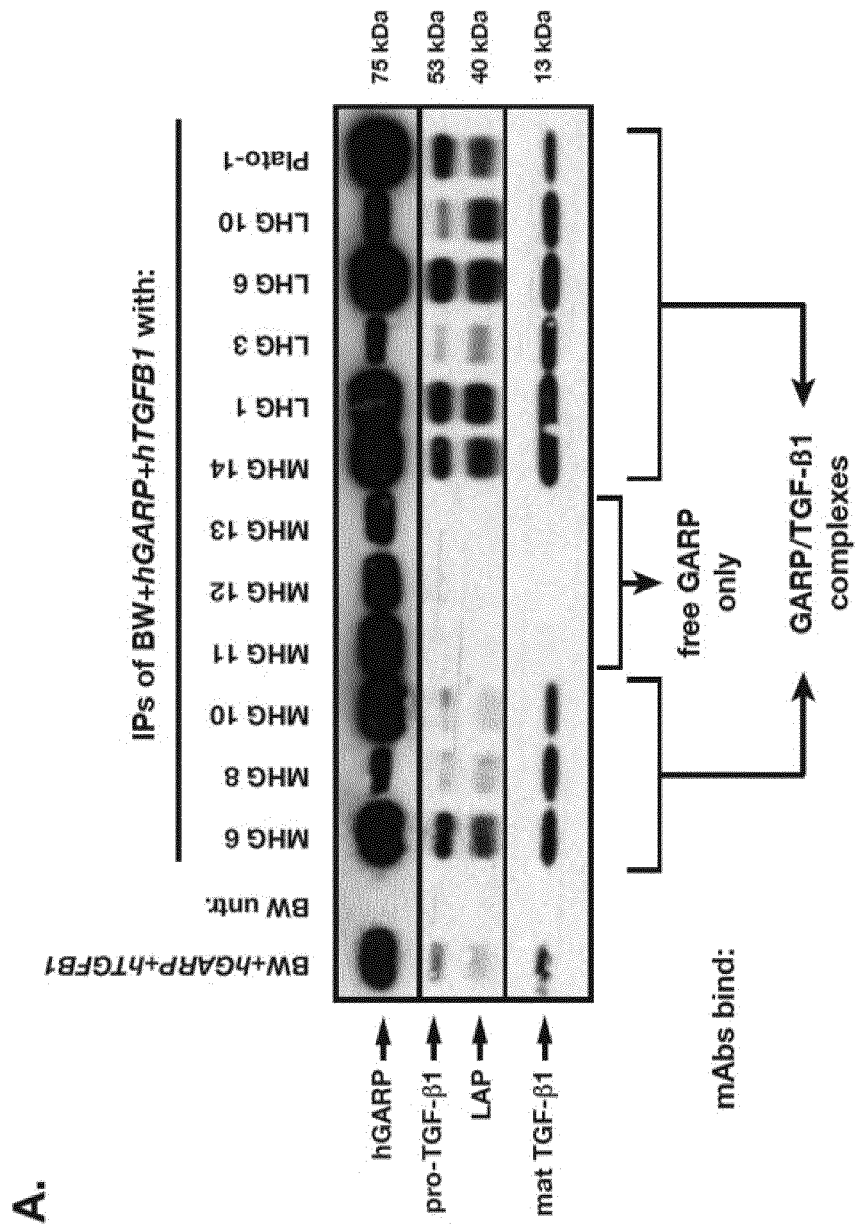

GARP associates with pro- or latent TGF-β1 to form disulfide-linked GARP/TGF-β1 complexes (FIG. 13 and Stockis 2009b Eur. J. Immunol. 2009. 39: 3315-3322 and Gauthy E et al). We first sought to determine whether anti-hGARP mAbs also bind GARP/TGF-β1 complexes, using co-immunoprecipitation (IP) experiments in murine BW cells transfected with hGARP and hTGFB1. We tested 32 anti-hGARP mAbs: our 31 new mAbs and the commercially available Plato-1 mAb. All mAbs efficiently immunoprecipitated GARP (top panel of FIG. 14A, showing IPs with 12 representative mAbs). Pro-TGF-β1, as well as LAP and mature TGF-β1 (i.e. latent TGF-β1) were co-immunoprecipitated with 24 mAbs indicating that they bind GARP/TGF-β1 complexes (6 mAbs shown in FIG. 14A, middle and lower panels). In contrast, 8 mAbs (3 shown in FIG. 14A) did not co-immunoprecipitate pro- or latent TGF-β1, suggesting they bind free GARP but not GARP/TGF-β1 complexes.

Figure 14B:
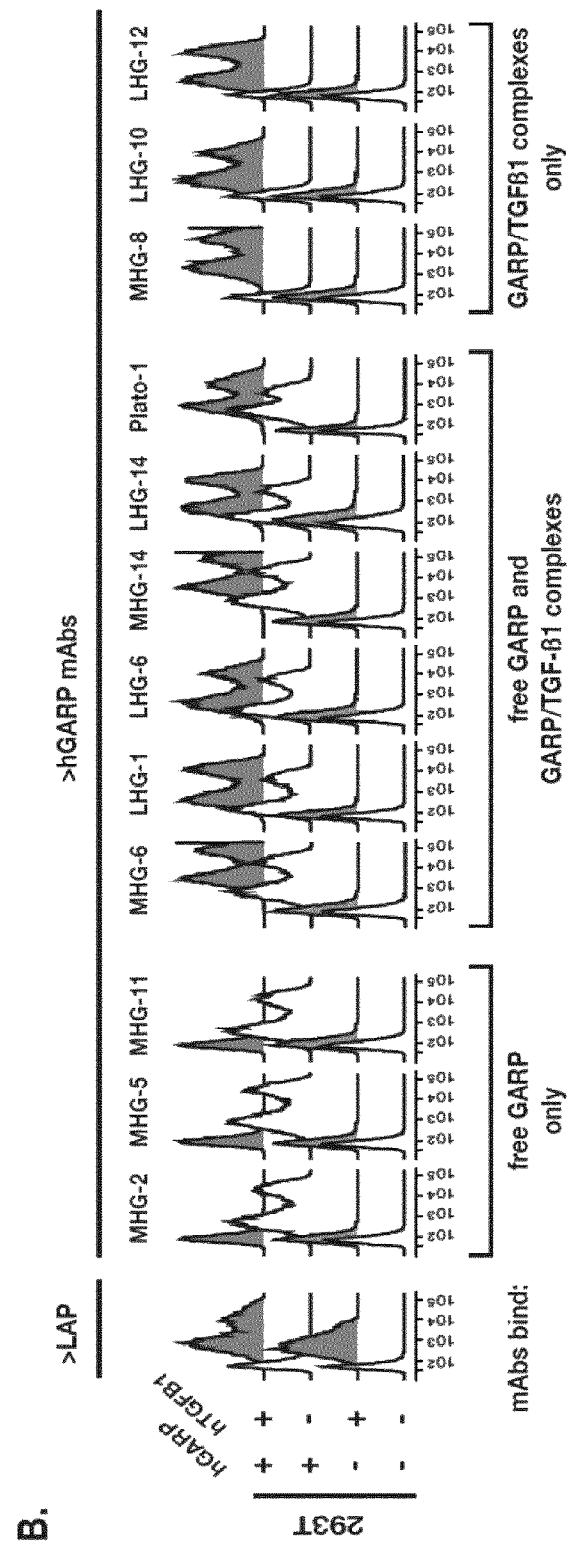

We confirmed this by FACS analyses of transfected 293T cells (FIG. 14B). Untransfected 293T cells express no GARP and very low levels of endogenous TGF-β1. No latent TGF-β is detected on their surface with an anti-LAP antibody. Transfection of GARP or TGFB1 alone induces no or low surface LAP, respectively, whereas co-transfection of GARP and TGFB1 induces high surface LAP as a result of latent TGF-β1 binding and presentation by GARP (FIG. 14B, left histograms). Three groups of anti-hGARP mAbs emerged from the analysis of transfected 293T cells, and are classified in 3 columns in FIG. 13B. A first group (left column) comprises the 8 mAbs that did not co-immunoprecipitate pro- or latent TGF-β1: they bound 293T cells transfected with hGARP alone, but not with hGARP and hTGFB1. This confirms that these mAbs bind free GARP only, as binding to surface GARP is lost in the presence of TGF-β1 (FIG. 14B shows 3 representative mAbs of this group). A second group comprises most other mAbs (19 mAbs, middle column of FIG. 13B): they bound 293T cells equally well upon transfection with hGARP alone or with hGARP and hTGFB1, indicating that they bind both free GARP and GARP/TGF-β1 complexes (FIG. 14B shows 6 mAbs of this group). Interestingly, a third group of 5 mAbs bound 293T cells transfected with hGARP and hTGFB1, but not cells transfected with hGARP alone (right column of FIG. 13B). These mAbs bind GARP/TGF-β1 complexes but not free GARP, and include inhibitory MHGARP8 (MHG-8) and LHG-10 (FIG. 14B shows 3 mAbs of this group).

From the above, we concluded that most mAbs bind free GARP only (8/32) or free GARP and GARP/TF-β1 complexes (19/32). Only 5 mAbs, including inhibitory MHGARP8 (MHG-8) and LHG-10 but also 3 non-inhibitory mAbs, bind GARP/TGF-β1 complexes, but not free GARP. This pattern of recognition does not explain why only MHGARP8 and LHG-10 are inhibitory.

We next sought to define the regions of hGARP required for binding by the various mAbs. The vast majority of the anti-hGARP mAbs do not cross-react on mouse GARP (mGARP). We thus constructed plasmids encoding HA-tagged mGARP/hGARP chimeras (FIG. 15A, left panel) and transfected them in 293T cells, with or without hTFGB1 depending on the binding requirements determined above. All chimeras were expressed at similar levels on the surface of 293T cells, as evidenced by staining with an anti-HA mAb (FIG. 15A, histograms on the right). Binding patterns to mGARP/hGARP chimeras (FIG. 15A, 10 representative mAbs) allowed to identify the region of hGARP required for binding by each anti-hGARP mAb. This is summarized in FIG. 15B, where mAbs are distributed in rows corresponding to various regions of hGARP: mAbs in the first row require a region comprising amino-acids 20 to 101 (hGARP$_{20-101}$), mAbs in the second row require hGARP$_{101-141}$, those in the third require hGARP$_{141-207}$, the fourth, hGARP$_{265-332}$, and finally, a fifth group requires hGARP$_{332-628}$. However, even when considering the regions required for binding, the epitope recognized by inhibitory MHGARP8 (named MHG-8 on the figure) and LHG-10 could not be distinguished from that of non-inhibitory mAbs: MHGARP8 and LHG-10, like LHG-3, -12 and -13, bind GARP/TGF-β complexes that contain hGARP$_{101-141}$.

Sequences of mouse and human GARP$_{101-141}$ differ at 14 amino-acid (aa) positions, comprising 3 clusters of 3 contiguous positions (FIG. 15B, left panel). We constructed 3 mutated versions of hGARP. In each mutant, a series of 3 contiguous aa from region 101-141 were replaced by the aa found in mGARP. We transfected 293T cells with the HA-tagged mutants, alone or with hTGFB1 depending on the binding requirement of the mAbs tested. Binding patterns to mutants revealed 3 types of mAbs (FIG. 15B, right panel), which required amino-acids hGARP$_{111-113}$, hGARP$_{126-127}$, or hGARP$_{137-139}$ for binding, respectively. Six mAbs, including MHGARP8 (named MHG-8 on the figure) and LHG-10, required hGARP$_{137-139}$ (FIG. 13B). Whereas 4 of 6 can bind free hGARP, MHG-8 and LHG-10 are the only mAbs that require hGARP$_{137-139}$ in the context of GARP/TGF-β1 complexes.

From the above, we concluded that inhibition of TGF-β production by MHGARP8 and LHG-10 is associated with the ability to bind an epitope that is distinct from those recognized by all other, non-inhibitory, anti-hGARP mAbs.

Example 9: Inhibition of Human Tregs Function by Anti-hGARP In Vivo

We next sought to evaluate whether inhibitory anti-hGARP mAbs could inhibit human Treg function in vivo. We used a model of xenogeneic graft-versus-host disease (GVHD) induced by transfer of human peripheral blood mononuclear cells (PBMCs) into immuno-compromised NOD/Scid/IL2Rg$^{-/-}$ (NSG) mice. NSG mice have defective cytokine signaling and lack functional T, B and NK cells, allowing very efficient engraftment of human T cells upon i.v. injection of PBMCs. Thirty to forty days after PBMC transfer, recipient mice develop xenogeneic GVHD, due to the activity of human cytotoxic T lymphocytes against murine tissues Shultz, Nat Rev Immunol. 2012 November; 12(11):786-98. In this model, co-transfer of human Tregs with human PBMCs attenuates GVHD (Hannon et al. Transfusion. 2014 February; 54(2):353-63), providing a model to test the inhibitory activity of anti-hGARP mAbs on human Tregs in vivo.

Figure 16C:
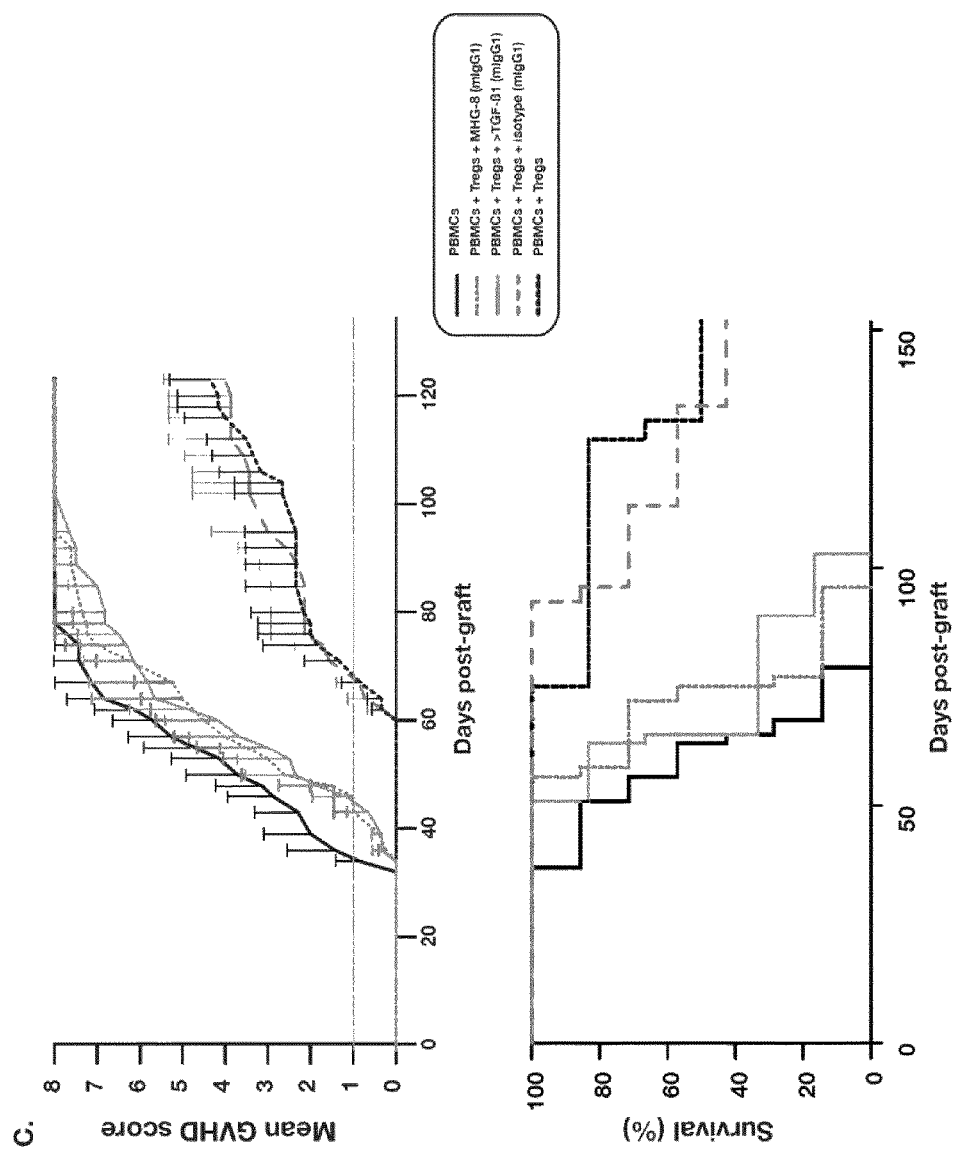

We transferred human PBMCs (3×10$^6$/mouse) with or without autologous Tregs (1.5×10$^6$/mouse) in NSG mice (FIG. 16A). As a source of human Tregs, we used blood CD4$^+$CD25$^{hi}$CD127$^{lo}$ cells that had been shortly amplified in vitro, as described above. In addition, mice were injected with MHGARP8 (named MHG-8 on the figure), anti-TGF-β1, an isotype control or PBS, one day before the graft and weekly thereafter. Objective signs of GVHD were monitored bi-weekly, to establish a disease score based on weight loss, reduced mobility, anemia or icterus, and hair loss. We performed four independent experiments (FIG. 16B), and detailed results are shown for one (FIG. 16C). Depending on the experiment, onset of disease (mean GVHD score ≥1) was observed 28 to 41 days after PBMC transfer in groups of mice that received no mAb or an isotype control. Co-transfer of Tregs delayed disease, which occurred 46 to 72 days after transfer, indicating that human Tregs were able to suppress human T cell responses against xenogeneic antigens. Administration of MHGARP8 to mice transferred with PBMCs and Tregs abrogated the protective effect of Tregs: disease occurred as early as in mice receiving PBMCs only (28 to 44 days after transfer). Inhibition of Treg suppressive function by MHGARP8 was similar to that observed with a neutralizing anti-TGF-β1 antibody. An isotype control had no effect.

Altogether, this shows that MHGARP8 inhibits the immune-suppressive function of human Tregs in vivo.

The invention claimed is:

1. A method for inhibiting the immune suppressive function of human T regulatory cells (Tregs) in a subject with a TGF-β related disorder, comprising administering to a subject in need thereof an effective amount of a monoclonal antibody capable of binding to a conformational epitope of a complex of human Glycoprotein A Repetitions Predominant (hGARP) and TGF-β, said conformational epitope comprising amino acids of hGARP and amino acids of latent TGF-β, wherein the amino acids of hGARP are at least one of amino acids 137 to 139 of hGARP, and wherein the monoclonal antibody inhibits TGF-β activation, thereby inhibiting Treg function in the subject.

2. The method according to claim 1, wherein the TGF-β related disorder is cancer.

3. The method according to claim 1, wherein the monoclonal antibody is administered in combination with a treatment for cancer.

4. The method according to claim 1, wherein the amino acids of hGARP are amino acids 137 to 139 of hGARP.

5. The method according to claim 1, wherein the monoclonal antibody is a whole antibody.

6. The method according to claim 1, wherein the monoclonal antibody is a humanized antibody.

7. The method according to claim 3, wherein antibody is administered in combination with another immunotherapeutic agent.

8. The method of claim 7, wherein the other immunotherapeutic agent is a tumor vaccine.

* * * * *

SEQUENCE LISTING

<160> NUMBER OF SEQ ID NOS: 57

<210> SEQ ID NO 1
<211> LENGTH: 662
<212> TYPE: PRT
<213> ORGANISM: Homo sapiens

<400> SEQUENCE: 1

Met Arg Pro Gln Ile Leu Leu Leu Ala Leu Leu Thr Leu Gly Leu
1               5                   10                  15

Ala Ala Gln His Gln Asp Lys Val Pro Cys Lys Met Val Asp Lys Lys
            20                  25                  30

Val Ser Cys Gln Val Leu Gly Leu Leu Gln Val Pro Ser Val Leu Pro
        35                  40                  45

Pro Asp Thr Glu Thr Leu Asp Leu Ser Gly Asn Gln Leu Arg Ser Ile
    50                  55                  60

Leu Ala Ser Pro Leu Gly Phe Tyr Thr Ala Leu Arg His Leu Asp Leu
65                  70                  75                  80

Ser Thr Asn Glu Ile Ser Phe Leu Gln Pro Gly Ala Phe Gln Ala Leu
                85                  90                  95

-continued

```
Thr His Leu Glu His Leu Ser Leu Ala His Asn Arg Leu Ala Met Ala
            100                 105                 110
Thr Ala Leu Ser Ala Gly Gly Leu Gly Pro Leu Pro Arg Val Thr Ser
        115                 120                 125
Leu Asp Leu Ser Gly Asn Ser Leu Tyr Ser Gly Leu Leu Glu Arg Leu
    130                 135                 140
Leu Gly Glu Ala Pro Ser Leu His Thr Leu Ser Leu Ala Glu Asn Ser
145                 150                 155                 160
Leu Thr Arg Leu Thr Arg His Thr Phe Arg Asp Met Pro Ala Leu Glu
                165                 170                 175
Gln Leu Asp Leu His Ser Asn Val Leu Met Asp Ile Glu Asp Gly Ala
            180                 185                 190
Phe Glu Gly Leu Pro Arg Leu Thr His Leu Asn Leu Ser Arg Asn Ser
        195                 200                 205
Leu Thr Cys Ile Ser Asp Phe Ser Leu Gln Gln Leu Arg Val Leu Asp
    210                 215                 220
Leu Ser Cys Asn Ser Ile Glu Ala Phe Gln Thr Ala Ser Gln Pro Gln
225                 230                 235                 240
Ala Glu Phe Gln Leu Thr Trp Leu Asp Leu Arg Glu Asn Lys Leu Leu
                245                 250                 255
His Phe Pro Asp Leu Ala Ala Leu Pro Arg Leu Ile Tyr Leu Asn Leu
            260                 265                 270
Ser Asn Asn Leu Ile Arg Leu Pro Thr Gly Pro Pro Gln Asp Ser Lys
        275                 280                 285
Gly Ile His Ala Pro Ser Glu Gly Trp Ser Ala Leu Pro Leu Ser Ala
    290                 295                 300
Pro Ser Gly Asn Ala Ser Gly Arg Pro Leu Ser Gln Leu Leu Asn Leu
305                 310                 315                 320
Asp Leu Ser Tyr Asn Glu Ile Glu Leu Ile Pro Asp Ser Phe Leu Glu
                325                 330                 335
His Leu Thr Ser Leu Cys Phe Leu Asn Leu Ser Arg Asn Cys Leu Arg
            340                 345                 350
Thr Phe Glu Ala Arg Arg Leu Gly Ser Leu Pro Cys Leu Met Leu Leu
        355                 360                 365
Asp Leu Ser His Asn Ala Leu Glu Thr Leu Glu Leu Gly Ala Arg Ala
    370                 375                 380
Leu Gly Ser Leu Arg Thr Leu Leu Leu Gln Gly Asn Ala Leu Arg Asp
385                 390                 395                 400
Leu Pro Pro Tyr Thr Phe Ala Asn Leu Ala Ser Leu Gln Arg Leu Asn
                405                 410                 415
Leu Gln Gly Asn Arg Val Ser Pro Cys Gly Gly Pro Asp Glu Pro Gly
            420                 425                 430
Pro Ser Gly Cys Val Ala Phe Ser Gly Ile Thr Ser Leu Arg Ser Leu
        435                 440                 445
Ser Leu Val Asp Asn Glu Ile Glu Leu Leu Arg Ala Gly Ala Phe Leu
    450                 455                 460
His Thr Pro Leu Thr Glu Leu Asp Leu Ser Ser Asn Pro Gly Leu Glu
465                 470                 475                 480
Val Ala Thr Gly Ala Leu Gly Gly Leu Glu Ala Ser Leu Glu Val Leu
                485                 490                 495
Ala Leu Gln Gly Asn Gly Leu Met Val Leu Gln Val Asp Leu Pro Cys
            500                 505                 510
Phe Ile Cys Leu Lys Arg Leu Asn Leu Ala Glu Asn Arg Leu Ser His
```

```
            515                 520                 525
Leu Pro Ala Trp Thr Gln Ala Val Ser Leu Glu Val Leu Asp Leu Arg
    530                 535                 540
Asn Asn Ser Phe Ser Leu Leu Pro Gly Ser Ala Met Gly Gly Leu Glu
545                 550                 555                 560
Thr Ser Leu Arg Arg Leu Tyr Leu Gln Gly Asn Pro Leu Ser Cys Cys
                565                 570                 575
Gly Asn Gly Trp Leu Ala Ala Gln Leu His Gln Gly Arg Val Asp Val
                580                 585                 590
Asp Ala Thr Gln Asp Leu Ile Cys Arg Phe Ser Ser Gln Glu Glu Val
                595                 600                 605
Ser Leu Ser His Val Arg Pro Glu Asp Cys Glu Lys Gly Gly Leu Lys
    610                 615                 620
Asn Ile Asn Leu Ile Ile Ile Leu Thr Phe Ile Leu Val Ser Ala Ile
625                 630                 635                 640
Leu Leu Thr Thr Leu Ala Ala Cys Cys Cys Val Arg Arg Gln Lys Phe
                645                 650                 655
Asn Gln Gln Tyr Lys Ala
                660
```

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      VH-CDR1 peptide

<400> SEQUENCE: 2

```
Gly Phe Ser Leu Thr Gly Tyr Gly Ile Asn
1               5                   10
```

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      VH-CDR2 peptide

<400> SEQUENCE: 3

```
Met Ile Trp Ser Asp Gly Ser Thr Asp Tyr Asn Ser Val Leu Thr Ser
1               5                   10                  15
```

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      VH-CDR3 peptide

<400> SEQUENCE: 4

```
Asp Arg Asn Tyr Tyr Asp Tyr Asp Gly Ala Met Asp Tyr
1               5                   10
```

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 peptide

```
<400> SEQUENCE: 5

Lys Ala Ser Asp His Ile Lys Asn Trp Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 peptide

<400> SEQUENCE: 6

Gly Ala Thr Ser Leu Glu Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 peptide

<400> SEQUENCE: 7

Gln Gln Tyr Trp Ser Thr Pro Trp Thr
1               5

<210> SEQ ID NO 8
<211> LENGTH: 140
<212> TYPE: PRT
<213> ORGANISM: Artificial Sequence
<220> FEATURE:
<223> OTHER INFORMATION: Description of Artificial Sequence: Synthetic
      heavy chain variable region polypeptide

<400> SEQUENCE: 8

Met Ala Val Leu Ala Leu Leu Phe Cys Leu Val Thr Phe Pro Ser Cys
1               5                   10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Ile Asn Trp Val Arg Gln Pro Pro Gly Lys Gly Leu
    50                  55                  60

Glu Trp Leu Gly Met Ile Trp Ser Asp Gly Ser Thr Asp Tyr Asn Ser
65                  70                  75                  80

Val Leu Thr Ser Arg Leu Arg Ile Ser Lys Asp Asn Ser Asn Ser Gln
                85                  90                  95

Val Phe Leu Lys Met Asn Ser Leu Gln Val Asp Asp Thr Ala Arg Tyr
            100                 105                 110

Tyr Cys Ala Arg Asp Arg Asn Tyr Tyr Asp Tyr Asp Gly Ala Met Asp
        115                 120                 125

Tyr Trp Gly Gln Gly Thr Ser Val Thr Val Ser Ser
    130                 135                 140

<210> SEQ ID NO 9
<211> LENGTH: 127
<212> TYPE: PRT
<213> ORGANISM: Artificial Sequence
<220> FEATURE:
<223> OTHER INFORMATION: Description of Artificial Sequence: Synthetic
``` light chain variable region polypeptide

<400> SEQUENCE: 9

Met Lys Phe Pro Ser Gln Leu Leu Phe Leu Leu Phe Arg Ile Thr
1               5                   10                  15

Gly Ile Ile Cys Asp Ile Gln Val Thr Gln Ser Ser Tyr Leu Ser
            20                  25                  30

Val Ser Leu Gly Asp Arg Val Thr Ile Thr Cys Lys Ala Ser Asp His
        35                  40                  45

Ile Lys Asn Trp Leu Ala Trp Tyr Gln Gln Lys Pro Gly Ile Ala Pro
    50                  55                  60

Arg Leu Leu Val Ser Gly Ala Thr Ser Leu Glu Ala Gly Val Pro Ser
65                  70                  75                  80

Arg Phe Ser Gly Ser Gly Ser Gly Lys Asn Phe Thr Leu Ser Ile Thr
                85                  90                  95

Ser Leu Gln Thr Glu Asp Val Ala Thr Tyr Tyr Cys Gln Gln Tyr Trp
            100                 105                 110

Ser Thr Pro Trp Thr Phe Gly Gly Gly Thr Thr Leu Glu Ile Arg
        115                 120                 125

<210> SEQ ID NO 10
<211> LENGTH: 420
<212> TYPE: DNA
<213> ORGANISM: Artificial Sequence
<220> FEATURE:
<223> OTHER INFORMATION: Description of Artificial Sequence: Synthetic
      heavy chain variable region polynucleotide

<400> SEQUENCE: 10
atggctgtcc tggcattact cttctgcctg gtaacattcc caagctgtat cctttcccag      60
gtgcagctga aggagtcagg acctggcctg gtggcgccct cacagagcct gtccatcaca     120
tgcaccgtct cagggttctc attaaccggc tatggtataa actgggttcg ccagcctcca     180
ggaaagggtc tggagtggct gggaatgata tggagtgatg aagcacaga ctataattca      240 gttctcacat ccagactgag gatcagtaag gataattcca atagccaggt tttcttaaaa     300
atgaacagtc tgcaagttga tgacacagcc aggtactatt gtgccagaga tcgaaactac     360
tatgattacg acggggctat ggactactgg ggtcaaggaa cctcagtcac cgtctcctca     420

<210> SEQ ID NO 11
<211> LENGTH: 381
<212> TYPE: DNA
<213> ORGANISM: Artificial Sequence
<220> FEATURE:
<223> OTHER INFORMATION: Description of Artificial Sequence: Synthetic
      light chain variable region polynucleotide

<400> SEQUENCE: 11
atgaagtttc cttctcaact tctgctcttc ctgctgttca gaatcacagg cataatatgt      60
gacatccagg tgacacaatc ttcatcctac ttgtctgtat ctctaggaga cagggtcacc     120
attacttgca aggcaagtga ccacattaaa aattggttag cctggtatca gcagaaacca     180
ggaattgctc ctaggctctt agtttctggt gcaaccagtt tggaagctgg ggttccttca     240
agattcagtg gcagtggatc tggaaagaat ttcactctca gcattaccag tcttcagact     300
gaagatgttg ctacttatta ctgtcaacag tattggagta caccgtggac gttcggtgga     360
ggcaccactc tggagatcag a                                               381

```
<210> SEQ ID NO 12
<211> LENGTH: 41
<212> TYPE: PRT
<213> ORGANISM: Artificial Sequence
<220> FEATURE:
<223> OTHER INFORMATION: Description of Artificial Sequence: Synthetic
      conformational epitope polypeptide

<400> SEQUENCE: 12

His Leu Ser Leu Ala His Asn Arg Leu Ala Met Ala Thr Ala Leu Ser
1               5                   10                  15

Ala Gly Gly Leu Gly Pro Leu Pro Arg Val Thr Ser Leu Asp Leu Ser
            20                  25                  30

Gly Asn Ser Leu Tyr Ser Gly Leu Leu
        35                  40

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      VH-CDR1 LHG-10 peptide

<400> SEQUENCE: 13

Ser Tyr Tyr Ile Asp
1               5

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      VH-CDR2 LHG-10 peptide

<400> SEQUENCE: 14

Arg Ile Asp Pro Glu Asp Gly Gly Thr Lys Tyr Ala Gln Lys Phe Gln
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      VH-CDR3 LHG-10 peptide

<400> SEQUENCE: 15

Asn Glu Trp Glu Thr Val Val Val Gly Asp Leu Met Tyr Glu Tyr Glu
1               5                   10                  15

Tyr

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 LHG-10 peptide
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
```

```
-continued

<222> LOCATION: (7)..(7)
<223> OTHER INFORMATION: Ser or Val
<220> FEATURE:
<221> NAME/KEY: MOD_RES
<222> LOCATION: (9)..(9)
<223> OTHER INFORMATION: Tyr or Phe

<400> SEQUENCE: 16

Gln Ala Ser Gln Xaa Ile Xaa Ser Xaa Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG-10 peptide
<220> FEATURE:
<221> NAME/KEY: MOD_RES
<222> LOCATION: (1)..(1)
<223> OTHER INFORMATION: Gly or Arg
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (4)..(4)
<223> OTHER INFORMATION: Arg or Ile
<220> FEATURE:
<221> NAME/KEY: MOD_RES
<222> LOCATION: (5)..(5)
<223> OTHER INFORMATION: Leu or Pro
<220> FEATURE:
<221> NAME/KEY: MOD_RES
<222> LOCATION: (6)..(6)
<223> OTHER INFORMATION: Gln or Lys

<400> SEQUENCE: 17

Xaa Xaa Ser Xaa Xaa Xaa Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG-10 peptide
<220> FEATURE:
<221> NAME/KEY: MOD_RES
<222> LOCATION: (4)..(4)
<223> OTHER INFORMATION: Asp, Ala, Tyr or Val
<220> FEATURE:
<221> NAME/KEY: MOD_RES
<222> LOCATION: (6)..(6)
<223> OTHER INFORMATION: Ala, Leu or Val
<220> FEATURE:
<221> NAME/KEY: MOD_RES
<222> LOCATION: (8)..(8)
<223> OTHER INFORMATION: Val or Pro

<400> SEQUENCE: 18

Gln Gln Tyr Xaa Ser Xaa Pro Xaa Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
```

VL-CDR1 LHG-10 peptide

<400> SEQUENCE: 19

Gln Ala Ser Gln Ser Ile Ser Ser Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG10 peptide

<400> SEQUENCE: 20

Gly Ala Ser Arg Leu Gln Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG10 peptide

<400> SEQUENCE: 21

Gln Gln Tyr Asp Ser Leu Pro Val Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 LHG10.3 peptide

<400> SEQUENCE: 22

Gln Ala Ser Gln Ser Ile Val Ser Tyr Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG10.3 peptide

<400> SEQUENCE: 23

Gly Ala Ser Arg Leu Gln Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG10.3 peptide

<400> SEQUENCE: 24

Gln Gln Tyr Ala Ser Ala Pro Val Thr
1               5

<210> SEQ ID NO 25

```
<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 LHG10.4 peptide

<400> SEQUENCE: 25

Gln Ala Ser Gln Ser Ile Ser Ser Tyr Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG10.4 peptide

<400> SEQUENCE: 26

Gly Thr Ser Arg Leu Lys Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG10.4 peptide

<400> SEQUENCE: 27

Gln Gln Tyr Tyr Ser Ala Pro Val Thr
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 LHG10.5 peptide

<400> SEQUENCE: 28

Gln Ala Ser Gln Thr Ile Ser Ser Phe Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG10.5 peptide

<400> SEQUENCE: 29

Arg Ala Ser Ile Pro Gln Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG10.5 peptide

<400> SEQUENCE: 30
```

```
Gln Gln Tyr Val Ser Ala Pro Pro Thr
1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      VL-CDR1 LHG10.6 peptide

<400> SEQUENCE: 31

Gln Ala Ser Gln Ser Ile Ser Ser Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      VL-CDR2 LHG10.6 peptide

<400> SEQUENCE: 32

Gly Ala Ser Arg Leu Lys Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      VL-CDR3 LHG10.6 peptide

<400> SEQUENCE: 33

Gln Gln Tyr Ala Ser Val Pro Val Thr
1               5

<210> SEQ ID NO 34
<211> LENGTH: 126
<212> TYPE: PRT
<213> ORGANISM: Artificial Sequence
<220> FEATURE:
<223> OTHER INFORMATION: Description of Artificial Sequence: Synthetic
      heavy chain variable region of sequence of LHG10 polypeptide

<400> SEQUENCE: 34

Glu Val Gln Leu Val Gln Pro Gly Ala Glu Leu Arg Asn Ser Gly Ala
1               5                   10                  15

Ser Val Lys Val Ser Cys Lys Ala Ser Gly Tyr Arg Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Asn Glu Trp Glu Thr Val Val Gly Asp Leu Met Tyr Glu
            100                 105                 110

Tyr Glu Tyr Trp Gly Gln Gly Thr Gln Val Thr Val Ser Ser
        115                 120                 125
```

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain variable region of sequence LHG10 polypeptide

<400> SEQUENCE: 35

Asp Ile Gln Met Thr Gln Ser Pro Thr Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Asp Ser Leu Pro Val
                85                  90                  95

Thr Phe Gly Gln Gly Thr Lys Val Glu Leu Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain variable region of sequence of LHG10.3
      polypeptide

<400> SEQUENCE: 36

Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Val Ser Tyr
            20                  25                  30

Leu Ala Trp Tyr Gln Gln Lys Pro Gly Gln Ala Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Ala Ser Ala Pro Val
                85                  90                  95

Thr Phe Gly Gln Gly Thr Gly Val Glu Leu Lys
            100                 105

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain variable region of sequence of LHG10.4
      polypeptide

<400> SEQUENCE: 37

Asp Ile Gln Met Thr Gln Ser Pro Ser Ser Leu Ser Ala Ser Leu Gly

```
                1               5                   10                  15
Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Ala Pro Lys Leu Leu Ile
            35                  40                  45

Tyr Gly Thr Ser Arg Leu Lys Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Tyr Ser Ala Pro Val
                85                  90                  95

Thr Phe Gly Gln Gly Thr Lys Val Glu Leu Lys
                100                 105
```

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain variable region of sequence of LHG10.5
      polypeptide

<400> SEQUENCE: 38

```
Asp Ile Gln Met Thr Gln Ser Pro Ser Ser Leu Ser Pro Ser Leu Gly
1               5                   10                  15

Asp Arg Val Thr Ile Thr Cys Gln Ala Ser Gln Thr Ile Ser Ser Phe
                20                  25                  30

Leu Ala Trp Tyr His Gln Lys Pro Gly Gln Pro Pro Lys Leu Leu Ile
            35                  40                  45

Tyr Arg Ala Ser Ile Pro Gln Thr Gly Val Pro Ser Arg Phe Ser Gly
    50                  55                  60

Ser Gly Ser Gly Thr Ser Phe Thr Leu Thr Ile Gly Gly Leu Glu Ala
65                  70                  75                  80

Glu Asp Ala Gly Thr Tyr Tyr Cys Gln Gln Tyr Val Ser Ala Pro Pro
                85                  90                  95

Thr Phe Gly Gln Gly Thr Lys Val Glu Leu Lys
                100                 105
```

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain variable region of sequence of LHG10.6
      polypeptide

<400> SEQUENCE: 39

```
Asp Ile Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Ala Pro Asn Ile Leu Ile
            35                  40                  45

Tyr Gly Ala Ser Arg Leu Lys Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80
```

Glu Asp Ala Gly Thr Tyr Tyr Cys Gln Gln Tyr Ala Ser Val Pro Val
                85                  90                  95

Thr Phe Gly Gln Gly Thr Lys Val Glu Leu Lys
            100                 105

<210> SEQ ID NO 40
<211> LENGTH: 45
<212> TYPE: PRT
<213> ORGANISM: Artificial Sequence
<220> FEATURE:
<223> OTHER INFORMATION: Description of Artificial Sequence: Synthetic
      human GARP truncated and tagged polypeptide

<400> SEQUENCE: 40

Glu Ala Ala Glu Asn Leu Tyr Phe Gln Gly Ala Ala Trp Ser His Pro
1               5                   10                  15

Gln Phe Glu Lys Gly Ala Ala Trp Ser His Pro Gln Phe Glu Lys Gly
            20                  25                  30

Ala Ala Trp Ser His Pro Gln Phe Glu Lys Gly Ala Ala
            35                  40                  45

<210> SEQ ID NO 41
<211> LENGTH: 4216
<212> TYPE: DNA
<213> ORGANISM: Macaca fascicularis
<220> FEATURE:
<223> OTHER INFORMATION: predicted cynomolgus GARP

<400> SEQUENCE: 41

| | | | | | |
|---|---|---|---|---|---|
| ggtggggcag | ctgagtggcc | tgcgcctcct | cgggccgtga | ccccggggtc | tggcgcgggg | 60 |
| tgggacccgg | gggcgggttt | gcgcaaaatg | tgccgagact | gccgggagag | gaactgcgg | 120 |
| ccgcgctgag | ccagagccat | gagcccccag | atcctgctgc | tcctggccct | gctgaccta | 180 |
| ggcctggctg | cacaacacca | agacaaagtg | gcatgtaaga | tggtggacaa | gaaggtctcg | 240 |
| tgccagggtc | tgggcctgct | ccaggtcccc | ttggtgctcc | cgccggacac | tgagaccctt | 300 |
| gatctctctg | gaaccagct | gcggagtatc | ctggcctcac | ccctgggctt | ctacacggca | 360 |
| cttcgtcacc | tggacctgag | caccaatgag | atcaacttcc | tccagccagg | agccttccag | 420 |
| gccctgaccc | acctggagca | cctcagcctg | gctcacaacc | ggctggcgat | ggccactgcg | 480 |
| ctgagtgccg | tggtctgggc | cccctgcca | cgtgtgacct | ccctggacct | gtctgggaac | 540 |
| agcctgtaca | gcggcctgct | ggagcggctg | ctaggggagg | cacccagcct | gcatacccc | 600 |
| tcactggcg | agaacagtct | gactcgcctc | acccgccaca | ccttccggga | catgcctgcg | 660 |
| ctggagcagc | ttgacctgca | tagcaacgtg | ctgatggaca | tcgaggatgg | cgccttcgag | 720 |
| ggcctgcccc | acctgacccca | tctcaacctt | tccaggaatt | cctcacctg | catctccgac | 780 |
| ttcagccttc | agcagctgcg | ggtgctggac | ctgagctgca | acagcattga | ggcctttcag | 840 |
| acggcctccc | agcccaggc | cgagttccag | ctcacctggc | ttgacctgcg | ggagaacaaa | 900 |
| ctgctccatt | tccccgacct | ggccgcgctc | ccgagactca | tctacctgaa | cttgtccaac | 960 |
| aacctcatcc | ggctcccac | agggccaccc | caggacagca | agggcatcca | cgcgccttcc | 1020 |
| gagggctggt | cagccctgcc | cctctcaacc | cccaatggga | atgtcagtgc | ccgccccctt | 1080 |
| tcccagctct | tgaatctgga | tttgagctac | aatgagattg | aactcatccc | gacagctttt | 1140 |
| cttgagcacc | tgacctccct | gtgcttcctg | aacctcagca | gaactgctt | gcggaccttt | 1200 |
| gaggcccggc | gctcaggctc | cctgcccctgc | ctgatgctcc | ttgatttaag | ccacaatgcc | 1260 |

-continued

```
ctggagacac tggaactggg cgccagagcc ctggggtcct tgcggacact gctcctacag    1320
ggcaatgccc tgcgggacct gcctccatac acctttgcca acctggccag cctgcagcgg    1380
ctcaacctgc aggggaaccg ggtcagcccc tgtgggggc  cgaatgagcc cggccccgcc    1440
agctgtgtgg ccttctctgg catcgcctcc ctccgcagcc tgagcctggt ggataatgag    1500
atagagctgc tcagggcagg ggccttcctc catacccac  tgactgagct ggacctttct    1560
tccaaccctg ggctggaggt ggccacaggg gccttgacag gcctggaggc ctccttggaa    1620
gtcctggcac tgcagggcaa tgggttgacg gtcctgcagg tggacctgcc ctgcttcatc    1680
tgcctcaagc ggctcaatct tgccgagaac cgcctgagcc accttcccgc ctggacacag    1740
gctgtgtcac tggaggtgct ggacctgcga acaacagct  tcagcctcct gccaggcagt    1800
gccatgggtg gcctggagac cagcctccgg cgcctctacc tgcaggggaa tccactcagc    1860
tgctgtggca atggctggct ggcagcccag ctgcaccagg gccgtgtgga cgtggacgcc    1920
acccaggacc tgatctgccg cttcagctcc caggaggagg tgtccctgag ccacgtgcgt    1980
cccgaggact gtgagaaggg ggggctcaag aacatcaacc tcatcatcat cctcaccttc    2040
atactggtct ctgccatcct cctcaccacg ctggccacct gctgctgtgt ccgccggcag    2100
aagtttaacc aacagtataa agcctaaaga agccgggaga cactctaggt caatggggga    2160
gcctgaggta cagagaagag tgaggactga ctcaaggtca cacagtgacc caggatccca    2220
gaactctggt ctccaaattg caacccggga cacctttctc tgccgcctgc tgcatcagcg    2280
ggtgaccccc ttcccgggct gcactttggg tccagctgtg aagccagaa  gttgggcggt    2340
ttcagggaca gcaggaata  atgttgacct atcagatcaa caaatcttca ctgagcatct    2400
actttgtgcc acactctgct ctgggcactg gaatgctgg  gaaataagat acactcccgc    2460
cctcaagaat ctcccagtct ggtaggaggg agtgctacag agccgcgtgg tgaccacgca    2520
gtgtgcttag ggcctgaggt gtgaaagccc gggactccgg agctcggcag gccccgctgg    2580
ttcgatgcga agagtcctgc cccagccatg ccagggtgag agagggccaa gcctgggagg    2640
atttgtctga cacatttcca agcagactgt tgtcacatc  ttctgataat gactttcagt    2700
ctctctgaaa atgaaaagct tatgaccgga agagagaatt ggagccatac gagtgtgtct    2760
tggatctggt gctgttaggc gggccgcggc ggctccagca gggtctggtt aaggggtcca    2820
gcccggcact ggaccattcc gtctcctgct ctggacaggc cgtctccctg cctggcactc    2880
tcatgttaca cagcctgatc ccagtactgc tctaagcgcc gtccctgccc agcccttctc    2940
catcgcagcc ccgccttggc tgctaagcca agagctaaaa ccttagatat ctgattctgt    3000
tttgcaccca gcttggcaga tgtggatgtg aatccaagcc tgtgtctgcc cctatatgac    3060
agcccttgga ggttggtatt ttatccccat tttataaaag aggaaactga agttctacaa    3120
atctccttcc agggccccag ctaactaatg ccttaggtga gattcaaacc ctcatacttc    3180
tgtctccagg gcctgatctt tgccactgca ggggctgcag gccgttaagt ggacaggaag    3240
tggctccaca tagcccgagc agggtctgga agtatcctgt gctatgcata cctgctctct    3300
cctctctccc aggcaggcag ctgcaggcgc tctcctcctc ctctgcctta gtttccctcc    3360
ttccatcctt tccaccctgg tgtgggttct cctgttctct ctgtgctctt gcatgctctc    3420
attcctttt  cctctattga gcagagcctg gagtttgaga ctattgaatc caacctcccc    3480
attgcacaga tggggaaact gaggcttagg aagagaatga aacttgtgga gagctataca    3540
gagcctctgg ggaaaaaaaa gagagcccta tttggggatg agattagggg ttggaccata    3600
gtgatgtcct ctcttggctg tcacatcaca agataatgct ggctccaaac ttccttctg    3660
```

```
tgcctcctca tgcaggattt ttttttccc tcttggaaaa ataggtagaa aggctcaccc    3720
agataacccc ctatccctca tagcatggag tcatgagctg tctgggaaga atggacacgc    3780
tgggaccaac tcaagacctt gtgttgctgt cttcatcatc ttacctgtgc ttggcccaca    3840
gtctggctca tgatgtgggc tcagtaatgt gcaagaaaat gaaatgcca ctctctccac    3900 cccattttac agaggagaac accgaggccc agaggaagtt aagggagagt caatgggcag    3960
agccagggct aggccctggt gatgtgtgga gcacccaggc agacccagtc ctggttggga    4020
tcacaaccac aggtgctact gcacgtgaca ctcttcctta ggcctggagg ccaaggtgtg    4080
ggtcctcacg cctgatcttt gaaaacacta cacaatgctg ctgtcagttc ccaggaccca    4140
ggccgcagcc caggcctcgg gaccaactct ttgtataacc tacctgaatg tattaaaaac    4200
taattttgga gaagca                                                  4216

<210> SEQ ID NO 42
<211> LENGTH: 2188
<212> TYPE: DNA
<213> ORGANISM: Macaca fascicularis
<220> FEATURE:
<223> OTHER INFORMATION: cynomolgus TGF beta-1

<400> SEQUENCE: 42
ccgccgccct tcgcgccctg ggccatctcc ctcccacctc cctccgcgga tcagccagac      60
tgcgagggcc ccggccgggg gcaggggga cgccccgtcc ggggcacccc cccggctctg     120
agccgcccgc ggggccggcc tcggcccgga gcggaggaag gagtcgccga ggagcagcct     180
gaggccccag agtctgagac gagccgccgc cgccccgcc actgcgggga ggaggggag     240 gaggagcggg aggagggacg agctggtcgg gagaagagga aaaaactttt tgagactttt     300
ccgttgccgc tgggagccgg aggcgcgggg acctcttggc gcgacgctgc ccgcgagga     360 ggcaggactt ggggaccca gaccgcctcc ctttgccgcc ggggacgctt gctccctccc     420
tgccccctac acggcgtccc tcaggcgccc ccattccgga ccagccctcg ggagtcgccg     480
acccggcctc ccgcaaatac ttttccccag acctcgggcg caccccctgc acgccgcctt     540
catccccggc ctgtctcctg agccccgcg catcctagac cttttctcct ccaggagacg     600
gatctctctc cgacctgcca cagatcccct attcaagacc acccaccttc tggtaccaga     660
tctcgcccat ctaggttatt tccgtgggat actgagacac ccccggtcca agcctcccct     720
ccaccactgc gcccttctcc ctgaggacct caactttccc tcgaggccct cctacctttt     780
cccgggagac ccccagcccc tgcaggggcg gggcctcccc accacgctag ccctgttcgc     840
cctctcggca gtgccggggg gcgccgcctc ccccatgccg ccctcgggc tgcggctgct     900 gccgctgctg ctaccgctgc tgtggctact ggtgctgacg cctggccggc cggccgccgg     960
actatccacc tgcaagacta tcgacatgga gctggtgaag cggaagcgca tcgaggccat    1020
ccgcggccag atcctgtcca agctgcggct cgccagcccc ccgagccagg gggaggtgcc    1080
gccccggccg ctgcccgagg ccgtgctcgc cctgtacaac agcacccgcg accgggtggc    1140
cggggagagt gcggagccgg aacccgaacc ggaggccgac tactacgcca aggaggtcac    1200
ccgcgtgcta atggtggaaa cccacaacga atctatgac aagttcaagc agagcacaca    1260
cagcatatat atgttcttca acacatcaga gctccgagaa gcagtacctg aacctgtgtt    1320
gctctcccgg gcagagctgc gtctgctgag gctcaagtta aaagtggagc agcatgtgga    1380
gctgtaccag aaatacagca acaattcctg gcgatacctc agcaaccggc tgctggcgcc    1440
```

```
cagcgactcg ccggagtggt tgtcttttga tgtcaccgga gttgtgcggc agtggttgag    1500
ccgcggaggg gaaattgagg gctttcgcct tagcgcccac tgctcctgtg acagcaaaga    1560
taacacactg caagtggaca tcaacgcagg gttcactacc ggccgccgag gtgacctggc    1620
caccattcat ggcatgaacc ggcctttcct gcttctcatg gccacccgc tggagagggc     1680 ccaacatctg caaagctccc ggcaccgccg agccctggac accaactact gcttcagctc    1740
cacggagaag aactgctgcg tgcggcagct gtatattgac ttccgcaagg acctcggctg    1800
gaagtggatc cacgagccca agggctacca tgccaacttc tgcctgggac cctgccccta    1860
catttggagc ctggacacgc agtacagcaa ggtcctggcc ctgtacaacc agcataaccc    1920
gggcgcctcg gcggcgccgt gctgcgtgcc gcaggcgctg gagccgctgc ccatcgtgta    1980
ctacgtgggc cgcaagccca aggtggagca gctgtccaac atgatcgtgc gctcctgcaa    2040
atgcagctga ggccccgtcc cgccccgccc caccccggca ggcccggccc cgccccgccc    2100
cgcccccgct gccttgccct tggggctgt atttaaggac acccgtgccc caagcccacc     2160
tggggcccca ttaaagatgg agagagga                                       2188
```

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      cyno TGFB S1 primer

<400> SEQUENCE: 43
cgcctccccc atgccgccct ccg                                             23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      cyno TGFB Sense 2 primer

<400> SEQUENCE: 44
acaattcctg gcgataccctc                                                20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      cyno TGFB Anti-Sense 1 primer

<400> SEQUENCE: 45
ctcaaccact gccgcacaac                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      cyno TGFB Anti-Sense 2 primer

<400> SEQUENCE: 46
tcagctgcat ttgcaggagc                                                 20

```
<210> SEQ ID NO 47
<211> LENGTH: 231
<212> TYPE: PRT
<213> ORGANISM: Artificial Sequence
<220> FEATURE:
<223> OTHER INFORMATION: Description of Artificial Sequence: Synthetic
      human IgG1; Fc region of LHG-10 polypeptide

<400> SEQUENCE: 47

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 48
<211> LENGTH: 330
<212> TYPE: PRT
<213> ORGANISM: Artificial Sequence
<220> FEATURE:
<223> OTHER INFORMATION: Description of Artificial Sequence: Synthetic
      Heavy chain constant domain of LHG-10 polypeptide
<220> FEATURE:
<221> NAME/KEY: MOD_RES
<222> LOCATION: (180)..(180)
<223> OTHER INFORMATION: Asn or Gln

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Xaa Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      Light chain constant domain of LHG-10 polypeptide

<400> SEQUENCE: 49

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80
```

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 121
<212> TYPE: PRT
<213> ORGANISM: Artificial Sequence
<220> FEATURE:
<223> OTHER INFORMATION: Description of Artificial Sequence: Synthetic
      heavy chain variable region polypeptide

<400> SEQUENCE: 50

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Gly Ile Asn Trp Val Arg Gln Pro Pro Gly Lys Gly Leu Glu Trp Leu
            35                  40                  45

Gly Met Ile Trp Ser Asp Gly Ser Thr Asp Tyr Asn Ser Val Leu Thr
50                  55                  60

Ser Arg Leu Arg Ile Ser Lys Asp Asn Ser Asn Ser Gln Val Phe Leu
65                  70                  75                  80

Lys Met Asn Ser Leu Gln Val Asp Asp Thr Ala Arg Tyr Tyr Cys Ala
                85                  90                  95

Arg Asp Arg Asn Tyr Tyr Asp Tyr Asp Gly Ala Met Asp Tyr Trp Gly
            100                 105                 110

Gln Gly Thr Ser Val Thr Val Ser Ser
        115                 120

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable region polypeptide

<400> SEQUENCE: 51

Asp Ile Gln Val Thr Gln Ser Ser Ser Tyr Leu Ser Val Ser Leu Gly
1               5                   10                  15

Asp Arg Val Thr Ile Thr Cys Lys Ala Ser Asp His Ile Lys Asn Trp
                20                  25                  30

Leu Ala Trp Tyr Gln Gln Lys Pro Gly Ile Ala Pro Arg Leu Leu Val
            35                  40                  45

Ser Gly Ala Thr Ser Leu Glu Ala Gly Val Pro Ser Arg Phe Ser Gly
        50                  55                  60

Ser Gly Ser Gly Lys Asn Phe Thr Leu Ser Ile Thr Ser Leu Gln Thr
65                  70                  75                  80

Glu Asp Val Ala Thr Tyr Tyr Cys Gln Gln Tyr Trp Ser Thr Pro Trp
                85                  90                  95

Thr Phe Gly Gly Gly Thr Thr Leu Glu Ile Arg
            100                 105

<210> SEQ ID NO 52
<211> LENGTH: 5
<212> TYPE: PRT
<213> ORGANISM: Artificial Sequence

```
<220> FEATURE:
<223> OTHER INFORMATION: Description of Artificial Sequence: Synthetic
      VH-CDR1 peptide

<400> SEQUENCE: 52

Gly Tyr Gly Ile Asn
1               5

<210> SEQ ID NO 53
<211> LENGTH: 41
<212> TYPE: PRT
<213> ORGANISM: Homo sapiens

<400> SEQUENCE: 53

His Leu Ser Leu Ala His Asn Arg Leu Ala Met Ala Thr Ala Leu Ser
1               5                   10                  15

Ala Gly Gly Leu Gly Pro Leu Pro Arg Val Thr Ser Leu Asp Leu Ser
            20                  25                  30

Gly Asn Ser Leu Tyr Ser Gly Leu Leu
        35                  40

<210> SEQ ID NO 54
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

His Leu Ser Leu Ala His Asn Arg Leu Ala Thr Gly Met Ala Leu Ser
1               5                   10                  15

Ala Gly Gly Leu Gly Pro Leu Pro Arg Val Thr Ser Leu Asp Leu Ser
            20                  25                  30

Gly Asn Ser Leu Tyr Ser Gly Leu Leu
        35                  40

<210> SEQ ID NO 55
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

His Leu Ser Leu Ala His Asn Arg Leu Ala Met Ala Thr Ala Leu Ser
1               5                   10                  15

Ala Gly Gly Leu Gly Pro Leu Pro Leu Leu Val Ser Leu Asp Leu Ser
            20                  25                  30

Gly Asn Ser Leu Tyr Ser Gly Leu Leu
        35                  40

<210> SEQ ID NO 56
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

His Leu Ser Leu Ala His Asn Arg Leu Ala Met Ala Thr Ala Leu Ser
1               5                   10                  15
```

```
Ala Gly Gly Leu Gly Pro Leu Pro Arg Val Thr Ser Leu Asp Leu Ser
            20              25              30

Gly Asn Ser Leu His Gly Asn Leu Leu
            35              40

<210> SEQ ID NO 57
<211> LENGTH: 41
<212> TYPE: PRT
<213> ORGANISM: Mus sp.

<400> SEQUENCE: 57

His Leu Asn Leu Ala His Asn Arg Leu Ala Thr Gly Met Ala Leu Asn
1               5                   10                  15

Ser Gly Gly Leu Gly Arg Leu Pro Leu Leu Val Ser Leu Asp Leu Ser
            20              25                  30

Gly Asn Ser Leu His Gly Asn Leu Val
            35              40
```